(12) United States Patent
Geresy et al.

(10) Patent No.: US 11,857,252 B2
(45) Date of Patent: Jan. 2, 2024

(54) BEZEL WITH LIGHT BLOCKING FEATURES FOR MODULAR ENERGY SYSTEM

(71) Applicant: Cilag GmbH International, Zug (CH)

(72) Inventors: Stephen D. Geresy, West Chester, OH (US); Stephen M. Leuck, Milford, OH (US); Madeleine C. Jayme, Cincinnati, OH (US); Ryan M. Asher, Cincinnati, OH (US); John A. Weed, III, Monroe, OH (US); Kristen G. Denzinger, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 28 days.

(21) Appl. No.: 17/217,436

(22) Filed: Mar. 30, 2021

(65) Prior Publication Data

US 2022/0313357 A1    Oct. 6, 2022

(51) Int. Cl.
*A61B 18/18*    (2006.01)
*F21V 23/06*    (2006.01)
(Continued)

(52) U.S. Cl.
CPC .............. *A61B 18/18* (2013.01); *F21V 23/06* (2013.01); *F21V 31/005* (2013.01); *F21V 31/03* (2013.01); *A61B 34/25* (2016.02); *A61B 90/37* (2016.02); *A61B 2018/00178* (2013.01); *A61B 2018/1807* (2013.01); *A61B 2090/372* (2016.02); *F21W 2131/205* (2013.01); *F21Y 2115/10* (2016.08)

(58) Field of Classification Search
CPC ........ F21V 23/06; F21V 31/005; F21V 31/03; F21V 33/0068; F21W 2131/205; F21W 2131/20; F21Y 2115/10; A61B 18/18; A61B 34/25; A61B 90/37; A61B 2018/00178; A61B 2018/1807; A61B 2090/372; A61B 2017/00115; A61B 2017/00225; A61B 2560/0443; A61B 18/1206
See application file for complete search history.

(56) References Cited

U.S. PATENT DOCUMENTS 4,171,700 A    10/1979   Farin
4,378,801 A    4/1983    Oosten
(Continued)

FOREIGN PATENT DOCUMENTS

EP    0408160 A1    1/1991
EP    0473987 A1    3/1992
(Continued)

OTHER PUBLICATIONS

Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.
(Continued)

*Primary Examiner* — Peggy A Neils

(57) ABSTRACT

A port module removably coupleable to an energy module of a module energy system is disclosed. The port module includes a light pipe and a receptacle defined by the light pipe. The receptacle is configured to receive a plug of an electrosurgical instrument therein. A seal is defined between the light pipe and the receptacle.

20 Claims, 36 Drawing Sheets

(51) Int. Cl.
  *F21V 31/00* (2006.01)
  *F21V 31/03* (2006.01)
  *A61B 34/00* (2016.01)
  *A61B 90/00* (2016.01)
  *F21Y 115/10* (2016.01)
  *A61B 18/00* (2006.01)
  *F21W 131/205* (2006.01)

(56) References Cited

U.S. PATENT DOCUMENTS

| | | | |
|---|---|---|---|
| 4,640,279 A | 2/1987 | Beard | |
| 4,849,752 A | 7/1989 | Bryant | |
| D303,787 S | 10/1989 | Messenger et al. | |
| 5,041,110 A | 8/1991 | Fleenor | |
| D327,061 S | 6/1992 | Soren et al. | |
| 5,189,277 A | 2/1993 | Boisvert et al. | |
| 5,204,669 A | 4/1993 | Dorfe et al. | |
| 5,318,563 A | 6/1994 | Malis et al. | |
| 5,325,270 A | 6/1994 | Wenger et al. | |
| 5,425,375 A | 6/1995 | Chin et al. | |
| D379,346 S | 5/1997 | Mieki | |
| 5,690,504 A | 11/1997 | Scanlan et al. | |
| 5,693,042 A | 12/1997 | Boiarski et al. | |
| 5,724,468 A | 3/1998 | Leone et al. | |
| 5,788,688 A | 8/1998 | Bauer et al. | |
| 5,910,139 A | 6/1999 | Cochran et al. | |
| 6,049,467 A | 4/2000 | Tamarkin et al. | |
| 6,055,458 A | 4/2000 | Cochran et al. | |
| D431,811 S | 10/2000 | Nishio et al. | |
| 6,179,136 B1 | 1/2001 | Kluge et al. | |
| 6,269,411 B1 | 7/2001 | Reasoner | |
| 6,273,750 B1 | 8/2001 | Malkowski, Jr. | |
| 6,288,606 B1 | 9/2001 | Ekman et al. | |
| 6,416,471 B1 | 7/2002 | Kumar et al. | |
| 6,546,270 B1 | 4/2003 | Goldin et al. | |
| 6,584,358 B2 | 6/2003 | Carter et al. | |
| 6,611,793 B1 | 8/2003 | Burnside et al. | |
| 6,731,514 B2 | 5/2004 | Evans | |
| 6,760,218 B2 | 7/2004 | Fan | |
| 6,839,238 B2 | 1/2005 | Derr et al. | |
| 6,843,657 B2 | 1/2005 | Driscoll et al. | |
| 6,913,471 B2 | 7/2005 | Smith | |
| 7,009,511 B2 | 3/2006 | Mazar et al. | |
| 7,044,949 B2 | 5/2006 | Orszulak et al. | |
| 7,074,205 B1 | 7/2006 | Duffy et al. | |
| 7,134,994 B2 | 11/2006 | Alpert et al. | |
| 7,171,784 B2 | 2/2007 | Eenigenburg | |
| 7,217,269 B2 | 5/2007 | El-Galley et al. | |
| 7,252,664 B2 | 8/2007 | Nasab et al. | |
| 7,331,699 B2 * | 2/2008 | Gawalkiewicz | G02B 6/4296 362/306 |
| 7,344,532 B2 | 3/2008 | Goble et al. | |
| 7,353,068 B2 | 4/2008 | Tanaka et al. | |
| D575,792 S | 8/2008 | Benson | |
| 7,408,439 B2 | 8/2008 | Wang et al. | |
| D579,876 S | 11/2008 | Novotney et al. | |
| D583,328 S | 12/2008 | Chiang | |
| 7,496,418 B2 | 2/2009 | Kim et al. | |
| D589,447 S | 3/2009 | Sasada et al. | |
| 7,500,747 B2 | 3/2009 | Howell et al. | |
| 7,518,502 B2 | 4/2009 | Austin et al. | |
| 7,563,259 B2 | 7/2009 | Takahashi | |
| 7,601,149 B2 | 10/2009 | DiCarlo et al. | |
| 7,637,907 B2 | 12/2009 | Blaha | |
| 7,656,671 B2 | 2/2010 | Liu et al. | |
| 7,757,028 B2 | 7/2010 | Druke et al. | |
| D631,252 S | 1/2011 | Leslie | |
| 7,932,826 B2 | 4/2011 | Fritchie et al. | |
| 7,945,065 B2 | 5/2011 | Menzl et al. | |
| 7,945,342 B2 | 5/2011 | Tsai et al. | |
| 7,982,776 B2 | 7/2011 | Dunki-Jacobs et al. | |
| 7,995,045 B2 | 8/2011 | Dunki-Jacobs | |
| 8,019,094 B2 | 9/2011 | Hsieh et al. | |
| D655,678 S | 3/2012 | Kobayashi et al. | |
| D657,368 S | 4/2012 | Magee et al. | |
| 8,218,279 B2 | 7/2012 | Liao et al. | |
| 8,239,066 B2 | 8/2012 | Jennings et al. | |
| D667,838 S | 9/2012 | Magee et al. | |
| D675,164 S | 1/2013 | Kobayashi et al. | |
| D676,392 S | 2/2013 | Gassauer | |
| D678,196 S | 3/2013 | Miyauchi et al. | |
| D678,304 S | 3/2013 | Yakoub et al. | |
| 8,423,182 B2 | 4/2013 | Robinson et al. | |
| D687,146 S | 7/2013 | Juzkiw et al. | |
| 8,504,136 B1 | 8/2013 | Sun et al. | |
| 8,540,709 B2 | 9/2013 | Allen | |
| 8,567,393 B2 | 10/2013 | Hickle et al. | |
| D704,839 S | 5/2014 | Juzkiw et al. | |
| 8,795,001 B1 | 8/2014 | Lam et al. | |
| 8,819,581 B2 | 8/2014 | Nakamura et al. | |
| 8,840,609 B2 | 9/2014 | Stuebe | |
| D716,333 S | 10/2014 | Chotin et al. | |
| 8,911,437 B2 | 12/2014 | Horlle et al. | |
| 8,917,513 B1 | 12/2014 | Hazzard | |
| 8,920,186 B2 | 12/2014 | Shishikura | |
| 8,923,012 B2 | 12/2014 | Kaufman et al. | |
| 8,968,296 B2 | 3/2015 | McPherson | |
| 8,986,288 B2 | 3/2015 | Konishi | |
| 9,017,326 B2 | 4/2015 | DiNardo et al. | |
| D729,267 S | 5/2015 | Yoo et al. | |
| 9,055,870 B2 | 6/2015 | Meador et al. | |
| 9,065,394 B2 | 6/2015 | Lim et al. | |
| 9,129,054 B2 | 9/2015 | Nawana et al. | |
| 9,160,853 B1 | 10/2015 | Daddi et al. | |
| 9,168,054 B2 | 10/2015 | Turner et al. | |
| 9,168,091 B2 | 10/2015 | Janssen et al. | |
| 9,198,711 B2 | 12/2015 | Joseph | |
| 9,226,766 B2 | 1/2016 | Aldridge et al. | |
| 9,226,791 B2 | 1/2016 | McCarthy et al. | |
| 9,237,921 B2 | 1/2016 | Messerly et al. | |
| 9,265,429 B2 | 2/2016 | St. Pierre et al. | |
| 9,277,961 B2 | 3/2016 | Panescu et al. | |
| 9,277,969 B2 | 3/2016 | Brannan et al. | |
| 9,281,615 B1 | 3/2016 | Plaza et al. | |
| 9,320,646 B2 | 4/2016 | Todd et al. | |
| 9,345,481 B2 | 5/2016 | Hall et al. | |
| 9,345,900 B2 | 5/2016 | Wu et al. | |
| 9,351,653 B1 | 5/2016 | Harrison | |
| 9,427,255 B2 | 8/2016 | Griffith et al. | |
| 9,430,438 B2 | 8/2016 | Biskup | |
| 9,463,646 B2 | 10/2016 | Payne et al. | |
| 9,474,565 B2 | 10/2016 | Shikhman et al. | |
| D772,252 S | 11/2016 | Myers et al. | |
| 9,486,271 B2 | 11/2016 | Dunning | |
| 9,491,895 B2 | 11/2016 | Steeves et al. | |
| 9,532,827 B2 | 1/2017 | Morgan et al. | |
| 9,589,720 B2 | 3/2017 | Akahane | |
| 9,600,031 B2 | 3/2017 | Kaneko et al. | |
| 9,603,277 B2 | 3/2017 | Morgan et al. | |
| D783,675 S | 4/2017 | Yagisawa et al. | |
| D784,270 S | 4/2017 | Bhattacharya | |
| 9,666,974 B2 * | 5/2017 | Bopp | H01R 13/518 |
| 9,713,503 B2 | 7/2017 | Goldschmidt | |
| 9,715,271 B2 | 7/2017 | Kaestner | |
| 9,750,563 B2 | 9/2017 | Shikhman et al. | |
| 9,770,103 B2 | 9/2017 | Cochran et al. | |
| 9,773,093 B2 | 9/2017 | Bernini et al. | |
| 9,782,214 B2 | 10/2017 | Houser et al. | |
| 9,788,907 B1 | 10/2017 | Alvi et al. | |
| 9,804,977 B2 | 10/2017 | Ghosh et al. | |
| D806,721 S | 1/2018 | Fischer | |
| 9,867,670 B2 | 1/2018 | Brannan et al. | |
| 9,892,564 B1 | 2/2018 | Cvetko et al. | |
| 9,907,196 B2 | 2/2018 | Susini et al. | |
| 9,971,395 B2 | 4/2018 | Chenault et al. | |
| 9,974,595 B2 | 5/2018 | Anderson et al. | |
| 9,987,068 B2 | 6/2018 | Anderson et al. | |
| 9,987,072 B2 | 6/2018 | McPherson | |
| 10,028,402 B1 | 7/2018 | Walker | |
| 10,039,589 B2 | 8/2018 | Virshek et al. | |
| D832,211 S | 10/2018 | Ladd et al. | |
| 10,098,527 B2 | 10/2018 | Weisenburgh, II et al. | |
| 10,105,470 B2 | 10/2018 | Reasoner et al. | |

(56) References Cited

U.S. PATENT DOCUMENTS

| | | |
|---|---|---|
| 10,109,835 B2 | 10/2018 | Yang |
| D834,541 S | 11/2018 | You et al. |
| 10,117,702 B2 | 11/2018 | Danziger et al. |
| 10,128,612 B1 | 11/2018 | Casto |
| 10,136,954 B2 | 11/2018 | Johnson et al. |
| 10,137,245 B2 | 11/2018 | Melker et al. |
| 10,147,148 B2 | 12/2018 | Wu et al. |
| 10,166,061 B2 | 1/2019 | Berry et al. |
| 10,170,205 B2 | 1/2019 | Curd et al. |
| 10,201,365 B2 | 2/2019 | Boudreaux et al. |
| 10,339,496 B2 | 7/2019 | Matson et al. |
| 10,357,184 B2 | 7/2019 | Crawford et al. |
| 10,386,990 B2 | 8/2019 | Shikhman et al. |
| 10,441,345 B2 | 10/2019 | Aldridge et al. |
| 10,449,004 B2 | 10/2019 | Ferro et al. |
| 10,475,244 B2 | 11/2019 | Cvetko et al. |
| 10,493,287 B2 | 12/2019 | Yoder et al. |
| 10,499,847 B2 | 12/2019 | Latimer et al. |
| 10,499,996 B2 | 12/2019 | de Almeida Barreto |
| 10,523,122 B2 | 12/2019 | Han et al. |
| 10,531,579 B2 | 1/2020 | Hsiao et al. |
| D876,466 S | 2/2020 | Kobayashi et al. |
| 10,561,753 B2 | 2/2020 | Thompson et al. |
| 10,602,007 B2 | 3/2020 | Takano |
| 10,624,667 B2 | 4/2020 | Faller et al. |
| 10,624,691 B2 | 4/2020 | Wiener et al. |
| 10,675,100 B2 | 6/2020 | Frushour |
| 10,687,884 B2 | 6/2020 | Wiener et al. |
| 10,729,502 B1 | 8/2020 | Wolf et al. |
| 10,743,872 B2 | 8/2020 | Leimbach et al. |
| 10,758,309 B1 | 9/2020 | Chow et al. |
| 10,758,310 B2 | 9/2020 | Shelton, IV et al. |
| 10,772,673 B2 | 9/2020 | Allen, IV et al. |
| 10,878,966 B2 | 12/2020 | Wolf et al. |
| 10,881,399 B2 | 1/2021 | Shelton, IV et al. |
| 10,898,256 B2 | 1/2021 | Yates et al. |
| 10,925,598 B2 | 2/2021 | Scheib et al. |
| 10,932,705 B2 | 3/2021 | Muhsin et al. |
| 10,932,772 B2 | 3/2021 | Shelton, IV et al. |
| 10,950,982 B2 | 3/2021 | Regnier et al. |
| 10,987,176 B2 | 4/2021 | Poltaretskyi et al. |
| 10,989,724 B1 * | 4/2021 | Holmes .................. G01N 35/02 |
| 11,000,270 B2 | 5/2021 | Scheib et al. |
| D924,139 S | 7/2021 | Jayme |
| 11,056,244 B2 | 7/2021 | Shelton, IV et al. |
| 11,065,079 B2 | 7/2021 | Wolf et al. |
| 11,071,595 B2 | 7/2021 | Johnson et al. |
| D928,725 S | 8/2021 | Oberkircher et al. |
| D928,726 S | 8/2021 | Asher et al. |
| 11,083,489 B2 | 8/2021 | Fujii et al. |
| 11,116,587 B2 | 9/2021 | Wolf et al. |
| D939,545 S | 12/2021 | Oberkircher et al. |
| 11,259,793 B2 | 3/2022 | Scheib et al. |
| 11,259,875 B2 | 3/2022 | Boutin et al. |
| 11,272,839 B2 | 3/2022 | Al-Ali et al. |
| 11,284,963 B2 | 3/2022 | Shelton, IV et al. |
| 11,296,540 B2 | 4/2022 | Kirleis et al. |
| 11,304,763 B2 | 4/2022 | Shelton, IV et al. |
| 11,314,846 B1 | 4/2022 | Colin et al. |
| 11,369,366 B2 | 6/2022 | Scheib et al. |
| 11,382,699 B2 | 7/2022 | Wassall et al. |
| 11,382,700 B2 | 7/2022 | Calloway et al. |
| 11,419,604 B2 | 8/2022 | Scheib et al. |
| 11,424,027 B2 | 8/2022 | Shelton, IV |
| 11,432,877 B2 | 9/2022 | Nash et al. |
| 11,464,581 B2 | 10/2022 | Calloway |
| 11,478,820 B2 | 10/2022 | Bales, Jr. et al. |
| 11,504,192 B2 | 11/2022 | Shelton, IV et al. |
| 11,510,750 B2 | 11/2022 | Dulin et al. |
| 11,559,307 B2 | 1/2023 | Shelton, IV et al. |
| 11,564,678 B2 | 1/2023 | Scheib et al. |
| 11,571,205 B2 | 2/2023 | Scheib et al. |
| 11,576,677 B2 | 2/2023 | Shelton, IV et al. |
| 11,589,888 B2 | 2/2023 | Shelton, IV et al. |
| 11,659,023 B2 | 5/2023 | Shelton, IV et al. |
| 2001/0029315 A1 | 10/2001 | Sakurai et al. |
| 2003/0007321 A1 | 1/2003 | Dayley |
| 2003/0078631 A1 | 4/2003 | Nelson et al. |
| 2003/0199794 A1 | 10/2003 | Sakurai et al. |
| 2003/0199864 A1 | 10/2003 | Eick |
| 2004/0030328 A1 | 2/2004 | Eggers et al. |
| 2004/0059323 A1 | 3/2004 | Sturm et al. |
| 2004/0111045 A1 | 6/2004 | Sullivan et al. |
| 2004/0164983 A1 | 8/2004 | Khozai |
| 2005/0010209 A1 | 1/2005 | Lee et al. |
| 2005/0013459 A1 | 1/2005 | Maekawa |
| 2005/0113823 A1 | 5/2005 | Reschke et al. |
| 2005/0165390 A1 | 7/2005 | Mauti et al. |
| 2005/0229110 A1 | 10/2005 | Gegner et al. |
| 2005/0251233 A1 | 11/2005 | Kanzius |
| 2006/0085049 A1 | 4/2006 | Cory et al. |
| 2006/0136622 A1 | 6/2006 | Rouvelin et al. |
| 2006/0149418 A1 | 7/2006 | Anvari |
| 2006/0256516 A1 | 11/2006 | Cho |
| 2007/0061393 A1 | 3/2007 | Moore |
| 2007/0076363 A1 | 4/2007 | Liang et al. |
| 2007/0282321 A1 | 12/2007 | Shah et al. |
| 2008/0072896 A1 | 3/2008 | Setzer et al. |
| 2008/0129465 A1 | 6/2008 | Rao |
| 2008/0249377 A1 | 10/2008 | Molducci et al. |
| 2008/0316304 A1 | 12/2008 | Claus et al. |
| 2009/0036884 A1 | 2/2009 | Gregg et al. |
| 2009/0131929 A1 | 5/2009 | Shimizu |
| 2009/0216091 A1 | 8/2009 | Arndt |
| 2009/0234352 A1 | 9/2009 | Behnke et al. |
| 2010/0036405 A1 | 2/2010 | Giordano et al. |
| 2010/0069939 A1 | 3/2010 | Konishi |
| 2010/0076453 A1 | 3/2010 | Morris et al. |
| 2010/0092006 A1 | 4/2010 | Rosen |
| 2010/0120266 A1 | 5/2010 | Rimborg |
| 2010/0198200 A1 | 8/2010 | Horvath |
| 2010/0312239 A1 | 12/2010 | Sclig |
| 2011/0092972 A1 | 4/2011 | Allen |
| 2011/0093796 A1 | 4/2011 | Plummer et al. |
| 2011/0106567 A1 | 5/2011 | Asher |
| 2011/0125149 A1 | 5/2011 | El-Galley et al. |
| 2011/0130689 A1 | 6/2011 | Cohen et al. |
| 2011/0238063 A1 | 9/2011 | Gregg |
| 2011/0245630 A1 | 10/2011 | St. Pierre et al. |
| 2011/0273465 A1 | 11/2011 | Konishi et al. |
| 2011/0288451 A1 | 11/2011 | Sanai et al. |
| 2011/0306840 A1 | 12/2011 | Allen et al. |
| 2012/0029304 A1 | 2/2012 | Medina et al. |
| 2012/0116380 A1 | 5/2012 | Madan et al. |
| 2012/0132661 A1 | 5/2012 | Gu et al. |
| 2012/0319890 A1 | 12/2012 | McCormack et al. |
| 2013/0031201 A1 | 1/2013 | Kagan et al. |
| 2013/0176220 A1 | 7/2013 | Merschon et al. |
| 2013/0197503 A1 | 8/2013 | Orszulak |
| 2013/0267975 A1 | 10/2013 | Timm et al. |
| 2013/0268283 A1 | 10/2013 | Vann et al. |
| 2014/0009894 A1 | 1/2014 | Yu |
| 2014/0058714 A1 | 2/2014 | Boyer |
| 2014/0087573 A1 | 3/2014 | Kroeckel |
| 2014/0108048 A1 | 4/2014 | Cohn |
| 2014/0155721 A1 | 6/2014 | Hauck et al. |
| 2014/0194683 A1 | 7/2014 | Nakaguchi |
| 2014/0226572 A1 | 8/2014 | Thota et al. |
| 2014/0262598 A1 | 9/2014 | Miki et al. |
| 2014/0263552 A1 | 9/2014 | Hall et al. |
| 2014/0378958 A1 | 12/2014 | Leussler |
| 2015/0190189 A1 | 7/2015 | Yates et al. |
| 2015/0272575 A1 | 10/2015 | Leimbach et al. |
| 2015/0289929 A1 | 10/2015 | Toth et al. |
| 2015/0300923 A1 | 10/2015 | Halbert |
| 2015/0334879 A1 | 11/2015 | Fricker |
| 2016/0045247 A1 | 2/2016 | Heim et al. |
| 2016/0058286 A1 | 3/2016 | Joshua et al. |
| 2016/0062954 A1 | 3/2016 | Ruff et al. |
| 2016/0074096 A1 | 3/2016 | Lieu |
| 2016/0120591 A1 | 5/2016 | Smith et al. |
| 2016/0199240 A1 | 7/2016 | Newkirk et al. |
| 2016/0225192 A1 | 8/2016 | Jones et al. |
| 2016/0249945 A1 | 9/2016 | Shelton, IV et al. |

(56) References Cited

U.S. PATENT DOCUMENTS

| | | |
|---|---|---|
| 2016/0287312 A1 | 10/2016 | Tegg et al. |
| 2016/0287337 A1 | 10/2016 | Aram et al. |
| 2017/0000553 A1 | 1/2017 | Wiener et al. |
| 2017/0024978 A1 | 1/2017 | Gulrez et al. |
| 2017/0078455 A1 | 3/2017 | Fisher et al. |
| 2017/0080346 A1 | 3/2017 | Abbas |
| 2017/0090507 A1 | 3/2017 | Wiener et al. |
| 2017/0151011 A1 | 6/2017 | Brustad et al. |
| 2017/0189096 A1 | 7/2017 | Danziger et al. |
| 2017/0202595 A1 | 7/2017 | Shelton, IV |
| 2017/0209718 A1 | 7/2017 | Tanis |
| 2017/0251305 A1 | 8/2017 | Fathollahi |
| 2017/0252091 A1 | 9/2017 | Honda |
| 2017/0296213 A1 | 10/2017 | Swensgard et al. |
| 2017/0319259 A1 | 11/2017 | Dunning |
| 2017/0360466 A1 | 12/2017 | Brown et al. |
| 2018/0014872 A1 | 1/2018 | Dickerson |
| 2018/0042659 A1 | 2/2018 | Rupp et al. |
| 2018/0049795 A1 | 2/2018 | Swayze et al. |
| 2018/0065248 A1 | 3/2018 | Barral et al. |
| 2018/0078216 A1 | 3/2018 | Baker et al. |
| 2018/0082480 A1 | 3/2018 | White et al. |
| 2018/0099161 A1 | 4/2018 | Honda |
| 2018/0166809 A1 | 6/2018 | Brogan et al. |
| 2018/0206909 A1 | 7/2018 | Brustad et al. |
| 2018/0221005 A1 | 8/2018 | Hamel et al. |
| 2018/0228528 A1 | 8/2018 | Fraasch et al. |
| 2018/0262916 A1 | 9/2018 | Polley et al. |
| 2018/0263557 A1 | 9/2018 | Kahlman |
| 2018/0296283 A1 | 10/2018 | Crawford et al. |
| 2018/0333207 A1 | 11/2018 | Moctezuma De la Barrera |
| 2019/0000478 A1 | 1/2019 | Messerly et al. |
| 2019/0069957 A1 | 3/2019 | Barral et al. |
| 2019/0125455 A1 | 5/2019 | Shelton, IV et al. |
| 2019/0200844 A1 | 7/2019 | Shelton, IV et al. |
| 2019/0200906 A1 | 7/2019 | Shelton, IV et al. |
| 2019/0200981 A1 | 7/2019 | Harris et al. |
| 2019/0201102 A1 | 7/2019 | Shelton, IV et al. |
| 2019/0201140 A1 | 7/2019 | Yates et al. |
| 2019/0201158 A1 | 7/2019 | Shelton, IV et al. |
| 2019/0206563 A1 | 7/2019 | Shelton, IV et al. |
| 2019/0224434 A1 | 7/2019 | Silver et al. |
| 2019/0236840 A1 | 8/2019 | Zuckerman et al. |
| 2019/0247141 A1 | 8/2019 | Batchelor et al. |
| 2019/0278262 A1 | 9/2019 | Taylor et al. |
| 2019/0279524 A1 | 9/2019 | Stoyanov et al. |
| 2019/0348169 A1 | 11/2019 | Gibby et al. |
| 2019/0371012 A1 | 12/2019 | Flexman et al. |
| 2020/0004487 A1 | 1/2020 | Hanajima et al. |
| 2020/0015899 A1 | 1/2020 | Scheib et al. |
| 2020/0015900 A1 | 1/2020 | Scheib et al. |
| 2020/0015907 A1 | 1/2020 | Scheib |
| 2020/0015924 A1 | 1/2020 | Scheib et al. |
| 2020/0030044 A1 | 1/2020 | Wang et al. |
| 2020/0038120 A1 | 2/2020 | Ziraknejad et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078077 A1 | 3/2020 | Henderson et al. |
| 2020/0078078 A1 | 3/2020 | Henderson et al. |
| 2020/0078079 A1 | 3/2020 | Morgan et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078083 A1 | 3/2020 | Sprinkle et al. |
| 2020/0078089 A1 | 3/2020 | Henderson et al. |
| 2020/0078106 A1 | 3/2020 | Henderson et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0159313 A1 | 5/2020 | Gibby et al. |
| 2020/0237422 A1 | 7/2020 | Canady |
| 2020/0265398 A1 | 8/2020 | Lembo |
| 2020/0268472 A1 | 8/2020 | Wolf et al. |
| 2020/0305924 A1 | 10/2020 | Carroll |
| 2020/0305945 A1 | 10/2020 | Morgan et al. |
| 2020/0314569 A1 | 10/2020 | Morgan et al. |
| 2020/0342228 A1 | 10/2020 | Prevrhal et al. |
| 2021/0121246 A1 | 4/2021 | Gudalo |
| 2021/0169578 A1 | 6/2021 | Calloway et al. |
| 2021/0196383 A1 | 7/2021 | Shelton, IV et al. |
| 2021/0203889 A1 | 7/2021 | Fung et al. |
| 2021/0212717 A1 | 7/2021 | Yates et al. |
| 2021/0236755 A1 | 8/2021 | King et al. |
| 2021/0264680 A1 | 8/2021 | Cvetko et al. |
| 2021/0385889 A1 | 12/2021 | Patel |
| 2022/0032442 A1 | 2/2022 | Sheffield et al. |
| 2022/0104896 A1 | 4/2022 | Shelton, IV et al. |
| 2022/0104897 A1 | 4/2022 | Shelton, IV et al. |
| 2022/0104911 A1 | 4/2022 | Shelton, IV et al. |
| 2022/0151704 A1 | 5/2022 | Nikou |
| 2022/0155910 A1 | 5/2022 | Jeong |
| 2022/0261056 A1 | 8/2022 | Motoi et al. |
| 2022/0313338 A1 | 10/2022 | Carroll et al. |
| 2022/0313341 A1 | 10/2022 | Wiener et al. |
| 2022/0313342 A1 | 10/2022 | Leuck et al. |
| 2022/0313369 A1 | 10/2022 | Oberkircher et al. |
| 2022/0313370 A1 | 10/2022 | Morgan et al. |
| 2022/0313371 A1 | 10/2022 | Morgan et al. |
| 2022/0313372 A1 | 10/2022 | Herman et al. |
| 2022/0313373 A1 | 10/2022 | Morgan et al. |
| 2022/0317750 A1 | 10/2022 | Jayme et al. |
| 2022/0317751 A1 | 10/2022 | Samuel et al. |
| 2022/0318179 A1 | 10/2022 | Morgan et al. |
| 2022/0319685 A1 | 10/2022 | Vachon et al. |
| 2022/0319693 A1 | 10/2022 | Oberkircher et al. |
| 2022/0321059 A1 | 10/2022 | Samuel et al. |
| 2022/0322523 A1 | 10/2022 | Jayme et al. |
| 2022/0331013 A1 | 10/2022 | Shelton, IV et al. |
| 2022/0331047 A1 | 10/2022 | Shelton, IV et al. |
| 2022/0331048 A1 | 10/2022 | Shelton, IV et al. |
| 2022/0331049 A1 | 10/2022 | Shelton, IV et al. |
| 2022/0331050 A1 | 10/2022 | Shelton, IV et al. |
| 2022/0331051 A1 | 10/2022 | Shelton, IV et al. |
| 2022/0331052 A1 | 10/2022 | Shelton, IV et al. |
| 2022/0331053 A1 | 10/2022 | Kimball et al. |
| 2022/0331054 A1 | 10/2022 | Kimball et al. |
| 2022/0331056 A1 | 10/2022 | Shelton, IV et al. |
| 2022/0334787 A1 | 10/2022 | Jogan et al. |
| 2022/0335604 A1 | 10/2022 | Vanosdoll et al. |
| 2022/0335660 A1 | 10/2022 | Shelton, IV et al. |
| 2022/0335696 A1 | 10/2022 | Shelton, IV et al. |
| 2022/0336078 A1 | 10/2022 | Wise et al. |
| 2022/0336097 A1 | 10/2022 | Shelton, IV et al. |
| 2022/0337891 A1 | 10/2022 | Burnley et al. |
| 2022/0338049 A1 | 10/2022 | Ross et al. |
| 2023/0038130 A1 | 2/2023 | Cvetko et al. |
| 2023/0039037 A1 | 2/2023 | Henderson et al. |
| 2023/0069787 A1 | 3/2023 | Henderson et al. |
| 2023/0072423 A1 | 3/2023 | Osborn et al. |

FOREIGN PATENT DOCUMENTS

| | | |
|---|---|---|
| EP | 0929263 B1 | 7/1999 |
| EP | 1006892 B1 | 6/2009 |
| EP | 2942023 A2 | 11/2015 |
| JP | 2000089850 A | 3/2000 |
| JP | 2001029353 A | 2/2001 |
| WO | WO-0112089 A1 | 2/2001 |
| WO | WO-2008053485 A1 | 5/2008 |
| WO | WO-2014031800 A1 | 2/2014 |

(56) References Cited

FOREIGN PATENT DOCUMENTS

| WO | WO-2014071184 A1 | 5/2014 |
| --- | --- | --- |
| WO | WO-2015047693 A1 | 4/2015 |
| WO | WO-2017058617 | 4/2017 |
| WO | WO-2018116247 A1 | 6/2018 |
| WO | WO-2019215354 A1 | 11/2019 |
| WO | WO-2021044136 A1 | 3/2021 |

OTHER PUBLICATIONS

IEEE Std 802.3-2012 (Revision of IEEE Std 802.3-2008, published Dec. 28, 2012.

"ATM-MPLS Network Interworking Version 2.0, af-aic-0178.001" ATM Standard, The ATM Forum Technical Committe, published Aug. 2003.

Zhu et al. "Haptic-feedback smart glove as a creative human-machine interface (HMI) for virtual/augmented reality applications," Sci. Adv, vol. 6, No. 19, May 8, 2020.

Qian, et al., "A Review of Augmented Reality in Robotic-Assisted Surgery", IEEE Transactions on Medical Robotics and Bionics, IEEE, vol. 2, No. 1, pp. 1-16, Feb. 2020.

Yu et al., "Skin-Integrated Wireless Haptic Interfaces for Virtual and Augmented Reality," Nature, vol. 575, pp. 473-479, Nov. 21, 2019.

Li et al., "Wearable Energy Harvesters Generating Electricity From Low-Frequency Human Limb Movement," Microsystems & Nanoengineering (2018), vol. 4(24), 13 pages.

"Bowa Arc 400" Oct. 30, 2018, posted at bowa-medical.com, [site visited Aug. 6, 2021], https://www.bowa-medical.com/tradepro/shopru/artikel/allgemein/BOWA_BRO_11181_ARC400_V2.1_2018_10_30_EN.pdf (Year: 2018).

"Electrosurgical Generator ECONT-0201.3" Mar. 18, 2018, posted at contact-endoscopy.com, [site visited Aug. 6, 2021], https://contact-endoscopy.com/electrosurgical-system (Year: 2018).

\* cited by examiner

BEZEL WITH LIGHT BLOCKING FEATURES FOR MODULAR ENERGY SYSTEM

BACKGROUND

The present disclosure relates to various surgical systems, including modular electrosurgical and/or ultrasonic surgical systems. Operating rooms (ORs) are in need of streamlined capital solutions because ORs are a tangled web of cords, devices, and people due to the number of different devices that are needed to complete each surgical procedure. This is a reality of every OR in every market throughout the globe. Capital equipment is a major offender in creating clutter within ORs because most capital equipment performs one task or job, and each type of capital equipment requires unique techniques or methods to use and has a unique user interface. Accordingly, there are unmet consumer needs for capital equipment and other surgical technology to be consolidated in order to decrease the equipment footprint within the OR, streamline the equipment's interfaces, and improve surgical staff efficiency during a surgical procedure by reducing the number of devices that surgical staff members need to interact with.

SUMMARY

In various aspects, a port module removably coupleable to an energy module of a module energy system is disclosed. The port module includes a light pipe and a receptacle defined by the light pipe. The receptacle is configured to receive a plug of an electrosurgical instrument therein. A seal is defined between the light pipe and the receptacle.

In various aspects, an energy module of a module energy system is disclosed. The energy module includes an enclosure defining a first aperture, a control circuit positioned within the enclosure, a port module, and a light blocking insert. The control circuit defines a second aperture aligned with the first aperture. The port module extends through the first aperture and the second aperture. A gap is defined between the second aperture and the port module. The light blocking insert is positioned in the gap.

In various aspects, an energy module of a module energy system is disclosed. The energy module includes an enclosure defining a first aperture, a control circuit positioned within the enclosure, a port module, and a light blocking insert. The control circuit defines a second aperture aligned with the first aperture. The port module extends through the first aperture and the second aperture. The port module includes a light pipe and a receptacle. The receptacle is configured to receive a plug of an electrosurgical instrument therein. A seal is defined between the light pipe and the receptacle. A gap is defined between the second aperture and the port module. The light blocking insert is positioned in the gap.

FIGURES

The various aspects described herein, both as to organization and methods of operation, together with further objects and advantages thereof, may best be understood by reference to the following description, taken in conjunction with the accompanying drawings as follows.

Corresponding reference characters indicate corresponding parts throughout the several views. The exemplifications set out herein illustrate various disclosed aspects, in one form, and such exemplifications are not to be construed as limiting the scope thereof in any manner.

Figure 1:
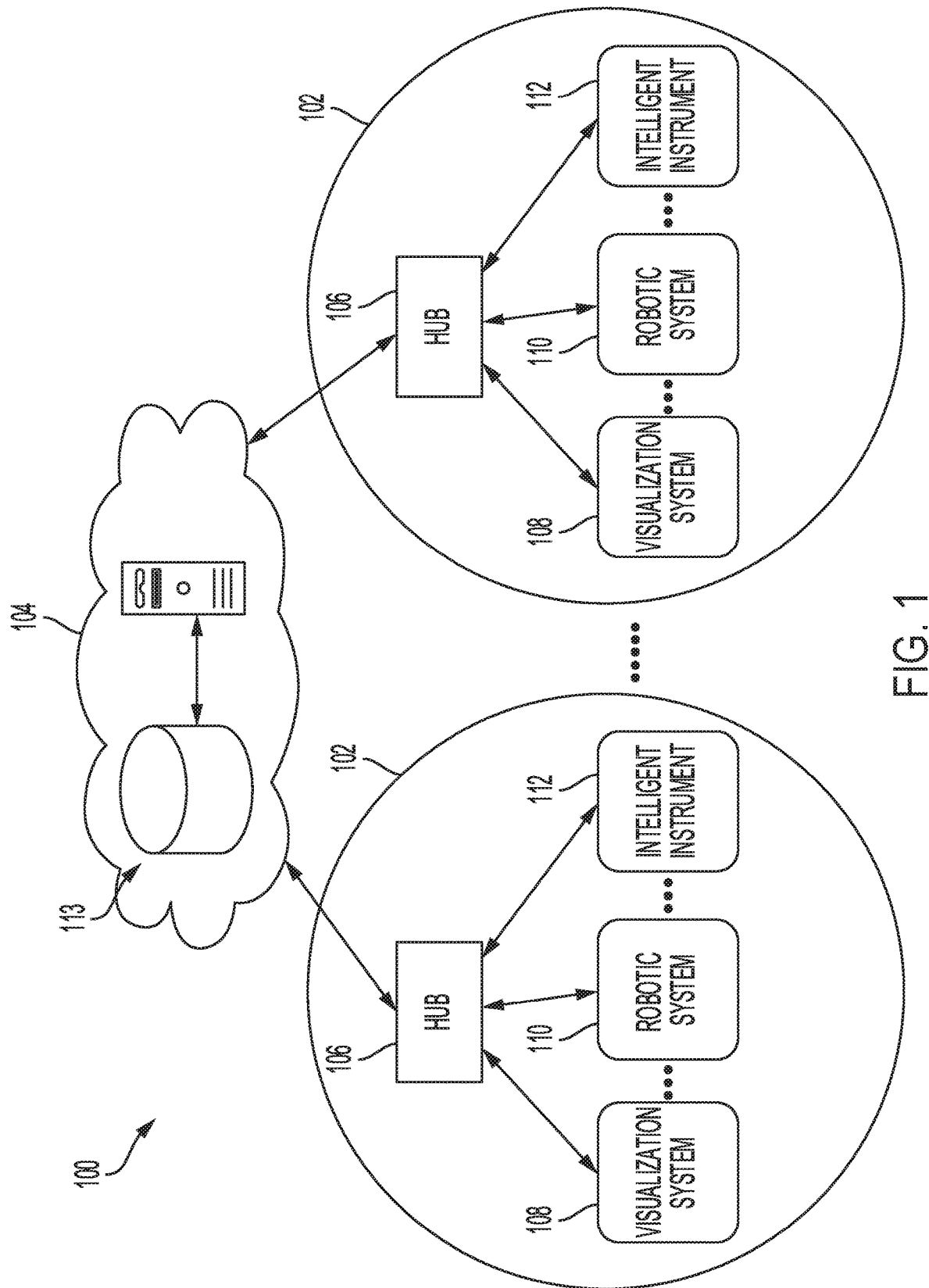
FIG. 1 is a block diagram of a computer-implemented interactive surgical system, in accordance with at least one aspect of the present disclosure.

Applicant of the present application owns the following U.S. Patent Applications filed on Mar. 30, 2021, the disclosure of each of which is herein incorporated by reference in its entirety:

U.S. patent application Ser. No. 17/217,394, titled METHOD FOR MECHANICAL PACKAGING FOR MODULAR ENERGY SYSTEM, now U.S. Patent Application Publication No. 2022/0322523;

U.S. patent application Ser. No. 17/217,4021, titled BACKPLANE CONNECTOR ATTACHMENT MECHANISM FOR MODULAR ENERGY SYSTEM, now U.S. Patent Application Publication No. 2022/0317750;

U.S. patent application Ser. No. 17/217,446, titled HEADER FOR MODULAR ENERGY SYSTEM, now U.S. Patent Application Publication No. 2022/0313342;

U.S. patent application Ser. No. 17/217,403, titled SURGICAL PROCEDURALIZATION VIA MODULAR ENERGY SYSTEM, now U.S. Patent Application Publication No. 2022/0313341:

U.S. patent application Ser. No. 17/217,424, titled METHOD FOR ENERGY DELIVERY FOR MODULAR ENERGY SYSTEM, now U.S. Patent Application Publication No. 2022/0317751;

U.S. patent application Ser. No. 17/217,439, titled MODULAR ENERGY SYSTEM WITH DUAL AMPLIFIERS AND TECHNIQUES FOR UPDATING PARAMETERS THEREOF, now U.S. Patent Application Publication No. 2022/0321059;

U.S. patent application Ser. No. 14/217,471, titled MODULAR ENERGY SYSTEM WITH MULTI-ENERGY PORT SPLITTER FOR MULTIPLE ENERGY DEVICES, now U.S. Patent Application Publication No. 2022/0313373.

U.S. patent application Ser. No. 17/217,385, titled METHOD FOR INTELLIGENT INSTRUMENTS FOR MODULAR ENERGY SYSTEM, now U.S. Patent Application Publication No. 2022/0313369:

U.S. patent application Ser. No. 17/217,392, titled RADIO FREQUENCY IDENTIFICATION TOKEN FOR WIRELESS SURGICAL INSTRUMENTS, now U.S. Patent Application Publication No. 2022/0319693;

U.S. patent application Ser. No. 14/217,397, titled INTELLIGENT DATA PORTS FOR MODULAR ENERGY SYSTEMS, now U.S. Patent Application Publication No. 2022/0318179:

U.S. patent application Ser. No. 17/217,405, titled METHOD FOR SYSTEM ARCHITECTURE FOR MODULAR ENERGY SYSTEM, now U.S. Patent Application Publication No. 2022/0313370;

U.S. patent application Ser. No. 17/217,423, titled USER INTERFACE MITIGATION TECHNIQUES FOR MODULAR ENERGY SYSTEMS, now U.S. Patent Application Publication No. 2022/0313371;

U.S. patent application Ser. No. 17/217,429, titled ENERGY DELIVERY MITIGATIONS FOR MODULAR ENERGY SYSTEMS, now U.S. Patent Application Publication No. 2022/0313338;

U.S. patent application Ser. No. 17/217,449, titled ARCHITECTURE FOR MODULAR ENERGY SYSTEM, now U.S. Patent Application Publication No. 2022/0313372; and U.S. patent application Ser. No. 17/217,461, titled MODULAR ENERGY SYSTEM WITH HARDWARE MITIGATED COMMUNICATION, now U.S. Patent Application Publication No. 2022/0319685.

Applicant of the present application owns the following U.S. Patent Applications filed Sep. 5, 2019, the disclosure of each of which is herein incorporated by reference in its entirety:

U.S. patent application Ser. No. 16/562,144, titled METHOD FOR CONTROLLING A MODULAR ENERGY SYSTEM USER INTERFACE, now U.S. Patent Application Publication No. 2020/0078106;

U.S. patent application Ser. No. 16/562,151, titled PASSIVE HEADER MODULE FOR A MODULAR ENERGY SYSTEM, now U.S. Patent Application Publication No. 2020/0078110;

U.S. patent application Ser. No. 16/562,157, titled CONSOLIDATED USER INTERFACE FOR MODULAR ENERGY SYSTEM, now U.S. Patent Application Publication No. 2020/0081585;

U.S. patent application Ser. No. 16/562,159, titled AUDIO TONE CONSTRUCTION FOR AN ENERGY MODULE OF A MODULAR ENERGY SYSTEM, now U.S. Patent Application Publication No. 2020/0314569;

U.S. patent application Ser. No. 16/562,163, titled ADAPTABLY CONNECTABLE AND REASSIGNABLE SYSTEM ACCESSORIES FOR MODULAR ENERGY SYSTEM, now U.S. Patent Application Publication No. 2020/0078111;

U.S. patent application Ser. No. 16/562,123, titled METHOD FOR CONSTRUCTING AND USING A MODULAR SURGICAL ENERGY SYSTEM WITH MULTIPLE DEVICES, now U.S. Patent Application Publication No. 2020/0100830;

U.S. patent application Ser. No. 16/562,135, titled METHOD FOR CONTROLLING AN ENERGY MODULE OUTPUT, now U.S. Patent Application Publication No. 2020/0078076;

U.S. patent application Ser. No. 16/562,180, titled ENERGY MODULE FOR DRIVING MULTIPLE ENERGY MODALITIES, now U.S. Patent Application Publication No. 2020/0078080;

U.S. patent application Ser. No. 16/562,184, titled GROUNDING ARRANGEMENT OF ENERGY MODULES, now U.S. Patent Application Publication No. 2020/0078081;

U.S. patent application Ser. No. 16/562,188, titled BACKPLANE CONNECTOR DESIGN TO CONNECT STACKED ENERGY MODULES, now U.S. Patent Application Publication No. 2020/0078116;

U.S. patent application Ser. No. 16/562,195, titled ENERGY MODULE FOR DRIVING MULTIPLE ENERGY MODALITIES THROUGH A PORT, now U.S. Patent Application Publication No. 20200078117;

U.S. patent application Ser. No. 16/562,202 titled SURGICAL INSTRUMENT UTILIZING DRIVE SIGNAL TO POWER SECONDARY FUNCTION, now U.S. Patent Application Publication No. 2020/0078082;

U.S. patent application Ser. No. 16/562,142, titled METHOD FOR ENERGY DISTRIBUTION IN A SURGICAL MODULAR ENERGY SYSTEM, now U.S. Patent Application Publication No. 2020/0078070;

U.S. patent application Ser. No. 16/562,169, titled SURGICAL MODULAR ENERGY SYSTEM WITH A SEGMENTED BACKPLANE, now U.S. Patent Application Publication No. 2020/0078112;

U.S. patent application Ser. No. 16/562,185, titled SURGICAL MODULAR ENERGY SYSTEM WITH FOOTER MODULE, now U.S. Patent Application Publication No. 2020/0078115;

U.S. patent application Ser. No. 16/562,203, titled POWER AND COMMUNICATION MITIGATION ARRANGEMENT FOR MODULAR SURGICAL ENERGY SYSTEM, now U.S. Patent Application Publication No. 2020/0078118;

U.S. patent application Ser. No. 16/562,212, titled MODULAR SURGICAL ENERGY SYSTEM WITH MODULE POSITIONAL AWARENESS SENSING WITH VOLTAGE DETECTION, now U.S. Patent Application Publication No. 2020/0078119;

U.S. patent application Ser. No. 16/562,234, titled MODULAR SURGICAL ENERGY SYSTEM WITH MODULE POSITIONAL AWARENESS SENSING WITH TIME COUNTER, now U.S. Patent Application Publication No. 2020/0305945;

U.S. patent application Ser. No. 16/562,243, titled MODULAR SURGICAL ENERGY SYSTEM WITH MODULE POSITIONAL AWARENESS WITH DIGITAL LOGIC, now U.S. Patent Application Publication No. 2020/0078120;

U.S. patent application Ser. No. 16/562,125, titled METHOD FOR COMMUNICATING BETWEEN MODULES AND DEVICES IN A MODULAR SURGICAL SYSTEM, now U.S. Patent Application Publication No. 2020/0100825;

U.S. patent application Ser. No. 16/562,137, titled FLEXIBLE HAND-SWITCH CIRCUIT, now U.S. Patent Application Publication No. 2020/0106220;

U.S. patent application Ser. No. 16/562,143, titled FIRST AND SECOND COMMUNICATION PROTOCOL ARRANGEMENT FOR DRIVING PRIMARY AND SECONDARY DEVICES THROUGH A SINGLE PORT, now U.S. Patent Application Publication No. 2020/0090808;

U.S. patent application Ser. No. 16/562,148, titled FLEXIBLE NEUTRAL ELECTRODE, now U.S. Patent Application Publication No. 2020/0078077;

U.S. patent application Ser. No. 16/562,154, titled SMART RETURN PAD SENSING THROUGH MODULATION OF NEAR FIELD COMMUNICATION AND CONTACT QUALITY MONITORING SIGNALS, now U.S. Patent Application Publication No. 2020/0078089;

U.S. patent application Ser. No. 16/562,162, titled AUTOMATIC ULTRASONIC ENERGY ACTIVATION CIRCUIT DESIGN FOR MODULAR SURGICAL SYSTEMS, now U.S. Patent Application Publication No. 2020/0305924;

U.S. patent application Ser. No. 16/562,167, titled COORDINATED ENERGY OUTPUTS OF SEPARATE BUT CONNECTED MODULES, now U.S. Patent Application Publication No. 2020/0078078;

U.S. patent application Ser. No. 16/562,170, titled MANAGING SIMULTANEOUS MONOPOLAR OUTPUTS USING DUTY CYCLE AND SYNCHRONIZATION, now U.S. Patent Application Publication No. 2020/0078079;

U.S. patent application Ser. No. 16/562,172, titled PORT PRESENCE DETECTION SYSTEM FOR MODULAR ENERGY SYSTEM, now U.S. Patent Application Publication No. 2020/0078113;

U.S. patent application Ser. No. 16/562,175, titled INSTRUMENT TRACKING ARRANGEMENT BASED ON REAL TIME CLOCK INFORMATION, now U.S. Patent Application Publication No. 2020/0078071;

U.S. patent application Ser. No. 16/562,177, titled REGIONAL LOCATION TRACKING OF COMPO- NENTS OF A MODULAR ENERGY SYSTEM, now U.S. Patent Application Publication No. 2020/0078114;

U.S. Design patent application Ser. No. 29/704,610, titled ENERGY MODULE;

U.S. Design patent application Ser. No. 29/704,614, titled ENERGY MODULE MONOPOLAR PORT WITH FOURTH SOCKET AMONG THREE OTHER SOCKETS;

U.S. Design patent application Ser. No. 29/704,616, titled BACKPLANE CONNECTOR FOR ENERGY MODULE; and U.S. Design patent application Ser. No. 29/704,617, titled ALERT SCREEN FOR ENERGY MODULE.

Applicant of the present application owns the following U.S. Patent Provisional applications filed Mar. 29, 2019, the disclosure of each of which is herein incorporated by reference in its entirety:

U.S. Provisional Patent Application Ser. No. 62/826,584, titled MODULAR SURGICAL PLATFORM ELECTRICAL ARCHITECTURE;

U.S. Provisional Patent Application Ser. No. 62/826,587, titled MODULAR ENERGY SYSTEM CONNECTIVITY;

U.S. Provisional Patent Application Ser. No. 62/826,588, titled MODULAR ENERGY SYSTEM INSTRUMENT COMMUNICATION TECHNIQUES; and U.S. Provisional Patent Application Ser. No. 62/826,592, titled MODULAR ENERGY DELIVERY SYSTEM.

Applicant of the present application owns the following U.S. Patent Provisional application filed Sep. 7, 2018, the disclosure of each of which is herein incorporated by reference in its entirety:

U.S. Provisional Patent Application Ser. No. 62/728,480, titled MODULAR ENERGY SYSTEM AND USER INTERFACE.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various aspects are directed to improved ultrasonic surgical devices, electrosurgical devices and generators for use therewith. Aspects of the ultrasonic surgical devices can be configured for transecting and/or coagulating tissue during surgical procedures, for example. Aspects of the electrosurgical devices can be configured for transecting, coagulating, scaling, welding and/or desiccating tissue during surgical procedures, for example.

Surgical System Hardware

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 2:
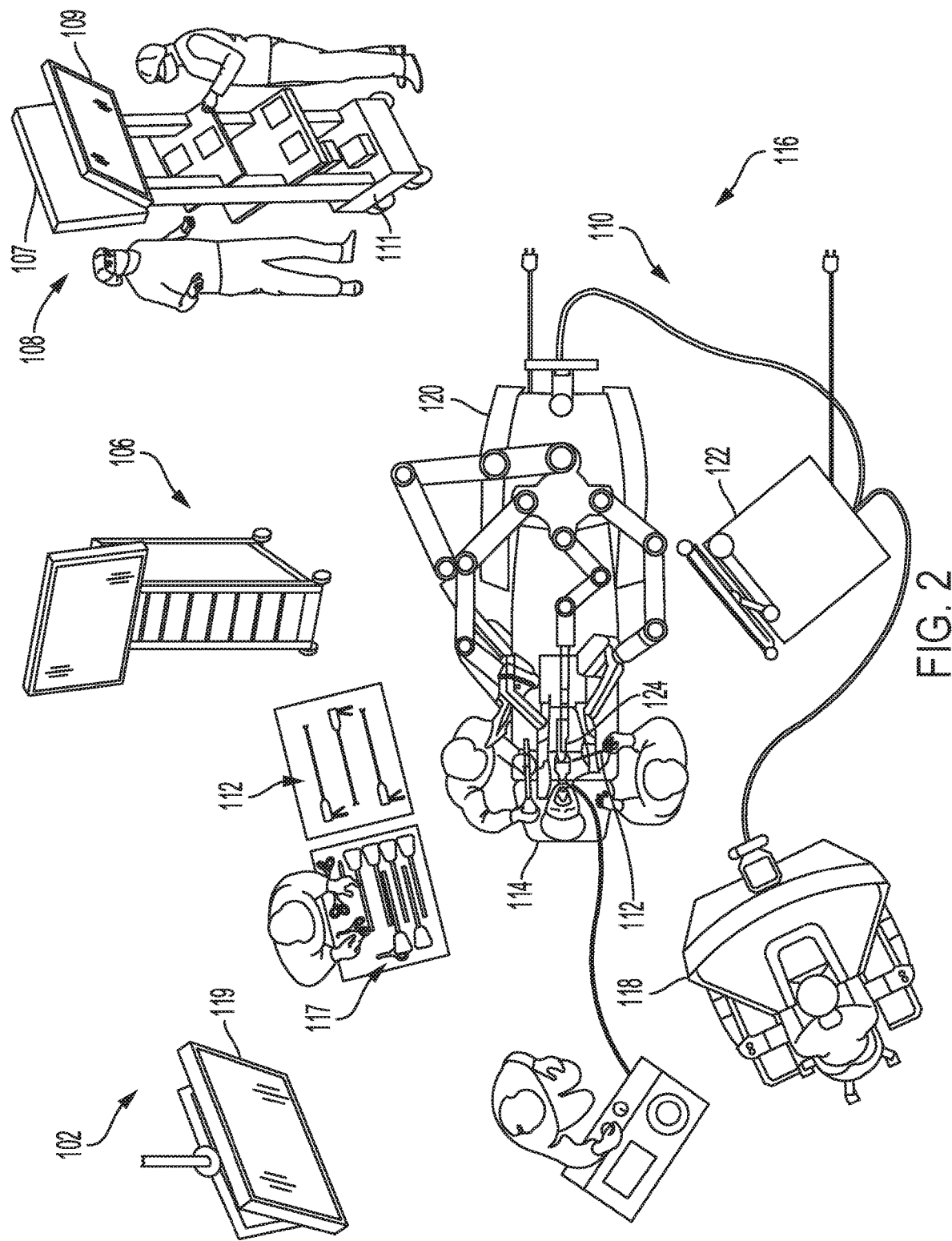
FIG. 2 is a surgical system being used to perform a surgical procedure in an operating room, in accordance with at least one aspect of the present disclosure.

FIG. 2 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngoneproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

In various aspects, the visualization system 108 includes one or more imaging sensors, one or more image-processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading SURGICAL INSTRUMENT HARDWARE and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Figure 3:
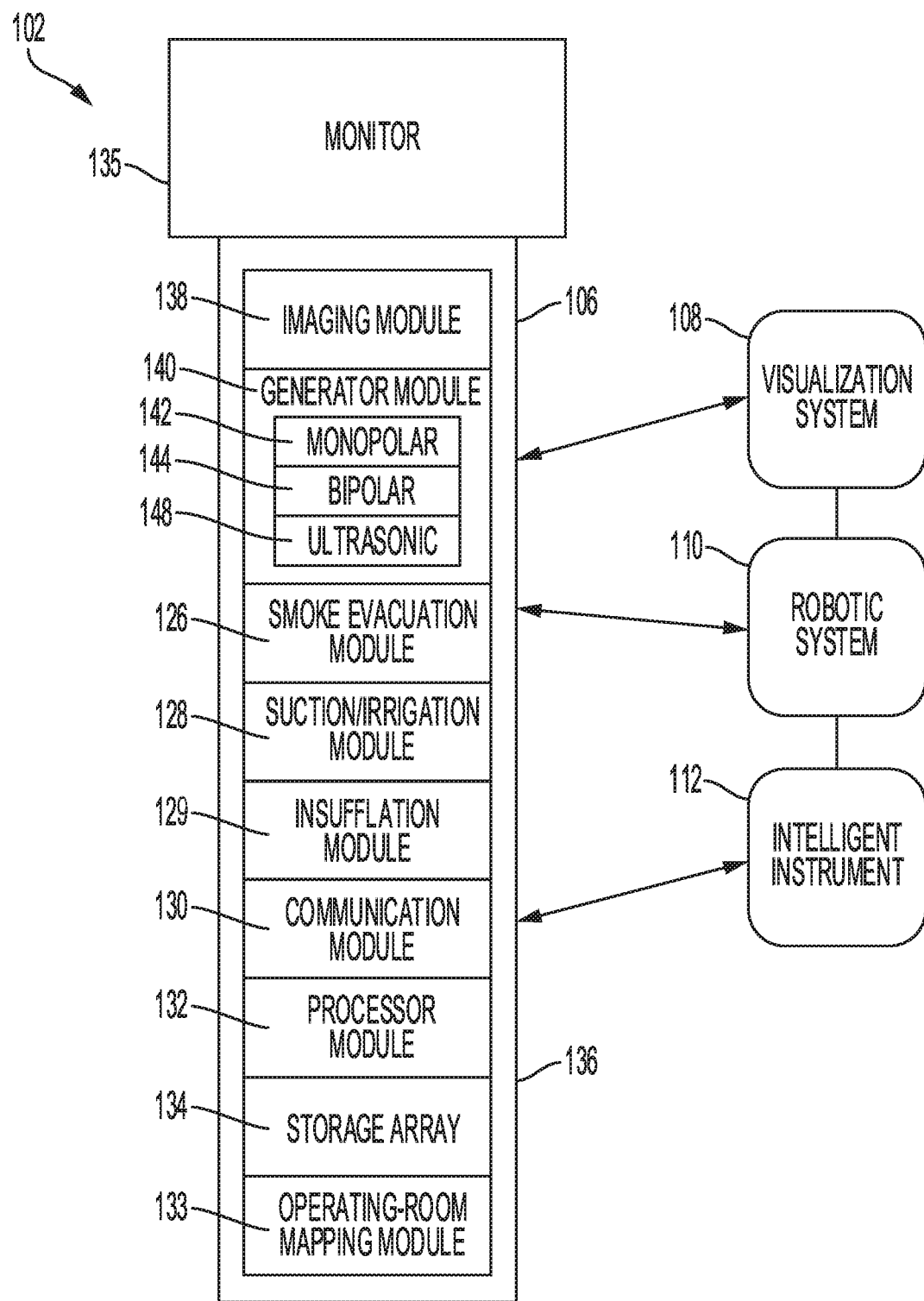
FIG. 3 is a surgical hub paired with a visualization system, a robotic system, and an intelligent instrument, in accordance with at least one aspect of the present disclosure.

Referring now to FIG. 3, a hub 106 is depicted in communication with a visualization system 108, a robotic system 110, and a handheld intelligent surgical instrument 112. In some aspects, the visualization system 108 may be a separable piece of equipment. In alternative aspects, the visualization system 108 could be contained within the hub 106 as a functional module. The hub 106 includes a hub display 135, an imaging module 138, a generator module 140, a communication module 130, a processor module 132, a storage array 134, and an operating room mapping module 133. In certain aspects, as illustrated in FIG. 3, the hub 106 further includes a smoke evacuation module 126, a suction/irrigation module 128, and/or an insufflation module 129. In certain aspects, any of the modules in the hub 106 may be combined with each other into a single module.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes one or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts. In one aspect, the first energy-generator module is slidably movable into an electrical engagement with the power and data contacts and wherein the first energy-generator module is slidably movable out of the electrical engagement with the first power and data contacts. In an alternative aspect, the first energy-generator module is stackably movable into an electrical engagement with the power and data contacts and wherein the first energy-generator module is stackably movable out of the electrical engagement with the first power and data contacts.

Further to the above, the modular surgical enclosure also includes a second energy-generator module configured to generate a second energy, either the same or different than the first energy, for application to the tissue, and a second docking station comprising a second docking port that includes second data and power contacts. In one aspect, the second energy-generator module is slidably movable into an electrical engagement with the power and data contacts, and wherein the second energy-generator module is slidably movable out of the electrical engagement with the second power and data contacts. In an alternative aspect, the second energy-generator module is stackably movable into an electrical engagement with the power and data contacts, and wherein the second energy-generator module is stackably movable out of the electrical engagement with the second power and data contacts.

In addition, the modular surgical enclosure also includes a communication bus between the first docking port and the second docking port, configured to facilitate communication between the first energy-generator module and the second energy-generator module.

Referring to FIG. 3, aspects of the present disclosure are presented for a hub modular enclosure 136 that allows the modular integration of a generator module 140, a smoke evacuation module 126, a suction/irrigation module 128, and an insufflation module 129. The hub modular enclosure 136 further facilitates interactive communication between the modules 140, 126, 128, 129. The generator module 140 can be a generator module with integrated monopolar, bipolar, and ultrasonic components supported in a single housing unit slidably insertable into the hub modular enclosure 136. The generator module 140 can be configured to connect to a monopolar device 142, a bipolar device 144, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128, 129 and interactive communication therebetween.

Generator Hardware

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixedsignal, and often radio-frequency functions—all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; a SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

Modular devices include the modules (as described in connection with FIG. 3, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

Figure 4:
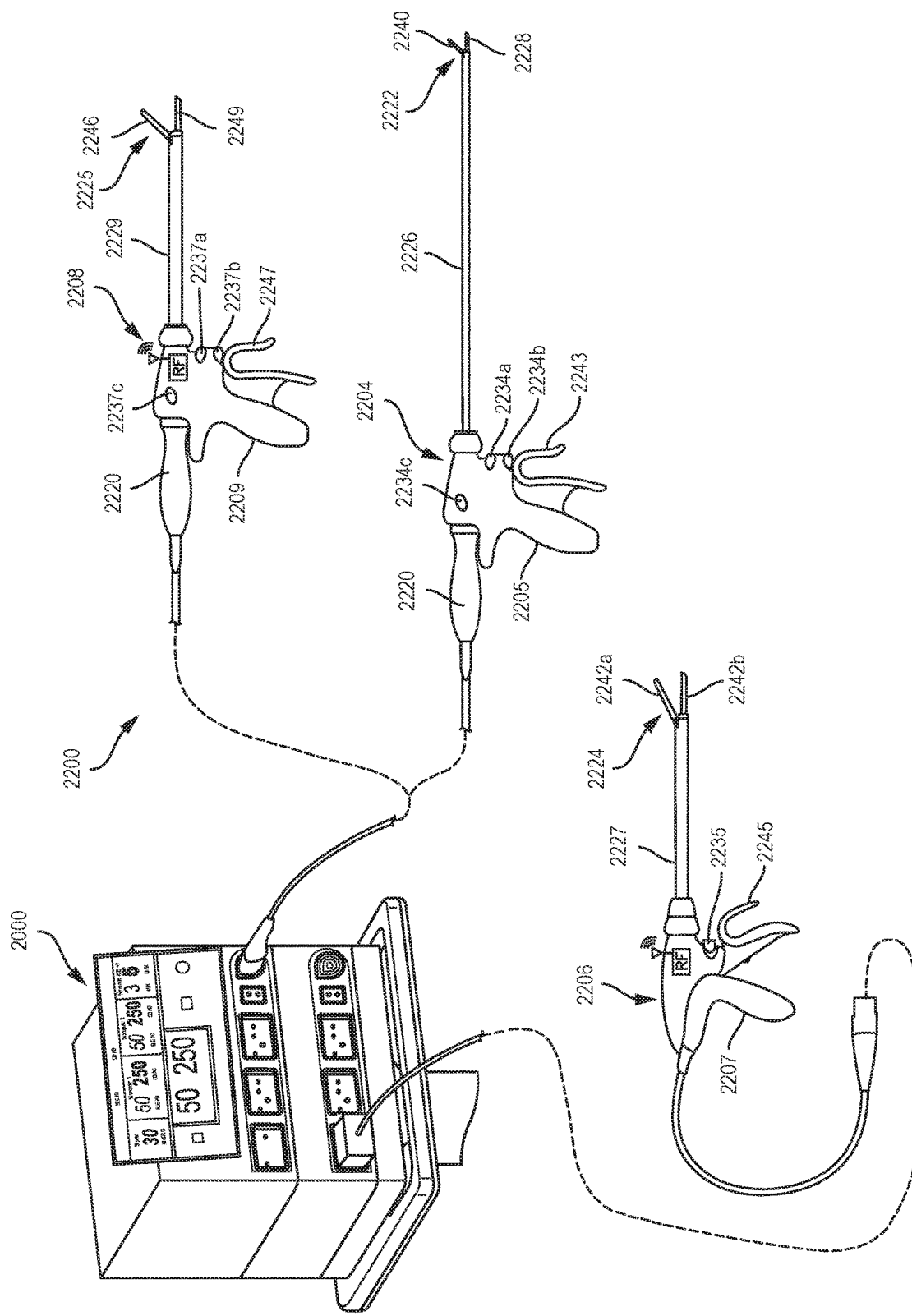
FIG. 4 is a surgical system comprising a generator and various surgical instruments usable therewith, in accordance with at least one aspect of the present disclosure.

FIG. 4 illustrates one form of a surgical system 2200 comprising a modular energy system 2000 and various surgical instruments 2204, 2206, 2208 usable therewith, where the surgical instrument 2204 is an ultrasonic surgical instrument, the surgical instrument 2206 is an RF electrosurgical instrument, and the multifunction surgical instrument 2208 is a combination ultrasonic/RF electrosurgical instrument. The modular energy system 2000 is configurable for use with a variety of surgical instruments. According to various forms, the modular energy system 2000 may be configurable for use with different surgical instruments of different types including, for example, ultrasonic surgical instruments 2204, RF electrosurgical instruments 2206, and multifunction surgical instruments 2208 that integrate RF and ultrasonic energies delivered individually or simultaneously from the modular energy system 2000. Although in the form of FIG. 4 the modular energy system 2000 is shown separate from the surgical instruments 2204, 2206, 2208 in one form, the modular energy system 2000 may be formed integrally with any of the surgical instruments 2204, 2206, 2208 to form a unitary surgical system. The modular energy system 2000 may be configured for wired or wireless communication.

The modular energy system 2000 is configured to drive multiple surgical instruments 2204, 2206, 2208. The first surgical instrument is an ultrasonic surgical instrument 2204 and comprises a handpiece 2205 (HP), an ultrasonic transducer 2220, a shaft 2226, and an end effector 2222. The end effector 2222 comprises an ultrasonic blade 2228 acoustically coupled to the ultrasonic transducer 2220 and a clamp arm 2240. The handpiece 2205 comprises a trigger 2243 to operate the clamp arm 2240 and a combination of the toggle buttons 2234a, 2234b, 2234c to energize and drive the ultrasonic blade 2228 or other function. The toggle buttons 2234a, 2234b, 2234c can be configured to energize the ultrasonic transducer 2220 with the modular energy system 2000.

The modular energy system 2000 also is configured to drive a second surgical instrument 2206. The second surgical instrument 2206 is an RF electrosurgical instrument and comprises a handpiece 2207 (HP), a shaft 2227, and an end effector 2224. The end effector 2224 comprises electrodes in clamp arms 2242a, 2242b and return through an electrical conductor portion of the shaft 2227. The electrodes are coupled to and energized by a bipolar energy source within the modular energy system 2000. The handpiece 2207 comprises a trigger 2245 to operate the clamp arms 2242a, 2242b and an energy button 2235 to actuate an energy switch to energize the electrodes in the end effector 2224.

The modular energy system 2000 also is configured to drive a multifunction surgical instrument 2208. The multifunction surgical instrument 2208 comprises a handpiece 2209 (HP), a shaft 2229, and an end effector 2225. The end effector 2225 comprises an ultrasonic blade 2249 and a clamp arm 2246. The ultrasonic blade 2249 is acoustically coupled to the ultrasonic transducer 2220. The ultrasonic transducer 2220 may be separable from or integral to the handpiece 2209. The handpiece 2209 comprises a trigger 2247 to operate the clamp arm 2246 and a combination of the toggle buttons 2237a, 2237b, 2237c to energize and drive the ultrasonic blade 2249 or other function. The toggle buttons 2237a, 2237b, 2237c can be configured to energize the ultrasonic transducer 2220 with the modular energy system 2000 and energize the ultrasonic blade 2249 with a bipolar energy source also contained within the modular energy system 2000.

The modular energy system 2000 is configurable for use with a variety of surgical instruments. According to various forms, the modular energy system 2000 may be configurable for use with different surgical instruments of different types including, for example, the ultrasonic surgical instrument 2204, the RF electrosurgical instrument 2206, and the multifunction surgical instrument 2208 that integrates RF and ultrasonic energies delivered individually or simultaneously from the modular energy system 2000. Although in the form of FIG. 4 the modular energy system 2000 is shown separate from the surgical instruments 2204, 2206, 2208, in another form the modular energy system 2000 may be formed integrally with any one of the surgical instruments 2204, 2206, 2208 to form a unitary surgical system. Further aspects of generators for digitally generating electrical signal waveforms and surgical instruments are described in U.S. Patent Application Publication No. 2017/0086914, which is herein incorporated by reference in its entirety.

Situational Awareness

Although an "intelligent" device including control algorithms that respond to sensed data can be an improvement over a "dumb" device that operates without accounting for sensed data, some sensed data can be incomplete or inconclusive when considered in isolation, i.e., without the context of the type of surgical procedure being performed or the type of tissue that is being operated on. Without knowing the procedural context (e.g., knowing the type of tissue being operated on or the type of procedure being performed), the control algorithm may control the modular device incorrectly or sub optimally given the particular context-free sensed data. For example, the optimal manner for a control algorithm to control a surgical instrument in response to a particular sensed parameter can vary according to the particular tissue type being operated on. This is due to the fact that different tissue types have different properties (e.g., resistance to tearing) and thus respond differently to actions taken by surgical instruments. Therefore, it may be desirable for a surgical instrument to take different actions even when the same measurement for a particular parameter is sensed. As one specific example, the optimal manner in which to control a surgical stapling and cutting instrument in response to the instrument sensing an unexpectedly high force to close its end effector will vary depending upon whether the tissue type is susceptible or resistant to tearing. For tissues that are susceptible to tearing, such as lung tissue, the instrument's control algorithm would optimally ramp down the motor in response to an unexpectedly high force to close to avoid tearing the tissue. For tissues that are resistant to tearing, such as stomach tissue, the instrument's control algorithm would optimally ramp up the motor in response to an unexpectedly high force to close to ensure that the end effector is clamped properly on the tissue. Without knowing whether lung or stomach tissue has been clamped, the control algorithm may make a suboptimal decision.

Figure 5:
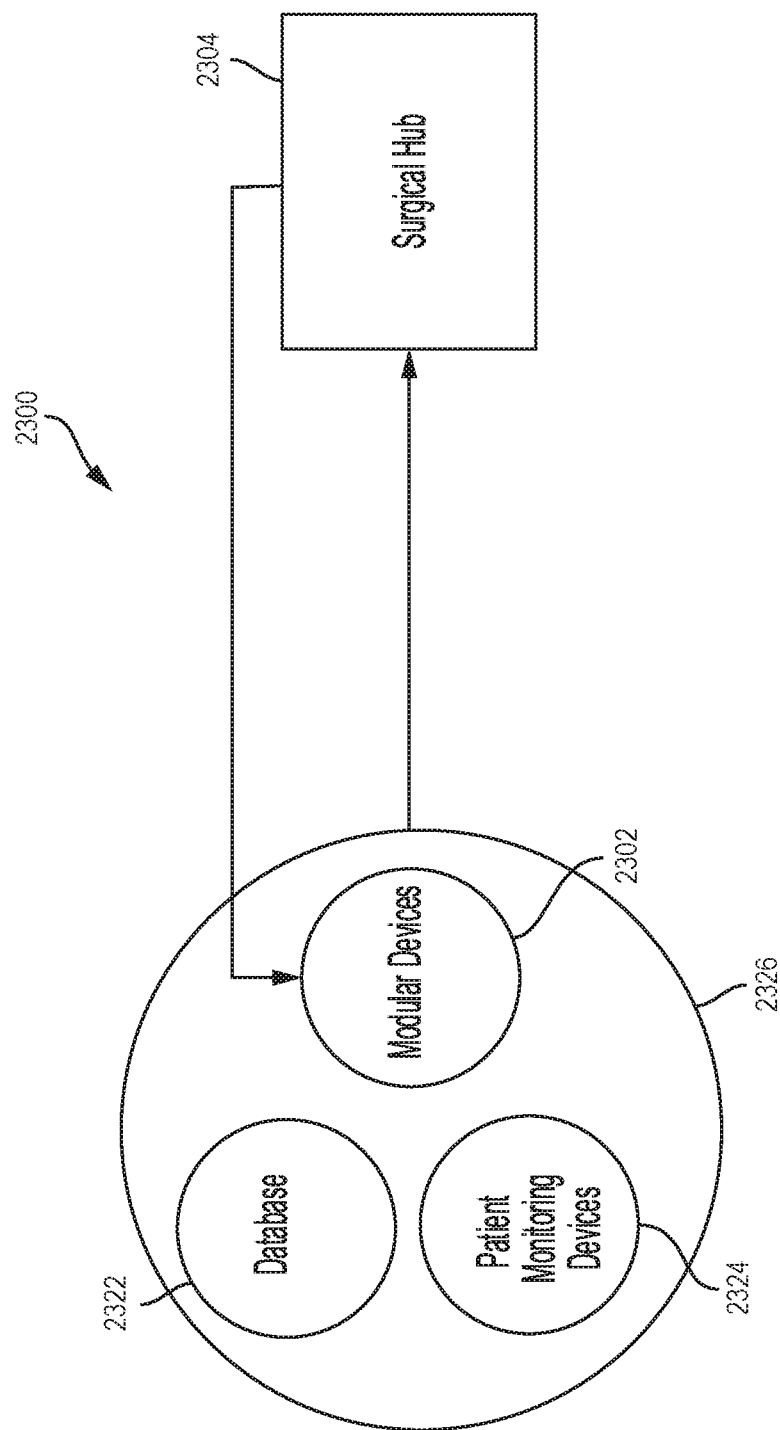
FIG. 5 is a diagram of a situationally aware surgical system, in accordance with at least one aspect of the present disclosure.

One solution utilizes a surgical hub including a system that is configured to derive information about the surgical procedure being performed based on data received from various data sources and then control the paired modular devices accordingly. In other words, the surgical hub is configured to infer information about the surgical procedure from received data and then control the modular devices paired to the surgical hub based upon the inferred context of the surgical procedure. FIG. 5 illustrates a diagram of a situationally aware surgical system 2300, in accordance with at least one aspect of the present disclosure. In some exemplifications, the data sources 2326 include, for example, the modular devices 2302 (which can include sensors configured to detect parameters associated with the patient and/or the modular device itself), databases 2322 (e.g., an EMR database containing patient records), and patient monitoring devices 2324 (e.g., a blood pressure (BP) monitor and an electrocardiography (EKG) monitor). The surgical hub 2304 can be configured to derive the contextual information pertaining to the surgical procedure from the data based upon, for example, the particular combination(s) of received data or the particular order in which the data is received from the data sources 2326. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 2304 to derive or infer information related to the surgical procedure from received data can be referred to as "situational awareness." In one exemplification, the surgical hub 2304 can incorporate a situational awareness system, which is the hardware and/or programming associated with the surgical hub 2304 that derives contextual information pertaining to the surgical procedure from the received data.

The situational awareness system of the surgical hub 2304 can be configured to derive the contextual information from the data received from the data sources 2326 in a variety of different ways. In one exemplification, the situational awareness system includes a pattern recognition system, or machine learning system (e.g., an artificial neural network), that has been trained on training data to correlate various inputs (e.g., data from databases 2322, patient monitoring devices 2324, and/or modular devices 2302) to corresponding contextual information regarding a surgical procedure. In other words, a machine learning system can be trained to accurately derive contextual information regarding a surgical procedure from the provided inputs. In another exemplification, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 2302. In one exemplification, the contextual information received by the situational awareness system of the surgical hub 2304 is associated with a particular control adjustment or set of control adjustments for one or more modular devices 2302. In another exemplification, the situational awareness system includes a further machine learning system, lookup table, or other such system, which generates or retrieves one or more control adjustments for one or more modular devices 2302 when provided the contextual information as input.

A surgical hub 2304 incorporating a situational awareness system provides a number of benefits for the surgical system 2300. One benefit includes improving the interpretation of sensed and collected data, which would in turn improve the processing accuracy and/or the usage of the data during the course of a surgical procedure. To return to a previous example, a situationally aware surgical hub 2304 could determine what type of tissue was being operated on; therefore, when an unexpectedly high force to close the surgical instrument's end effector is detected, the situationally aware surgical hub 2304 could correctly ramp up or ramp down the motor of the surgical instrument for the type of tissue.

As another example, the type of tissue being operated can affect the adjustments that are made to the compression rate and load thresholds of a surgical stapling and cutting instrument for a particular tissue gap measurement. A situationally aware surgical hub 2304 could infer whether a surgical procedure being performed is a thoracic or an abdominal procedure, allowing the surgical hub 2304 to determine whether the tissue clamped by an end effector of the surgical stapling and cutting instrument is lung (for a thoracic procedure) or stomach (for an abdominal procedure) tissue. The surgical hub 2304 could then adjust the compression rate and load thresholds of the surgical stapling and cutting instrument appropriately for the type of tissue.

As yet another example, the type of body cavity being operated in during an insufflation procedure can affect the function of a smoke evacuator. A situationally aware surgical hub 2304 could determine whether the surgical site is under pressure (by determining that the surgical procedure is utilizing insufflation) and determine the procedure type. As a procedure type is generally performed in a specific body cavity, the surgical hub 2304 could then control the motor rate of the smoke evacuator appropriately for the body cavity being operated in. Thus, a situationally aware surgical hub 2304 could provide a consistent amount of smoke evacuation for both thoracic and abdominal procedures.

As yet another example, the type of procedure being performed can affect the optimal energy level at which an ultrasonic surgical instrument or radio frequency (RF) electrosurgical instrument operates. Arthroscopic procedures, for example, require higher energy levels because the end effector of the ultrasonic surgical instrument or RF electrosurgical instrument is immersed in fluid. A situationally aware surgical hub 2304 could determine whether the surgical procedure is an arthroscopic procedure. The surgical hub 2304 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 2304 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 2304 can be configured to adjust the energy level for the ultrasonic surgical instrument or RF electrosurgical instrument throughout the course of a surgical procedure, rather than just on a procedure-by-procedure basis. A situationally aware surgical hub 2304 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

As yet another example, data can be drawn from additional data sources 2326 to improve the conclusions that the surgical hub 2304 draws from one data source 2326. A situationally aware surgical hub 2304 could augment data that it receives from the modular devices 2302 with contextual information that it has built up regarding the surgical procedure from other data sources 2326. For example, a situationally aware surgical hub 2304 can be configured to determine whether hemostasis has occurred (i.e., whether bleeding at a surgical site has stopped) according to video or image data received from a medical imaging device. However, in some cases the video or image data can be inconclusive. Therefore, in one exemplification, the surgical hub 2304 can be further configured to compare a physiologic measurement (e.g., blood pressure sensed by a BP monitor communicably connected to the surgical hub 2304) with the visual or image data of hemostasis (e.g., from a medical imaging device 124 (FIG. 2) communicably coupled to the surgical hub 2304) to make a determination on the integrity of the staple line or tissue weld. In other words, the situational awareness system of the surgical hub 2304 can consider the physiological measurement data to provide additional context in analyzing the visualization data. The additional context can be useful when the visualization data may be inconclusive or incomplete on its own.

Another benefit includes proactively and automatically controlling the paired modular devices 2302 according to the particular step of the surgical procedure that is being performed to reduce the number of times that medical personnel are required to interact with or control the surgical system 2300 during the course of a surgical procedure. For example, a situationally aware surgical hub 2304 could proactively activate the generator to which an RF electrosurgical instrument is connected if it determines that a subsequent step of the procedure requires the use of the instrument. Proactively activating the energy source allows the instrument to be ready for use a soon as the preceding step of the procedure is completed.

As another example, a situationally aware surgical hub 2304 could determine whether the current or subsequent step of the surgical procedure requires a different view or degree of magnification on the display according to the feature(s) at the surgical site that the surgeon is expected to need to view. The surgical hub 2304 could then proactively change the displayed view (supplied by, e.g., a medical imaging device for the visualization system 108) accordingly so that the display automatically adjusts throughout the surgical procedure.

As yet another example, a situationally aware surgical hub 2304 could determine which step of the surgical procedure is being performed or will subsequently be performed and whether particular data or comparisons between data will be required for that step of the surgical procedure. The surgical hub 2304 can be configured to automatically call up data screens based upon the step of the surgical procedure being performed, without waiting for the surgeon to ask for the particular information.

Another benefit includes checking for errors during the setup of the surgical procedure or during the course of the surgical procedure. For example, a situationally aware surgical hub 2304 could determine whether the operating theater is setup properly or optimally for the surgical procedure to be performed. The surgical hub 2304 can be configured to determine the type of surgical procedure being performed, retrieve the corresponding checklists, product location, or setup needs (e.g., from a memory), and then compare the current operating theater layout to the standard layout for the type of surgical procedure that the surgical hub 2304 determines is being performed. In one exemplification, the surgical hub 2304 can be configured to compare the list of items for the procedure (scanned by a scanner, for example) and/or a list of devices paired with the surgical hub 2304 to a recommended or anticipated manifest of items and/or devices for the given surgical procedure. If there are any discontinuities between the lists, the surgical hub 2304 can be configured to provide an alert indicating that a particular modular device 2302, patient monitoring device 2324, and/or other surgical item is missing. In one exemplification, the surgical hub 2304 can be configured to determine the relative distance or position of the modular devices 2302 and patient monitoring devices 2324 via proximity sensors, for example. The surgical hub 2304 can compare the relative positions of the devices to a recommended or anticipated layout for the particular surgical procedure. If there are any discontinuities between the layouts, the surgical hub 2304 can be configured to provide an alert indicating that the current layout for the surgical procedure deviates from the recommended layout.

As another example, a situationally aware surgical hub 2304 could determine whether the surgeon (or other medical personnel) was making an error or otherwise deviating from the expected course of action during the course of a surgical procedure. For example, the surgical hub 2304 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 2304 determined is being performed. In one exemplification, the surgical hub 2304 can be configured to provide an alert indicating that an unexpected action is being performed or an unexpected device is being utilized at the particular step in the surgical procedure.

Overall, the situational awareness system for the surgical hub 2304 improves surgical procedure outcomes by adjusting the surgical instruments (and other modular devices 2302) for the particular context of each surgical procedure (such as adjusting to different tissue types) and validating actions during a surgical procedure. The situational awareness system also improves surgeons' efficiency in performing surgical procedures by automatically suggesting next steps, providing data, and adjusting displays and other modular devices 2302 in the surgical theater according to the specific context of the procedure.

Modular Energy System

ORs everywhere in the world are a tangled web of cords, devices, and people due to the amount of equipment required to perform surgical procedures. Surgical capital equipment tends to be a major contributor to this issue because most surgical capital equipment performs a single, specialized task. Due to their specialized nature and the surgeons' needs to utilize multiple different types of devices during the course of a single surgical procedure, an OR may be forced to be stocked with two or even more pieces of surgical capital equipment, such as energy generators. Each of these pieces of surgical capital equipment must be individually plugged into a power source and may be connected to one or more other devices that are being passed between OR personnel, creating a tangle of cords that must be navigated. Another issue faced in modern ORs is that each of these specialized pieces of surgical capital equipment has its own user interface and must be independently controlled from the other pieces of equipment within the OR. This creates complexity in properly controlling multiple different devices in connection with each other and forces users to be trained on and memorize different types of user interfaces (which may further change based upon the task or surgical procedure being performed, in addition to changing between each piece of capital equipment). This cumbersome, complex process can necessitate the need for even more individuals to be present within the OR and can create danger if multiple devices are not properly controlled in tandem with each other. Therefore, consolidating surgical capital equipment technology into singular systems that are able to flexibly address surgeons' needs to reduce the footprint of surgical capital equipment within ORs would simplify the user experience, reduce the amount of clutter in ORs, and prevent difficulties and dangers associated with simultaneously controlling multiple pieces of capital equipment. Further, making such systems expandable or customizable would allow for new technology to be conveniently incorporated into existing surgical systems, obviating the need to replace entire surgical systems or for OR personnel to learn new user interfaces or equipment controls with each new technology.

As described in FIGS. 1-3, a surgical hub 106 can be configured to interchangeably receive a variety of modules, which can in turn interface with surgical devices (e.g., a surgical instrument or a smoke evacuator) or provide various other functions (e.g., communications). In one aspect, a surgical hub 106 can be embodied as a modular energy system 2000, which is illustrated in connection with FIGS. 6-12. The modular energy system 2000 can include a variety of different modules 2001 that are connectable together in a stacked configuration. In one aspect, the modules 2001 can be both physically and communicably coupled together when stacked or otherwise connected together into a singular assembly. Further, the modules 2001 can be interchangeably connectable together in different combinations or arrangements. In one aspect, each of the modules 2001 can include a consistent or universal array of connectors disposed along their upper and lower surfaces, thereby allowing any module 2001 to be connected to another module 2001 in any arrangement (except that, in some aspects, a particular module type, such as the header module 2002, can be configured to serve as the uppermost module within the stack, for example). In an alternative aspect, the modular energy system 2000 can include a housing that is configured to receive and retain the modules 2001, as is shown in FIG. 3. The modular energy system 2000 can also include a variety of different components or accessories that are also connectable to or otherwise associatable with the modules 2001. In another aspect, the modular energy system 2000 can be embodied as a generator module 140 (FIG. 3) of a surgical hub 106. In yet another aspect, the modular energy system 2000 can be a distinct system from a surgical hub 106. In such aspects, the modular energy system 2000 can be communicably couplable to a surgical hub 206 for transmitting and/or receiving data therebetween.

Figure 6:
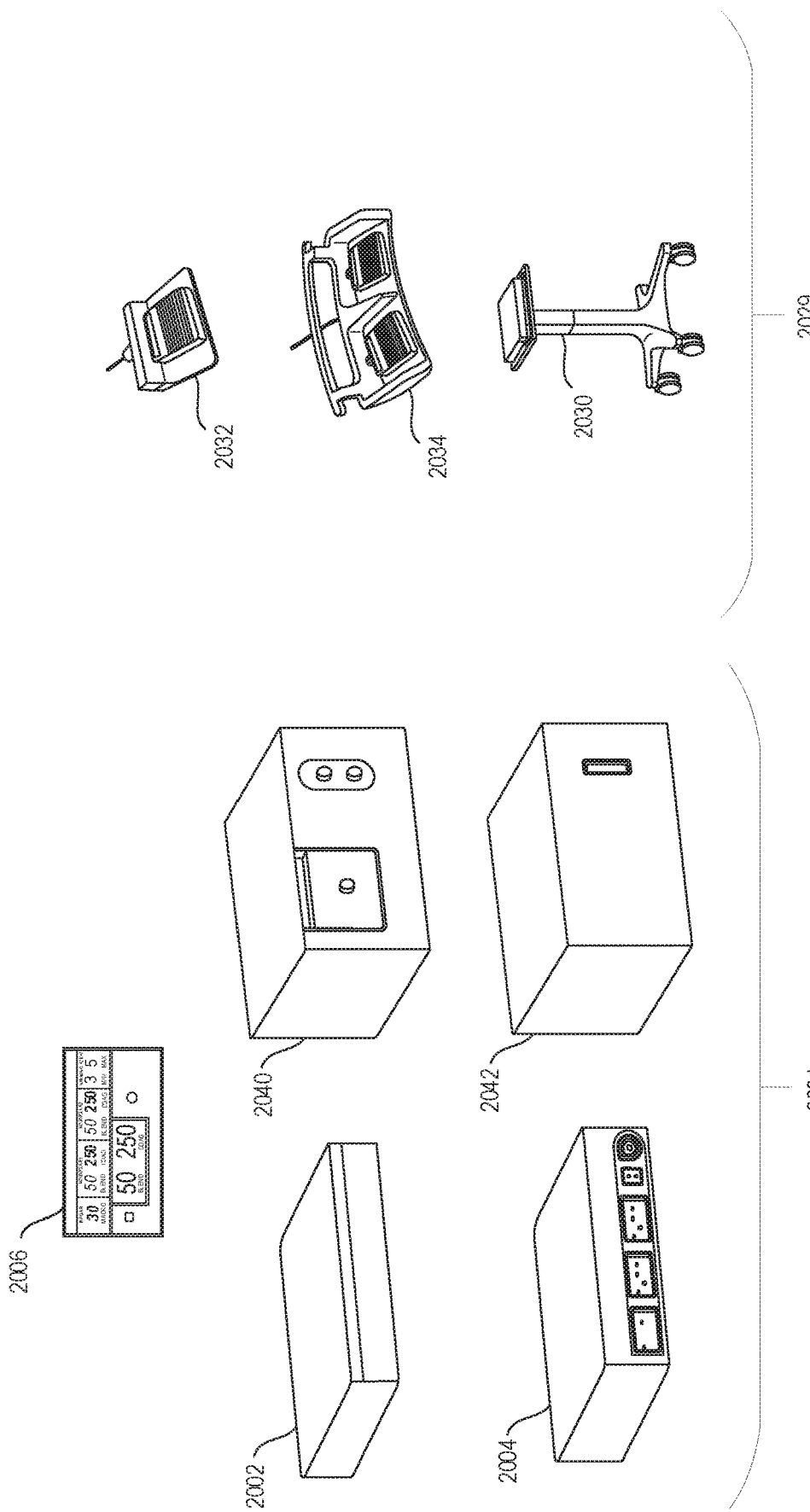
FIG. 6 is a diagram of various modules and other components that are combinable to customize modular energy systems, in accordance with at least one aspect of the present disclosure.

The modular energy system 2000 can be assembled from a variety of different modules 2001, some examples of which are illustrated in FIG. 6. Each of the different types of modules 2001 can provide different functionality, thereby allowing the modular energy system 2000 to be assembled into different configurations to customize the functions and capabilities of the modular energy system 2000 by customizing the modules 2001 that are included in each modular energy system 2000. The modules 2001 of the modular energy system 2000 can include, for example, a header module 2002 (which can include a display screen 2006), an energy module 2004, a technology module 2040, and a visualization module 2042. In the depicted aspect, the header module 2002 is configured to serve as the top or uppermost module within the modular energy system stack and can thus lack connectors along its top surface. In another aspect, the header module 2002 can be configured to be positioned at the bottom or the lowermost module within the modular energy system stack and can thus lack connectors along its bottom surface. In yet another aspect, the header module 2002 can be configured to be positioned at an intermediate position within the modular energy system stack and can thus include connectors along both its bottom and top surfaces. The header module 2002 can be configured to control the system-wide settings of each module 2001 and component connected thereto through physical controls 2011 thereon and/or a graphical user interface (GUI) 2008 rendered on the display screen 2006. Such settings could include the activation of the modular energy system 2000, the volume of alerts, the footswitch settings, the settings icons, the appearance or configuration of the user interface, the surgeon profile logged into the modular energy system 2000, and/or the type of surgical procedure being performed. The header module 2002 can also be configured to provide communications, processing, and/or power for the modules 2001 that are connected to the header module 2002. The energy module 2004, which can also be referred to as a generator module 140 (FIG. 3), can be configured to generate one or multiple energy modalities for driving electrosurgical and/or ultrasonic surgical instruments connected thereto. The technology module 2040 can be configured to provide additional or expanded control algorithms (e.g., electrosurgical or ultrasonic control algorithms for controlling the energy output of the energy module 2004). The visualization module 2042 can be configured to interface with visualization devices (i.e., scopes) and accordingly provide increased visualization capabilities.

The modular energy system 2000 can further include a variety of accessories 2029 that are connectable to the modules 2001 for controlling the functions thereof or that are otherwise configured to work on conjunction with the modular energy system 2000. The accessories 2029 can include, for example, a single-pedal footswitch 2032, a dual-pedal footswitch 2034, and a cart 2030 for supporting the modular energy system 2000 thereon. The footswitches 2032, 2034 can be configured to control the activation or function of particular energy modalities output by the energy module 2004, for example.

By utilizing modular components, the depicted modular energy system 2000 provides a surgical platform that grows with the availability of technology and is customizable to the needs of the facility and/or surgeons. Further, the modular energy system 2000 supports combo devices (e.g., dual electrosurgical and ultrasonic energy generators) and supports software-driven algorithms for customized tissue effects. Still further, the surgical system architecture reduces the capital footprint by combining multiple technologies critical for surgery into a single system.

The various modular components utilizable in connection with the modular energy system 2000 can include monopolar energy generators, bipolar energy generators, dual electrosurgical/ultrasonic energy generators, display screens, and various other modules and/or other components, some of which are also described above in connection with FIGS. 1-3.

Figure 7B:
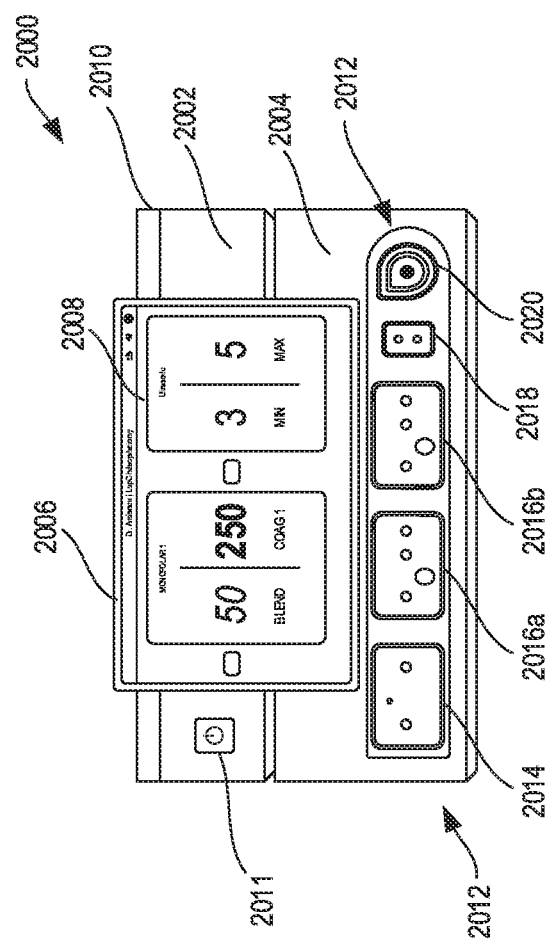
FIG. 7B is the modular energy system shown in FIG. 7A mounted to a cart, in accordance with at least one aspect of the present disclosure.
Figure 7A:
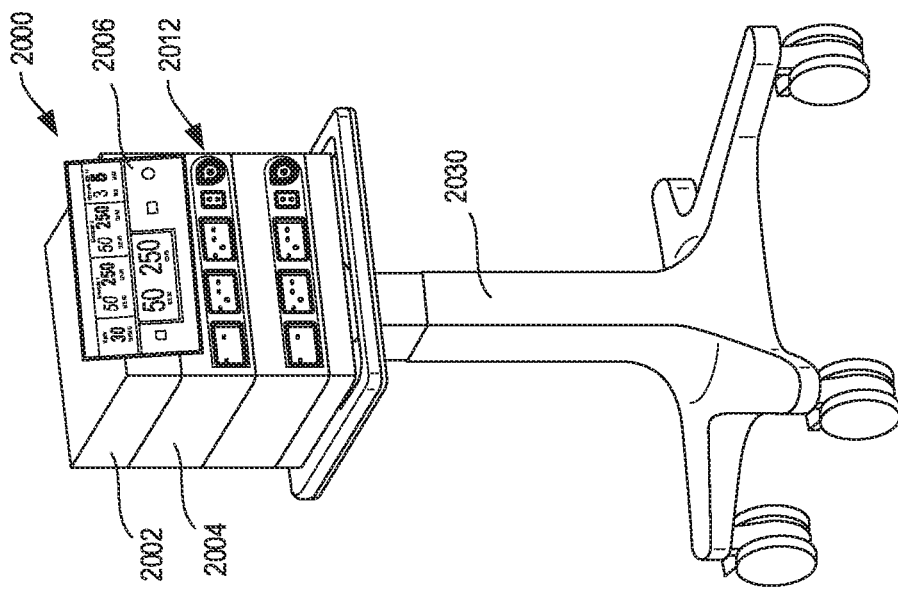
FIG. 7A is a first illustrative modular energy system configuration including a header module and a display screen that renders a graphical user interface (GUI) for relaying information regarding modules connected to the header module, in accordance with at least one aspect of the present disclosure.
Figure 11:
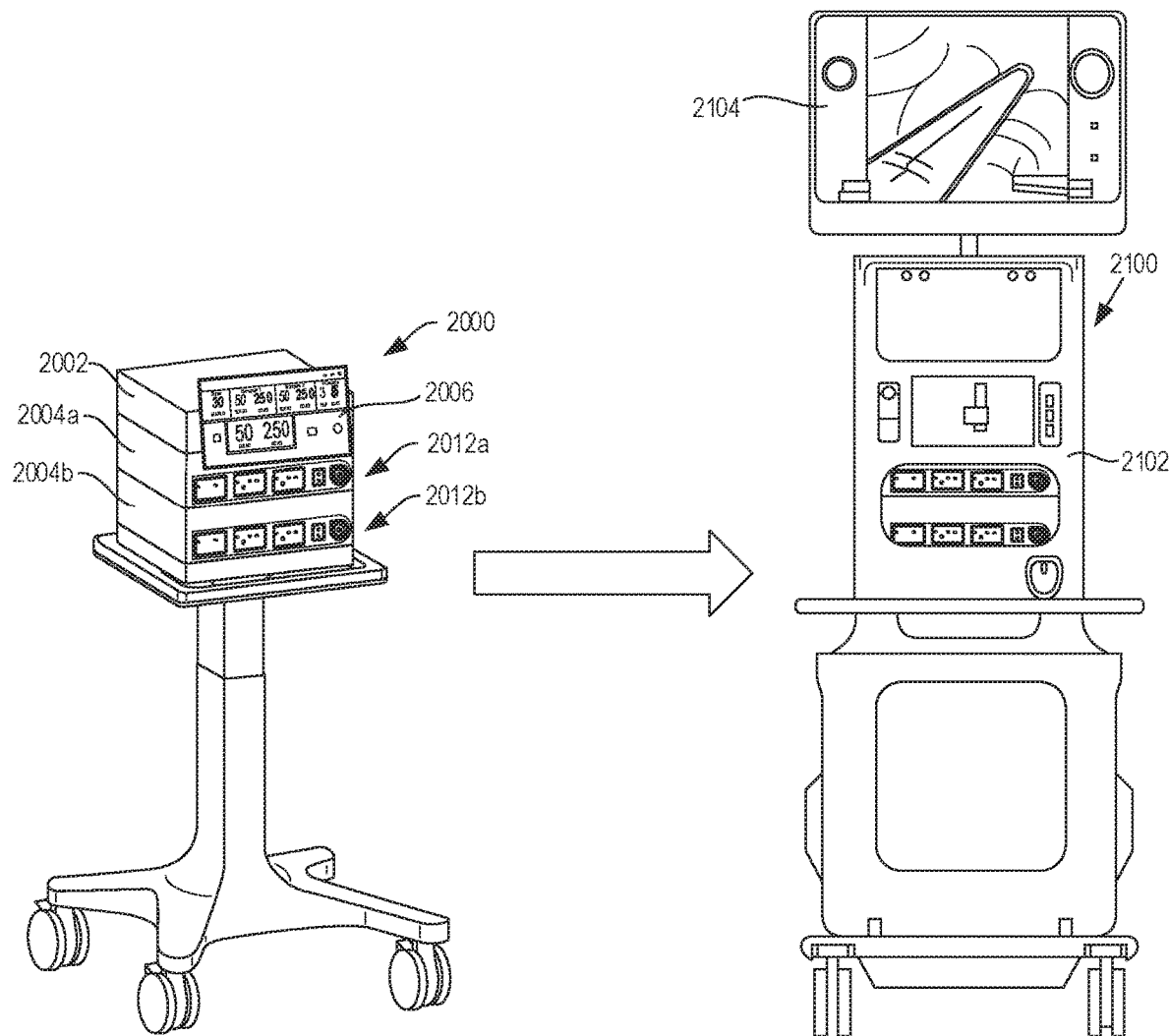
FIG. 11 is a diagram of a modular energy system including communicably connectable surgical platforms, in accordance with at least one aspect of the present disclosure.

Referring now to FIG. 7A, the header module 2002 can, in some aspects, include a display screen 2006 that renders a GUI 2008 for relaying information regarding the modules 2001 connected to the header module 2002. In some aspects, the GUI 2008 of the display screen 2006 can provide a consolidated point of control of all of the modules 2001 making up the particular configuration of the modular energy system 2000. Various aspects of the GUI 2008 are discussed in fuller detail below in connection with FIG. 12. In alternative aspects, the header module 2002 can lack the display screen 2006 or the display screen 2006 can be detachably connected to the housing 2010 of the header module 2002. In such aspects, the header module 2002 can be communicably couplable to an external system that is configured to display the information generated by the modules 2001 of the modular energy system 2000. For example, in robotic surgical applications, the modular energy system 2000 can be communicably couplable to a robotic cart or robotic control console, which is configured to display the information generated by the modular energy system 2000 to the operator of the robotic surgical system. As another example, the modular energy system 2000 can be communicably couplable to a mobile display that can be carried or secured to a surgical staff member for viewing thereby. In yet another example, the modular energy system 2000 can be communicably couplable to a surgical hub 2100 or another computer system that can include a display 2104, as is illustrated in FIG. 11. In aspects utilizing a user interface that is separate from or otherwise distinct from the modular energy system 2000, the user interface can be wirelessly connectable with the modular energy system 2000 as a whole or one or more modules 2001 thereof such that the user interface can display information from the connected modules 2001 thereon.

Referring still to FIG. 7A, the energy module 2004 can include a port assembly 2012 including a number of different ports configured to deliver different energy modalities to corresponding surgical instruments that are connectable thereto. In the particular aspect illustrated in FIGS. 6-12, the port assembly 2012 includes a bipolar port 2014, a first monopolar port 2016a, a second monopolar port 2016b, a neutral electrode port 2018 (to which a monopolar return pad is connectable), and a combination energy port 2020. However, this particular combination of ports is simply provided for illustrative purposes and alternative combinations of ports and/or energy modalities may be possible for the port assembly 2012.

As noted above, the modular energy system 2000 can be assembled into different configurations. Further, the different configurations of the modular energy system 2000 can also be utilizable for different surgical procedure types and/or different tasks. For example, FIGS. 7A and 7B illustrate a first illustrative configuration of the modular energy system 2000 including a header module 2002 (including a display screen 2006) and an energy module 2004 connected together. Such a configuration can be suitable for laparoscopic and open surgical procedures, for example.

Figure 8A:
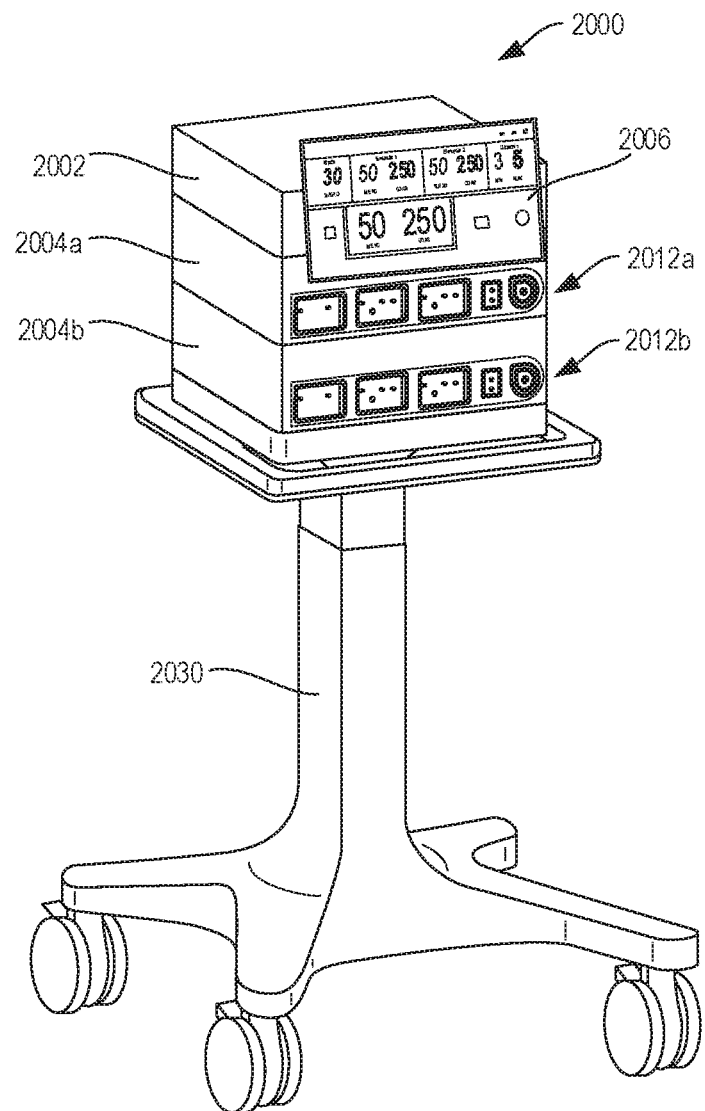
FIG. 8A is a second illustrative modular energy system configuration including a header module, a display screen, an energy module, and an expanded energy module connected together and mounted to a cart, in accordance with at least one aspect of the present disclosure.
Figure 8B:
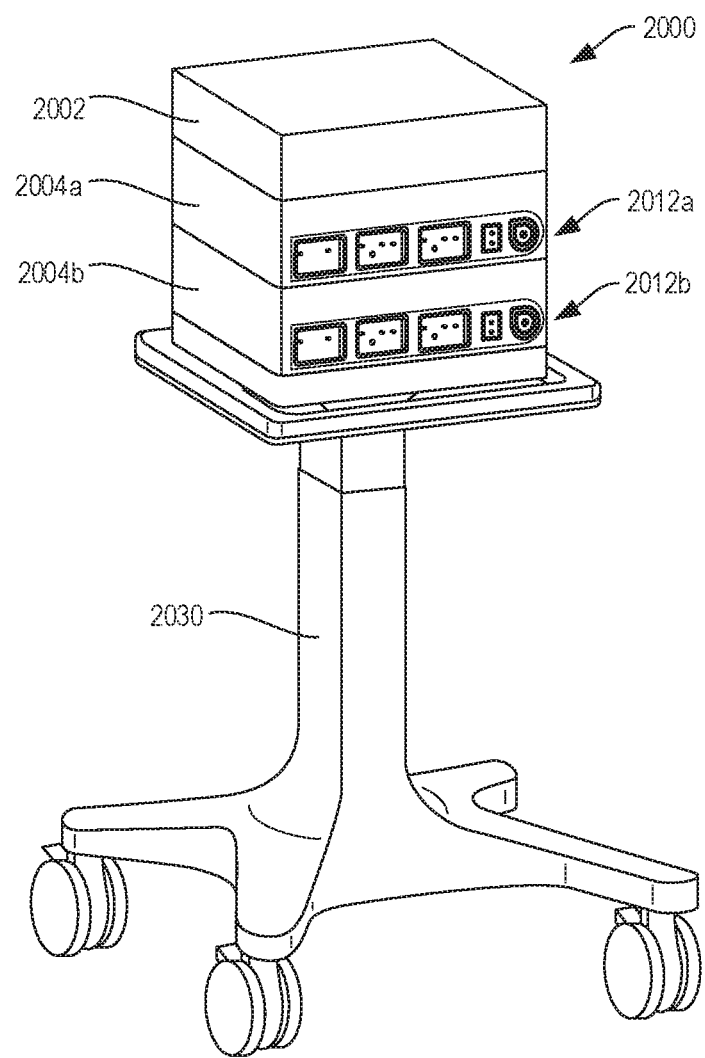
FIG. 8B is a third illustrative modular energy system configuration that is similar to the second configuration shown in FIG. 7A, except that the header module lacks a display screen, in accordance with at least one aspect of the present disclosure.

FIG. 8A illustrates a second illustrative configuration of the modular energy system 2000 including a header module 2002 (including a display screen 2006), a first energy module 2004a, and a second energy module 2004b connected together. By stacking two energy modules 2004a, 2004b, the modular energy system 2000 can provide a pair of port assemblies 2012a, 2012b for expanding the array of energy modalities deliverable by the modular energy system 2000 from the first configuration. The second configuration of the modular energy system 2000 can accordingly accommodate more than one bipolar/monopolar electrosurgical instrument, more than two bipolar/monopolar electrosurgical instruments, and so on. Such a configuration can be suitable for particularly complex laparoscopic and open surgical procedures. FIG. 8B illustrates a third illustrative configuration that is similar to the second configuration, except that the header module 2002 lacks a display screen

2006. This configuration can be suitable for robotic surgical applications or mobile display applications, as noted above.

Figure 9:
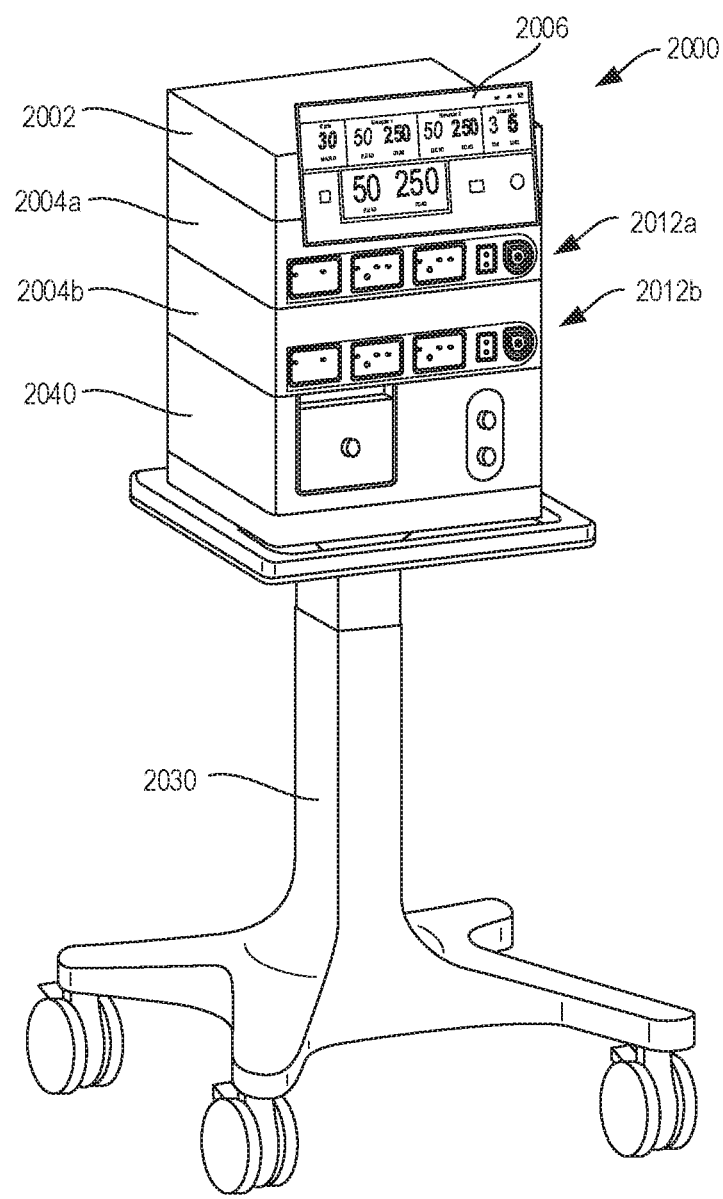
FIG. 9 is a fourth illustrative modular energy system configuration including a header module, a display screen, an energy module, ae expanded energy module, and a technology module connected together and mounted to a cart, in accordance with at least one aspect of the present disclosure.

FIG. 9 illustrates a fourth illustrative configuration of the modular energy system 2000 including a header module 2002 (including a display screen 2006), a first energy module 2004a, a second energy module 2004b, and a technology module 2040 connected together. Such a configuration can be suitable for surgical applications where particularly complex or computation-intensive control algorithms are required. Alternatively, the technology module 2040 can be a newly released module that supplements or expands the capabilities of previously released modules (such as the energy module 2004).

Figure 10:
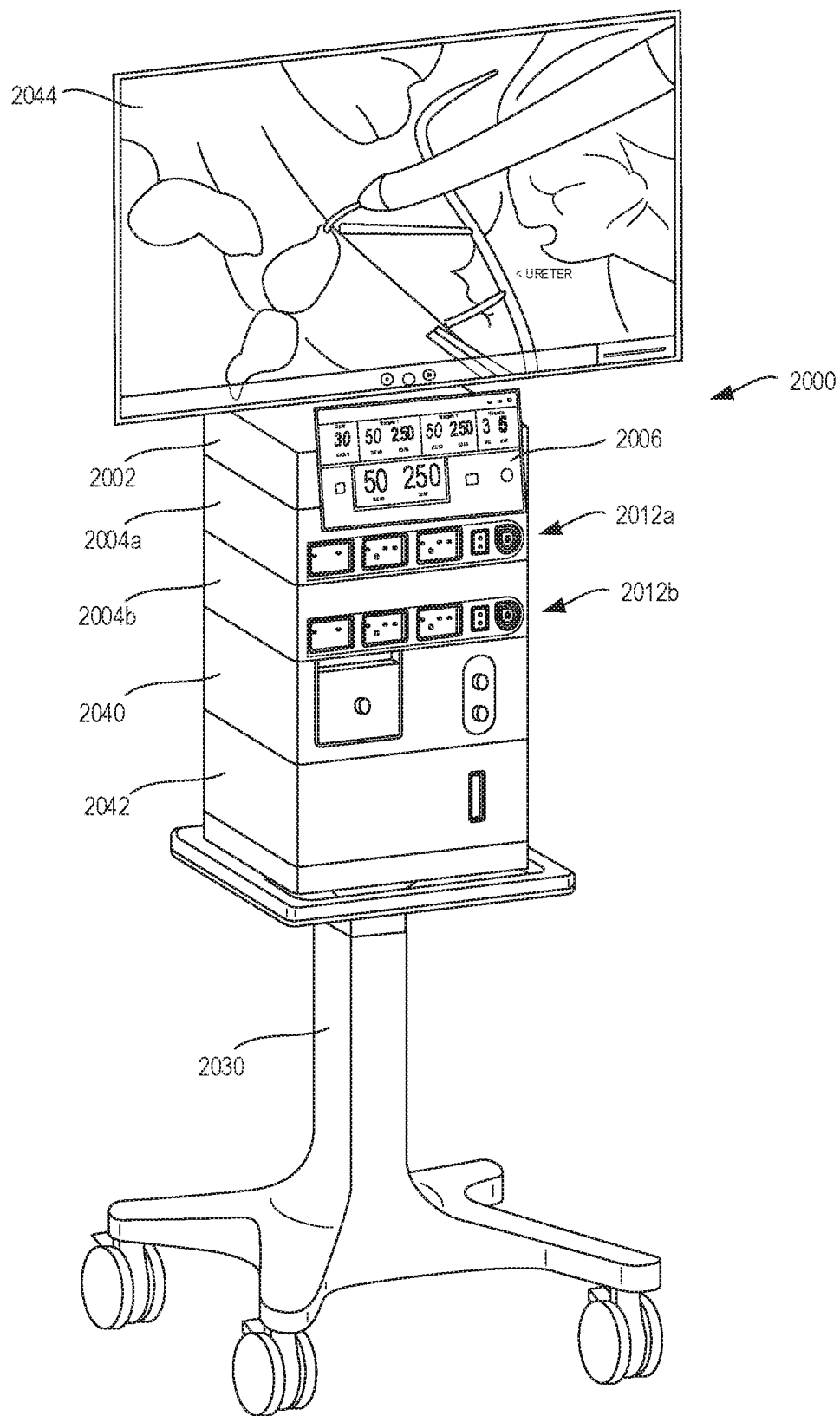
FIG. 10 is a fifth illustrative modular energy system configuration including a header module, a display screen, an energy module, an expanded energy module, a technology module, and a visualization module connected together and mounted to a cart, in accordance with at least one aspect of the present disclosure.

FIG. 10 illustrates a fifth illustrative configuration of the modular energy system 2000 including a header module 2002 (including a display screen 2006), a first energy module 2004a, a second energy module 2004b, a technology module 2040, and a visualization module 2042 connected together. Such a configuration can be suitable for endoscopic procedures by providing a dedicated surgical display 2044 for relaying the video feed from the scope coupled to the visualization module 2042. It should be noted that the configurations illustrated in FIGS. 7A-11 and described above are provided simply to illustrate the various concepts of the modular energy system 2000 and should not be interpreted to limit the modular energy system 2000 to the particular aforementioned configurations.

As noted above, the modular energy system 2000 can be communicably couplable to an external system, such as a surgical hub 2100 as illustrated in FIG. 11. Such external systems can include a display screen 2104 for displaying a visual feed from an endoscope (or a camera or another such visualization device) and/or data from the modular energy system 2000. Such external systems can also include a computer system 2102 for performing calculations or otherwise analyzing data generated or provided by the modular energy system 2000, controlling the functions or modes of the modular energy system 2000, and/or relaying data to a cloud computing system or another computer system. Such external systems could also coordinate actions between multiple modular energy systems 2000 and/or other surgical systems (e.g., a visualization system 108 and/or a robotic system 110 as described in connection with FIGS. 1 and 2).

Figure 12:
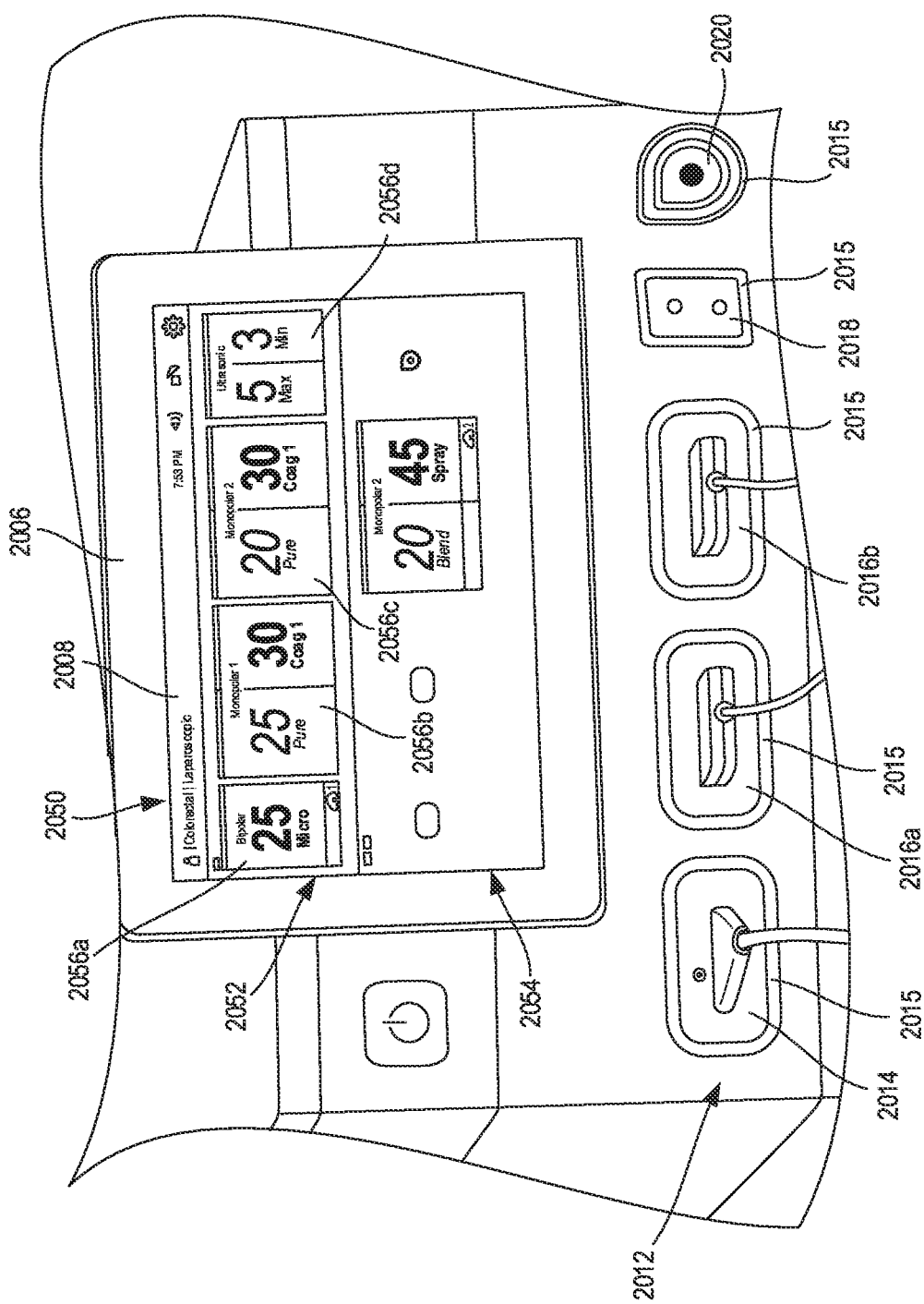
FIG. 12 is a perspective view of a header module of a modular energy system including a user interface, in accordance with at least one aspect of the present disclosure.

Referring now to FIG. 12, in some aspects, the header module 2002 can include or support a display 2006 configured for displaying a GUI 2008, as noted above. The display screen 2006 can include a touchscreen for receiving input from users in addition to displaying information. The controls displayed on the GUI 2008 can correspond to the module(s) 2001 that are connected to the header module 2002. In some aspects, different portions or areas of the GUI 2008 can correspond to particular modules 2001. For example, a first portion or area of the GUI 2008 can correspond to a first module and a second portion or area of the GUI 2008 can correspond to a second module. As different and/or additional modules 2001 are connected to the modular energy system stack, the GUI 2008 can adjust to accommodate the different and/or additional controls for each newly added module 2001 or remove controls for each module 2001 that is removed. Each portion of the display corresponding to a particular module connected to the header module 2002 can display controls, data, user prompts, and/or other information corresponding to that module. For example, in FIG. 12, a first or upper portion 2052 of the depicted GUI 2008 displays controls and data associated with an energy module 2004 that is connected to the header module 2002. In particular, the first portion 2052 of the GUI 2008 for the energy module 2004 provides first widget 2056a corresponding to the bipolar port 2014, a second widget 2056b corresponding to the first monopolar port 2016a, a third widget 2056c corresponding to the second monopolar port 2016b, and a fourth widget 2056d corresponding to the combination energy port 2020. Each of these widgets 2056a-d provides data related to its corresponding port of the port assembly 2012 and controls for controlling the modes and other features of the energy modality delivered by the energy module 2004 through the respective port of the port assembly 2012. For example, the widgets 2056a—d can be configured to display the power level of the surgical instrument connected to the respective port, change the operational mode of the surgical instrument connected to the respective port (e.g., change a surgical instrument from a first power level to a second power level and/or change a monopolar surgical instrument from a "spray" mode to a "blend" mode), and so on.

In one aspect, the header module 2002 can include various physical controls 2011 in addition to or in lieu of the GUI 2008. Such physical controls 2011 can include, for example, a power button that controls the application of power to each module 2001 that is connected to the header module 2002 in the modular energy system 2000. Alternatively, the power button can be displayed as part of the GUI 2008. Therefore, the header module 2002 can serve as a single point of contact and obviate the need to individually activate and deactivate each individual module 2001 from which the modular energy system 2000 is constructed.

In one aspect, the header module 2002 can display still images, videos, animations, and/or information associated with the surgical modules 2001 of which the modular energy system 2000 is constructed or the surgical devices that are communicably coupled to the modular energy system 2000. The still images and/or videos displayed by the header module 2002 can be received from an endoscope or another visualization device that is communicably coupled to the modular energy system 2000. The animations and/or information of the GUI 2008 can be overlaid on or displayed adjacent to the images or video feed.

In one aspect, the modules 2001 other than the header module 2002 can be configured to likewise relay information to users. For example, the energy module 2004 can include light assemblies 2015 disposed about each of the ports of the port assembly 2012. The light assemblies 2015 can be configured to relay information to the user regarding the port according to their color or state (e.g., flashing). For example, the light assemblies 2015 can change from a first color to a second color when a plug is fully seated within the respective port. In one aspect, the color or state of the light assemblies 2015 can be controlled by the header module 2002. For example, the header module 2002 can cause the light assembly 2015 of each port to display a color corresponding to the color display for the port on the GUI 2008.

Figure 13:
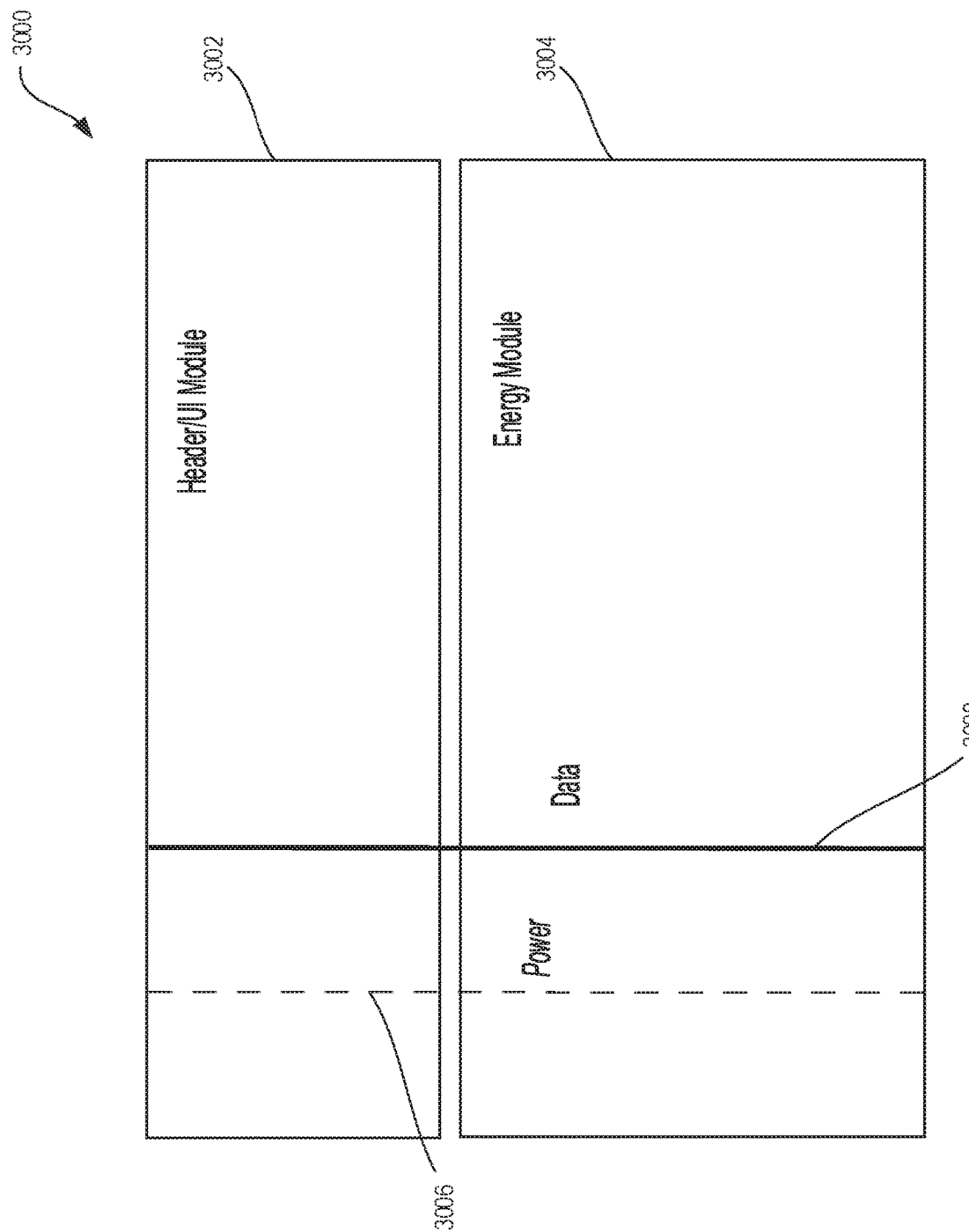
FIG. 13 is a block diagram of a stand-alone hub configuration of a modular energy system, in accordance with at least one aspect of the present disclosure.
Figure 14:
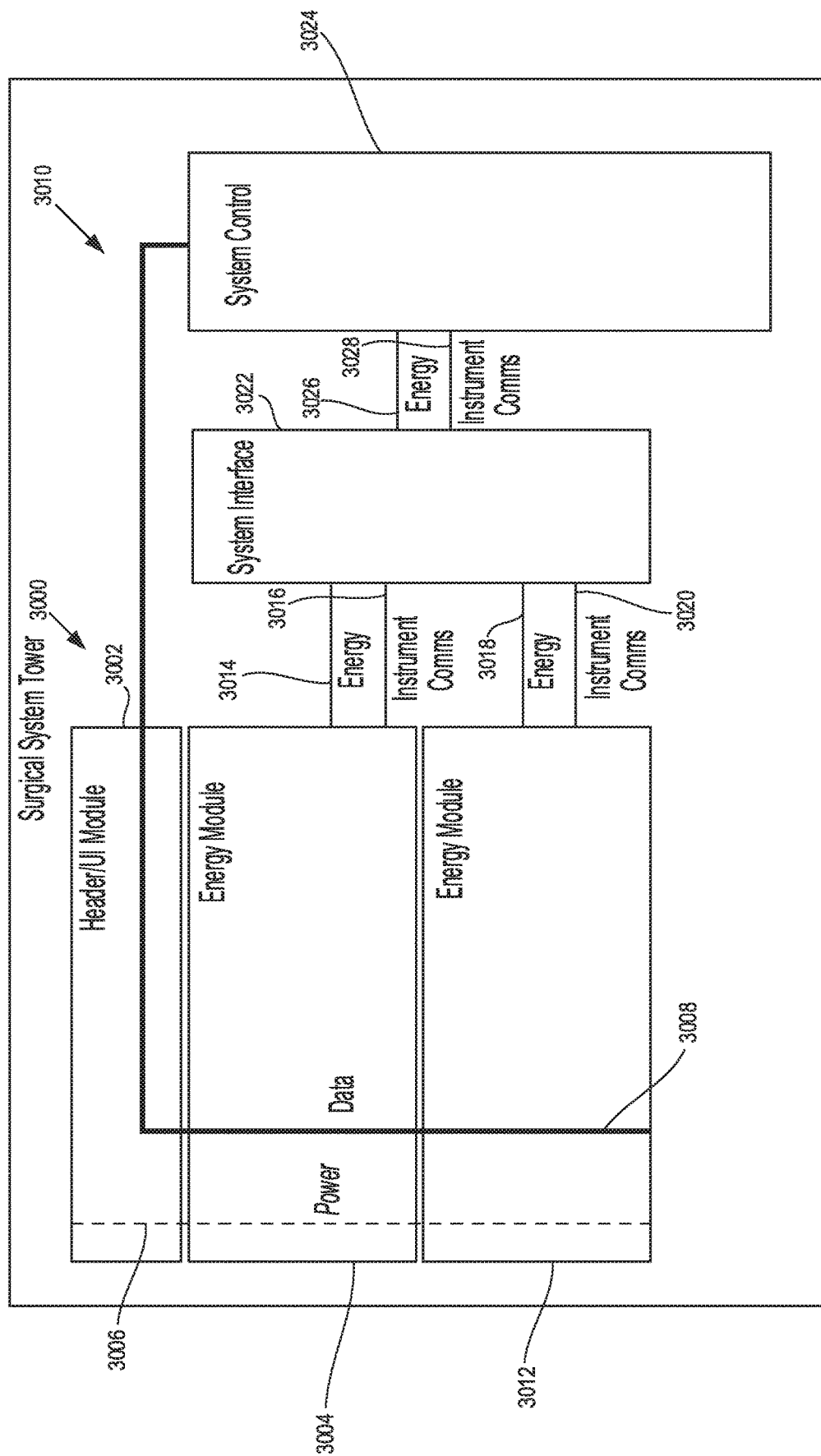
FIG. 14 is a block diagram of a hub configuration of a modular energy system integrated with a surgical control system, in accordance with at least one aspect of the present disclosure.

FIG. 13 is a block diagram of a stand-alone hub configuration of a modular energy system 3000, in accordance with at least one aspect of the present disclosure and FIG. 14 is a block diagram of a hub configuration of a modular energy system 3000 integrated with a surgical control system 3010, in accordance with at least one aspect of the present disclosure. As depicted in FIGS. 13 and 14, the modular energy system 3000 can be either utilized as stand-alone units or integrated with a surgical control system 3010 that controls and/or receives data from one or more surgical hub units. In the examples illustrated in FIGS. 13 and 14, the integrated header/UI module 3002 of the modular energy system 3000 includes a header module and a UI module integrated together as a singular module. In other aspects, the header module and the UI module can be provided as separate components that are communicatively coupled though a data bus 3008.

As illustrated in FIG. 13, an example of a stand-alone modular energy system 3000 includes an integrated header module/user interface (UI) module 3002 coupled to an energy module 3004. Power and data are transmitted between the integrated header/UI module 3002 and the energy module 3004 through a power interface 3006 and a data interface 3008. For example, the integrated header/UI module 3002 can transmit various commands to the energy module 3004 through the data interface 3008. Such commands can be based on user inputs from the UI. As a further example, power may be transmitted to the energy module 3004 through the power interface 3006.

In FIG. 14, a surgical hub configuration includes a modular energy system 3000 integrated with a control system 3010 and an interface system 3022 for managing, among other things, data and power transmission to and/or from the modular energy system 3000. The modular energy system depicted in FIG. 14 includes an integrated header module/UI module 3002, a first energy module 3004, and a second energy module 3012. In one example, a data transmission pathway is established between the system control unit 3024 of the control system 3010 and the second energy module 3012 through the first energy module 3004 and the header/UI module 3002 through a data interface 3008. In addition, a power pathway extends between the integrated header/UI module 3002 and the second energy module 3012 through the first energy module 3004 through a power interface 3006. In other words, in one aspect, the first energy module 3004 is configured to function as a power and data interface between the second energy module 3012 and the integrated header/UI module 3002 through the power interface 3006 and the data interface 3008. This arrangement allows the modular energy system 3000 to expand by seamlessly connecting additional energy modules to energy modules 3004, 3012 that are already connected to the integrated header/UI module 3002 without the need for dedicated power and energy interfaces within the integrated header/UI module 3002.

The system control unit 3024, which may be referred to herein as a control circuit, control logic, microprocessor, microcontroller, logic, or FPGA, or various combinations thereof, is coupled to the system interface 3022 via energy interface 3026 and instrument communication interface 3028. The system interface 3022 is coupled to the first energy module 3004 via a first energy interface 3014 and a first instrument communication interface 3016. The system interface 3022 is coupled to the second energy module 3012 via a second energy interface 3018 and a second instrument communication interface 3020. As additional modules, such as additional energy modules, are stacked in the modular energy system 3000, additional energy and communications interfaces are provided between the system interface 3022 and the additional modules.

The energy modules 3004, 3012 are connectable to a hub and can be configured to generate electrosurgical energy (e.g., bipolar or monopolar), ultrasonic energy, or a combination thereof (referred to herein as an "advanced energy" module) for a variety of energy surgical instruments. Generally, the energy modules 3004, 3012 include hardware/software interfaces, an ultrasonic controller, an advanced energy RF controller, bipolar RF controller, and control algorithms executed by the controller that receives outputs from the controller and controls the operation of the various energy modules 3004, 3012 accordingly. In various aspects of the present disclosure, the controllers described herein may be implemented as a control circuit, control logic, microprocessor, microcontroller, logic, or FPGA, or various combinations thereof.

In one aspect, with reference to FIGS. 13 and 14, the modules of the modular energy system 3000 can include an optical link allowing high speed communication (10-50 Mb/s) across the patient isolation boundary. This link would carry device communications, mitigation signals (watchdog, etc.), and low bandwidth run-time data. In some aspects, the optical link(s) will not contain real-time sampled data, which can be done on the non-isolated side.

In one aspect, with reference to FIGS. 13 and 14, the modules of the modular energy system 3000 can include a multi-function circuit block which can: (i) read presence resistor values via A/D and current source, (ii) communicate with legacy instruments via hand switch Q protocols, (iii) communicate with instruments via local bus 1-Wire protocols, and (iv) communicate with CAN FD-enabled surgical instruments. When a surgical instrument is properly identified by an energy generator module, the relevant pin functions and communications circuits are enabled, while the other unused functions are disabled or disconnected, and set to a high impedance state.

In one aspect, with reference to FIGS. 13 and 14, the modules of the modular energy system 3000 can include a pulse/stimulation/auxiliary amplifier. This is a flexible-use amplifier based on a full-bridge output and incorporates functional isolation. This allows its differential output to be referenced to any output connection on the applied part (except, in some aspects, a monopolar active electrode). The amplifier output can be either small signal linear (pulse/stim) with waveform drive provided by a DAC or a square wave drive at moderate output power for DC applications such as DC motors, illumination, FET drive, etc. The output voltage and current are sensed with functionally isolated voltage and current feedback to provide accurate impedance and power measurements to the FPGA. Paired with a CAN FD-enabled instrument, this output can offer motor/motion control drive, while position or velocity feedback is provided by the CAN FD interface for closed loop control.

As described in greater detail herein, a modular energy system comprises a header module and one or more functional or surgical modules. In various instances, the modular energy system is a modular energy system. In various instances, the surgical modules include energy modules, communication modules, user interface modules; however, the surgical modules are envisioned to be any suitable type of functional or surgical module for use with the modular energy system.

Figure 15:
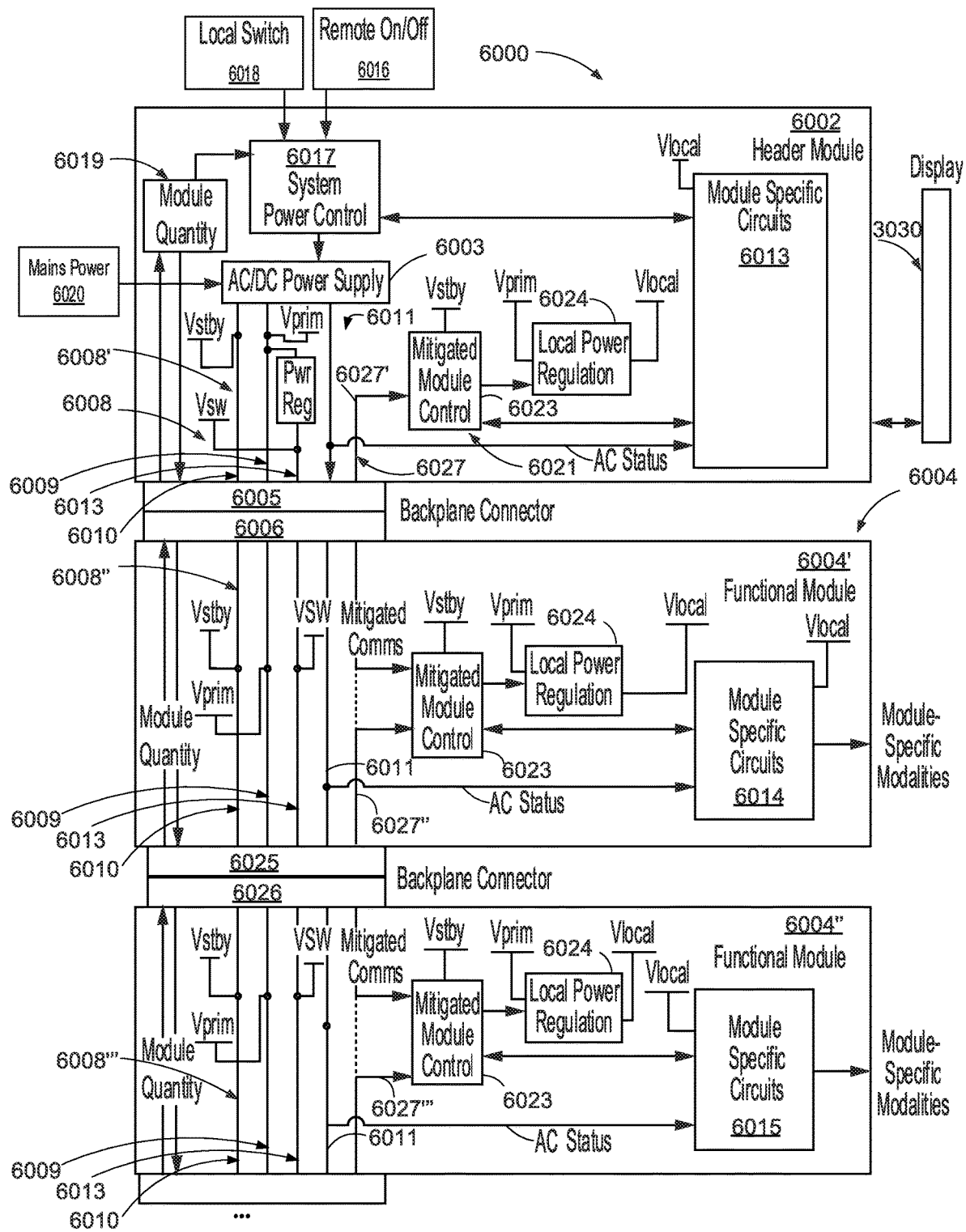
FIG. 15 is a schematic diagram of a modular energy system stack illustrating a power backplane, in accordance with at least one aspect of the present disclosure.

Modular energy system offers many advantages in a surgical procedure, as described above in connection with the modular energy systems 2000 (FIGS. 6-12), 3000 (FIGS. 13-15). However, cable management and setup/teardown time can be a significant deterrent. Various aspects of the present disclosure provide a modular energy system with a single power cable and a single power switch to control startup and shutdown of the entire modular energy system, which obviated the need to individually activate and deactivate each individual module from which the modular energy system is constructed. Also, various aspects of the present disclosure provide a modular energy system with power management schemes that facilitate a safe and, in some instances, concurrent delivery of power to the modules of a modular energy system.

In various aspects, as illustrated in FIG. 15, a modular energy system 6000 that is similar in many respects to the modular energy systems 2000 (FIGS. 6-12), 3000 (FIGS. 13-15). For the sake of brevity, various details of the modular energy system 6000, which are similar to the modular energy system 2000 and/or the modular energy system 3000, are not repeated herein.

The modular energy system 6000 comprises a header module 6002 and an "N" number of surgical modules 6004, where "N" is an integer greater than or equal to one. In various examples, the modular energy system 6000 includes a UI module such as, for example, the UI module 3030 and/or a communication module such as, for example, the communication module 3032. Furthermore, pass-through hub connectors couple individual modules to one another in a stack configuration. In the example of FIG. 15, the header module 6002 is coupled to a surgical module 6004 via pass-through hub connectors 6005, 6006.

The modular energy system 6000 comprises an example power architecture that consists of a single AC/DC power supply 6003 that provides power to all the surgical modules in the stack. The AC/DC power supply 6003 is housed in the header module 6002, and utilizes a power backplane 6008 to distribute power to each module in the stack. The example of FIG. 15 demonstrates three separate power domains on the power backplane 6008: a primary power domain 6009, a standby power domain 6010, and an Ethernet switch power domain 6013.

In the example illustrated in FIG. 15, the power backplane 6008 extends from the header module 6002 through a number of intermediate modules 6004 to a most bottom, or farthest, module in the stack. In various aspects, the power backplane 6008 is configured to deliver power to a surgical module 6004 through one or more other surgical modules 6004 that are ahead of it in the stack. The surgical module 6004 receiving power from the header module 6002 can be coupled to a surgical instrument or tool configured to deliver therapeutic energy to a patient.

The primary power domain 6009 is the primary power source for the functional module-specific circuits 6013, 6014, 6015 of the modules 6002, 6004. It consists of a single voltage rail that is provided to every module. In at least one example, a nominal voltage of 60V can be selected to be higher than the local rails needed by any module, so that the modules can exclusively implement buck regulation, which is generally more efficient than boost regulation.

In various aspects, the primary power domain 6009 is controlled by the header module 6002. In certain instances, as illustrated in FIG. 15, a local power switch 6018 is positioned on the header module 6002. In certain instances, a remote on/off interface 6016 can be configured to control a system power control 6017 on the header module 6002, for example. In at least one example, the remote on/off interface 6016 is configured to transmit pulsed discrete commands (separate commands for On and Off) and a power status telemetry signal. In various instances, the primary power domain 6009 is configured to distribute power to all the modules in the stack configuration following a user-initiated power-up.

Figure 16:
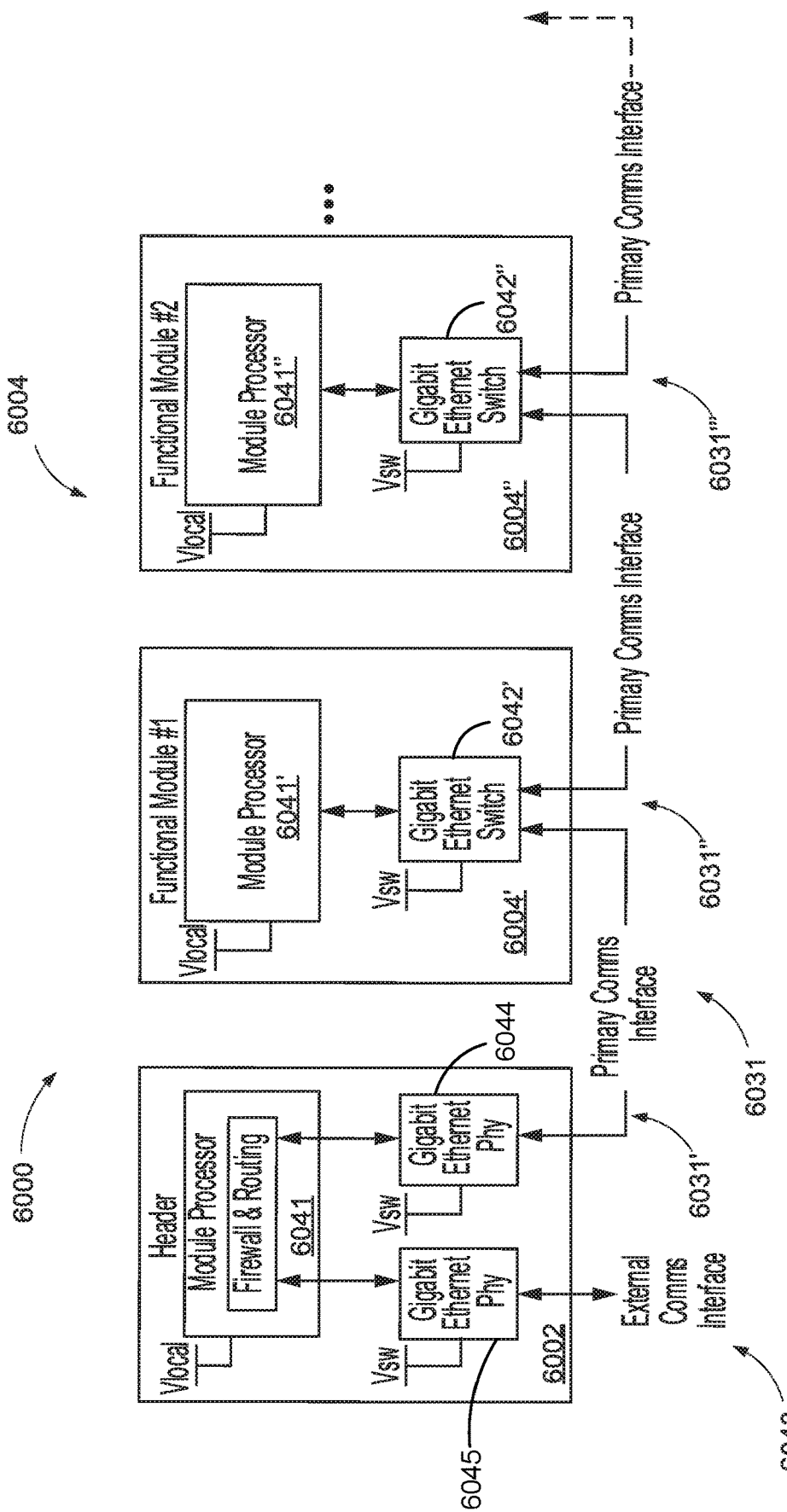
FIG. 16 is a schematic diagram of a modular energy system, in accordance with at least one aspect of the present disclosure.

In various aspects, as illustrated in FIG. 16, the modules of the modular energy system 6000 can be communicably coupled to the header module 6002 and/or to each other via a communication (Serial bus/Ethernet) interface 6040 such that data or other information is shared by and between the modules of which the modular energy system is constructed. An Ethernet switch domain 6013 can be derived from the primary power domain 6009, for example. The Ethernet switch power domain 6013 is segregated into a separate power domain, which is configured to power Ethernet switches within each of the modules in the stack configuration, so that the primary communications interface 6040 will remain alive when local power to a module is removed. In at least one example, the primary communication interface 6040 comprises a 1000BASE-T Ethernet network, where each module represents a node on the network, and each module downstream from the header module 6002 contains a 3-port Ethernet switch for routing traffic to the local module or passing the data up or downstream as appropriate.

Furthermore, in certain examples, the modular energy system 6000 includes secondary, low speed, communication interface between modules for critical, power related functions including module power sequencing and module power status. The secondary communications interface can, for example, be a multi-drop Local Interconnect Network (LIN), where the header module is the master and all downstream modules are slaves.

In various aspects, as illustrated in FIG. 15, a standby power domain 6010 is a separate output from the AC/DC power supply 6003 that is always live when the supply is connected to mains power 6020. The standby power domain 6010 is used by all the modules in the system to power circuitry for a mitigated communications interface, and to control the local power to each module. Further, the standby power domain 6010 is configured to provide power to circuitry that is critical in a standby mode such as, for example, on/off command detection, status LEDs, secondary communication bus, etc.

In various aspects, as illustrated in FIG. 15, the individual surgical modules 6004 lack independent power supplies and, as such, rely on the header module 6002 to supply power in the stack configuration. Only the header module 6002 is directly connected to the mains power 6020. The surgical modules 6004 lack direct connections to the mains power 6020, and can receive power only in the stack configuration. This arrangement improves the safety of the individual surgical modules 6004, and reduces the overall footprint of the modular energy system 6000. This arrangement further reduces the number of cords required for proper operation of the modular energy system 6000, which can reduce clutter and footprint in the operating room.

Accordingly, a surgical instrument connected to surgical modules 6004 of a modular energy system 6000, in the stack configuration, receives therapeutic energy for tissue treatment that is generated by the surgical module 6004 from power delivered to the surgical module 6004 from the AC/DC power supply 6003 of the header module 6002.

In at least one example, while a header module 6002 is assembled in a stack configuration with a first surgical module 6004', energy can flow from the AC/DC power supply 6003 to the first surgical module 6004'. Further, while a header module 6002 is assembled in a stack configuration with a first surgical module 6004' (connected to the header module 6002) and a second surgical module 6004" (connected to the first surgical module 6004'), energy can flow from the AC/DC power supply 6003 to the second surgical module 6004" through the first surgical module 6004'.

The energy generated by the AC/DC power supply 6003 of the header module 6002 is transmitted through a segmented power backplane 6008 defined through the modular energy system 6000. In the example of FIG. 15, the header module 6002 houses a power backplane segment 6008', the first surgical module 6004' houses a power backplane segment 6008", and the second surgical module 6004" houses a power backplane segment 6008'''. The power backplane segment 6008' is detachably coupled to the power backplane segment 6008" in the stack configuration. Further, the power backplane 6008" is detachably coupled to the power backplane segment 6008''' in the stack configuration. Accordingly, energy flows from the AC/DC power supply 6003 to the power backplane segment 6008', then to the power backplane segment 6008", and then to the power backplane segment 6008'''.

In the example of FIG. 15, the power backplane segment 6008' is detachably connected to the power backplane segment 6008" via pass-through hub connectors 6005, 6006 in the stack configuration. Further, the power backplane segment 6008" is detachably connected to the power backplane segment 6008''' via pass-through hub connectors 6025, 6056 in the stack configuration. In certain instances, removing a surgical module from the stack configuration severs its connection to the power supply 6003. For example, separating the second surgical module 6004" from the first surgical module 6004' disconnects the power backplane segment 6008''' from the power backplane segment 6008". However, the connection between the power backplane segment 6008" and the power backplane segment 6008''' remains intact as long as the header module 6002 and the first surgical module 6004' remain in the stack configuration. Accordingly, energy can still flow to the first surgical module 6004' after disconnecting the second surgical module 6004" through the connection between the header module 6002 and the first surgical module 6004'. Separating connected modules can be achieved, in certain instances, by simply pulling the surgical modules 6004 apart.

In the example of FIG. 15, each of the modules 6002, 6004 includes a mitigated module control 6023. The mitigated module controls 6023 are coupled to corresponding local power regulation modules 6024 that are configured to regulate power based on input from the mitigated module controls 6023. In certain aspects, the mitigated module controls 6023 allow the header module 6002 to independently control the local power regulation modules 6024.

The modular energy system 6000 further includes a mitigated communications interface 6021 that includes a segmented communication backplane 6027 extending between the mitigated module controls 6023. The segmented communication backplane 6027 is similar in many respects to the segmented power backplane 6008. Mitigated Communication between the mitigated module controls 6023 of the header module 6002 and the surgical modules 6004 can be achieved through the segmented communication backplane 6027 defined through the modular energy system 6000. In the example of FIG. 15, the header module 6002 houses a communication backplane segment 6027', the first surgical module 6004' houses a communication backplane segment 6027", and the second surgical module 6004" houses a communication backplane segment 6027'''. The communication backplane segment 6027' is detachably coupled to the communication backplane segment 6027" in the stack configuration via the pass-through hub connectors 6005, 6006. Further, the communication backplane segment 6027" is detachably coupled to the communication backplane segment 6027''' in the stack configuration via the pass-through hub connectors 6025, 6026.

Although the example of FIG. 15 depicts a modular energy system 6000 includes a header module 6002 and two surgical modules 6004' 6004", this is not limiting. Modular energy systems with more or less surgical modules are contemplated by the present disclosure. In some aspects, the modular energy system 6000 includes other modules such as, for example, a communications module. In some aspects, the header module 6502 supports a display screen such as, for example, the display 2006 (FIG. 7A) that renders a GUI such as, for example, the GUI 2008 for relaying information regarding the modules connected to the header module 6002. The GUI 2008 of the display screen 2006 can provide a consolidated point of control all of the modules making up the particular configuration of a modular energy system.

FIG. 16 depicts a simplified schematic diagram of the modular energy system 6000, which illustrates a primary communications interface 6040 between the header module 6002 and the surgical modules 6004. The primary communications interface 6040 communicably connects module processors 6041, 6041', 6041" of the header module 6002 and the surgical modules 6004. Commands generated by the module processor 6041 of the header module are transmitted downstream to a desired functional surgical module via the primary communications interface 6040. In certain instances, the primary communications interface 6040 is configured to establish a two-way communication pathway between neighboring modules. In other instances, the primary communications interface 6040 is configured to establish a one-way communication pathway between neighboring modules.

Furthermore, the primary communications interface 6040 includes a segmented communication backplane 6031, which is similar in many respects to the segmented power backplane 6008. Communication between the header module 6002 and the surgical modules 6004 can be achieved through the segmented communication backplane 6031 defined through the modular energy system 6000. In the example of FIG. 16, the header module 6002 houses a communication backplane segment 6031', the first surgical module 6004' houses a communication backplane segment 6031", and the second surgical module 6004" houses a communication backplane segment 6031'''. The communication backplane segment 6031' is detachably coupled to the communication backplane segment 6031" in the stack configuration via the pass-through hub connectors 6005, 6006. Further, the communication backplane 6031" is detachably coupled to the communication backplane segment 6031" in the stack configuration via the pass-through hub connectors 6025, 6026.

In at least one example, as illustrated in FIG. 16, the primary communications interface 6040 is implemented using the DDS framework running on a Gigabit Ethernet interface. The module processors 6041, 6041', 6041" are connected to Gigabit Ethernet Phy 6044, and Gigabit Ethernet Switches 6042', 6042". In the example of FIG. 16, the segmented communication backplane 6031 connects the Gigabit Ethernet Phy 6044 and the Gigabit Ethernet Switches 6042 of the neighboring modules.

In various aspects, as illustrated in FIG. 16, the header module 6002 includes a separate Gigabit Ethernet Phy 6045 for an external communications interface 6043 with the processor module 6041 of the header module 6002. In at least one example, the processor module 6041 of the header module 6002 handles firewalls and information routing.

Referring to FIG. 15, the AC/DC power supply 6003 may provide an AC Status signal 6011 that indicates a loss of AC power supplied by the AC/DC power supply 6003. The AC status signal 6011 can be provided to all the modules of the modular energy system 6000 via the segmented power backplane 6008 to allow each module as much time as possible for a graceful shutdown, before primary output power is lost. The AC status signal 6011 is received by the module specific circuits 6013, 6014, 6015, for example. In various examples, the system power control 6017 can be configured to detect AC power loss. In at least one example, the AC power loss is detected via one or more suitable sensors.

Referring to FIGS. 15 and 16, to ensure that a local power failure in one of the modules of the modular energy system 6000 does not disable the entire power bus, the primary power input to all modules can be fused or a similar method of current limiting can be used (e-fuse, circuit breaker, etc.). Further, Ethernet switch power is segregated into a separate power domain 6013 so that the primary communications interface 6040 remains alive when local power to a module is removed. In other words, primary power can be removed and/or diverted from a surgical module without losing its ability to communicate with other surgical modules 6004 and/or the header module 6002.

Over-Molded Light Pipe With Mounting Features

Having described a general implementation the header and modules of modular energy systems 2000, 3000, 6000, the disclosure now turns to describe various aspects of other modular energy systems. The other modular energy systems are substantially similar to the modular energy system 2000, the modular energy system 3000, and/or the modular energy system 6000. For the sake of brevity, various details of the other modular energy systems being described in the following sections, which are similar to the modular energy system 2000, the modular energy system 3000, and/or the modular energy system 6000, are not repeated herein. Any aspect of the other modular energy systems described below can be brought into the modular energy system 2000, the modular energy system 3000, or the modular energy system 6000.

As referenced elsewhere herein, modules of a modular energy system can include a number of different ports configured to deliver different energy modalities to corresponding surgical instruments that are connected thereto. For example, the energy module 2004 can include a port assembly 2012 that includes a bipolar port 2014, a first monopolar port 2016*a*, a second monopolar port 2016*b*, a neutral electrode port 2018 (to which a monopolar return pad is connectable), and a combination energy port 2020.

In one aspect, the ports 2012, 2014, 2016*a*, 2016*b*, 2018, 2020 can be configured to relay information to users. For example, any of the ports 2012, 2014, 2016*a*, 2016*b*, 2018, 2020 can include light assemblies 2015 that can be configured to relay information to the user regarding the port according to their color or state (e.g., flashing, solid, patterned, etc.). For example, a light assembly 2015 can change from a first color to a second color when a plug is fully seated within the respective port. As another example, a light assembly 2015 can flash a color, such as red, when a plug is improperly seated in the respective port. In one aspect, the color or state of the light assemblies 2015 can be controlled by the header module 2002. For example, the header module 2002 can cause the light assembly 2015 of each port to display a color corresponding to the color display for the port on the GUI 2008. Various other aspects are envisioned where the ports can shine any number of colors for the purposes of conveying information to a user, such as when a port is available for use, when a port is not available for use, when there is a problem with a port, an energy level associated with a port, etc.

As the light generated by the energy module 2004 and the light assemblies 2015 can provide a user with critical information regarding the current state and functionality of the ports of the port assembly 2012, it is important that light generated for a respective port is only visible where intended. For example, it is important that light emitted to convey information for one port, such as the bipolar port 2014, is not inadvertently shone through the energy module 2004 and seen at other locations of the energy module, such as at the monopolar port 2016*a* that is adjacent to the bipolar port 2014. This inadvertent light could confuse a clinician as to what information the energy module is trying to convey.

In various aspects, the light assemblies 2015 can comprise light pipes, which are materials that are meant to allow light to travel while being diffused, increase the apparent brightness of printed circuit board (PCB) mounted light emitting diodes (LEDs) within the module, while also providing a more attractive user interface to the user. In one aspect, should a gap be defined between the light pipe and any of its surrounding components, light could inadvertently shine to other areas where the light is not intended to shine, such as through the energy module and out of another port. Therefore, a need exists to ensure that light is only shone to areas where intended. In addition, it is desirable that the light pipe be able to be mounted to the enclosure of the energy module. Mounting the light pipe to the enclosure would provide an ease in assembly of the port with the enclosure, while allowing for quick replacement of the same should any component of the port need replaced.

Figure 17:
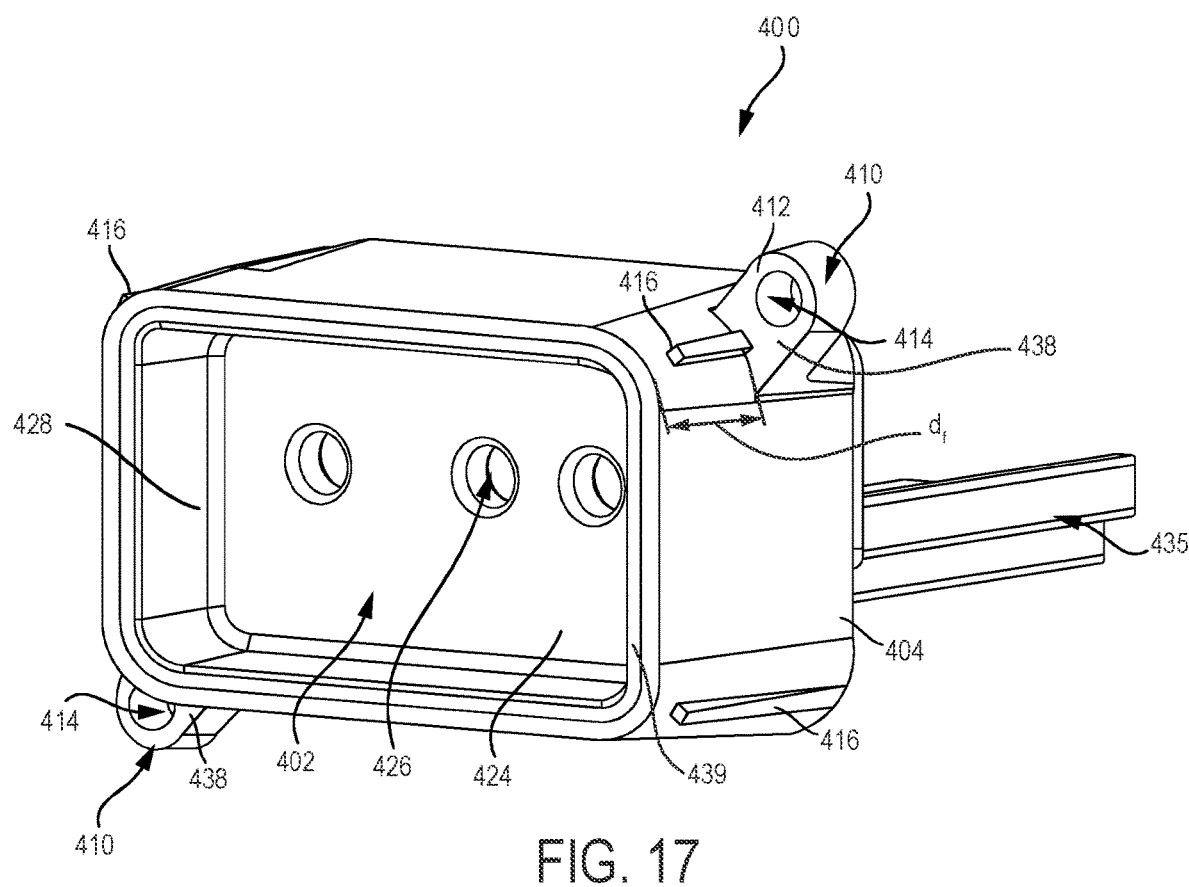
FIG. 17 illustrates a port module, according to at least one aspect of the present disclosure.
Figure 18:
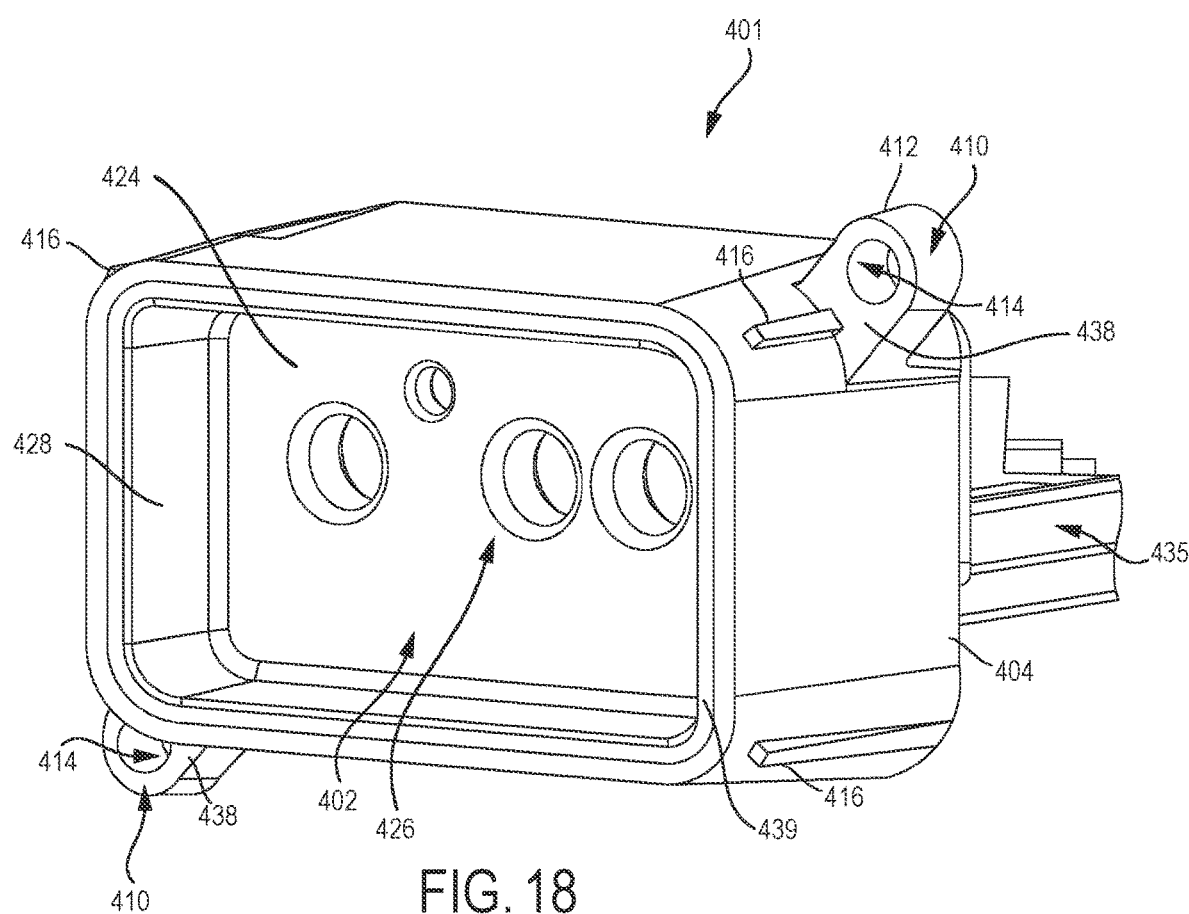
FIG. 18 illustrates another port module, according to at least one aspect of the present disclosure.
Figure 19:
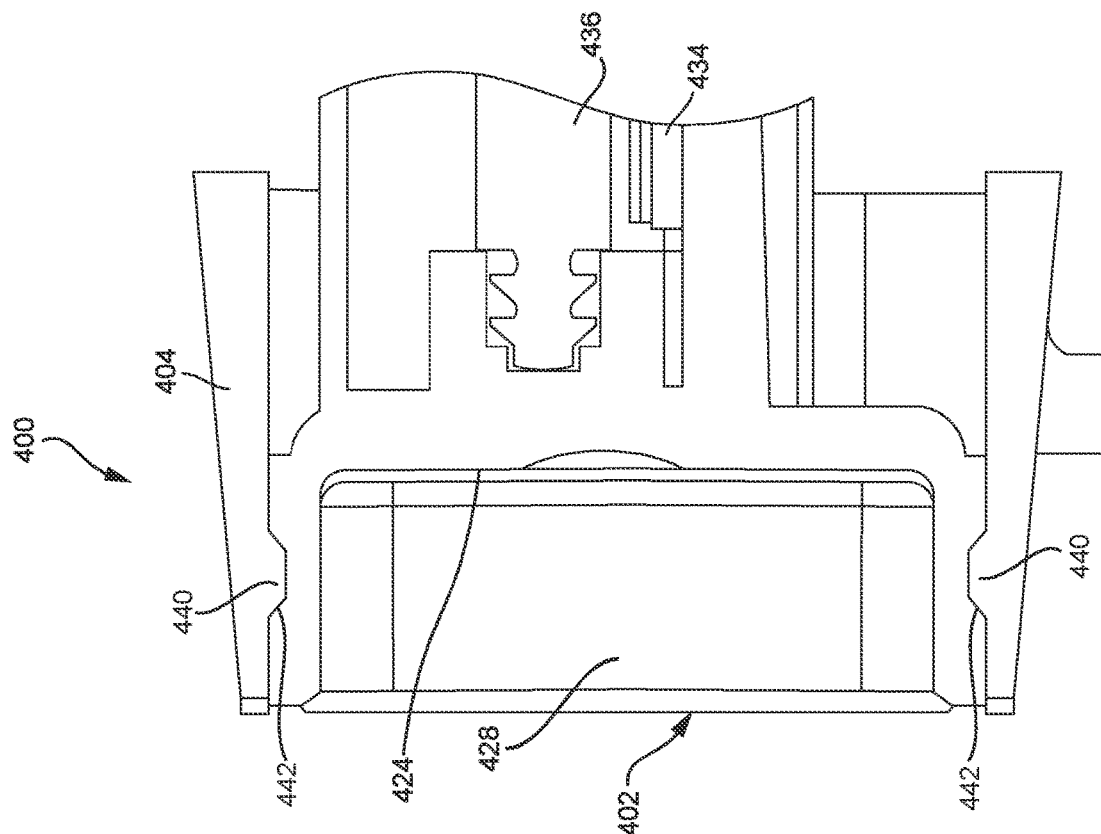
FIG. 19 illustrates a cross-section view of the port module of FIG. 17, according to at least one aspect of the present disclosure.

Referring to FIG. 17, a port module 400 is provided, according to at least one aspect of the present disclose. In one aspect, the port module 400 can include a receptacle 402, a light pipe 404 surrounding the receptacle 402, and mounting features 410 extending from the light pipe 404. While the port module shown in FIG. 17 is intended for use as one type of port module 400 (monopolar port module, bipolar port module, neutral electrode port module, combo energy port module, etc.), it should be understood that the port modules can be sized and configured for use as other types of port modules, such as port module 401 shown in FIG. 18, that includes a different number of apertures to receive a different type of plug than port module 400.

Figure 23:
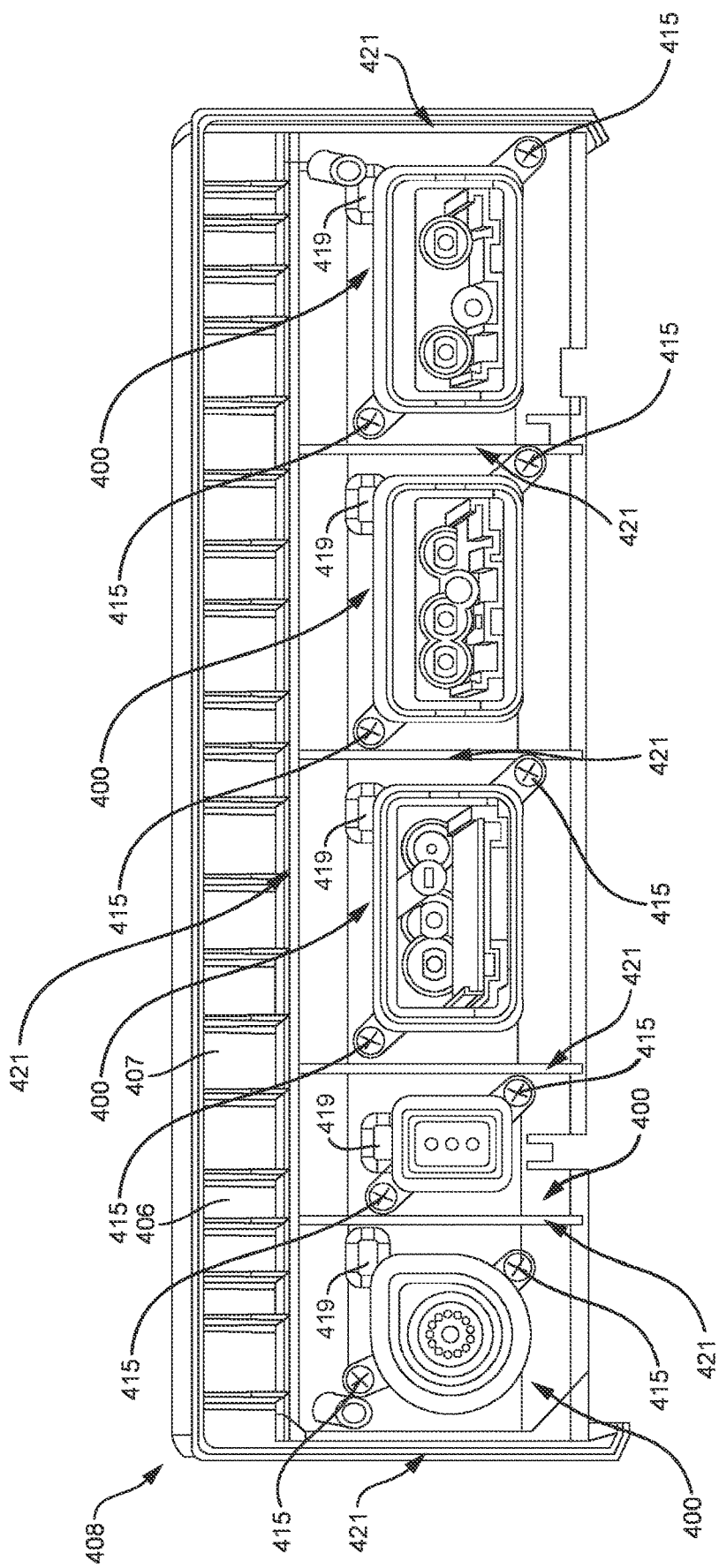
FIG. 23 illustrates the rear view of FIG. 22 with the control circuit removed, according to at least one aspect of the present disclosure.
Figure 24:
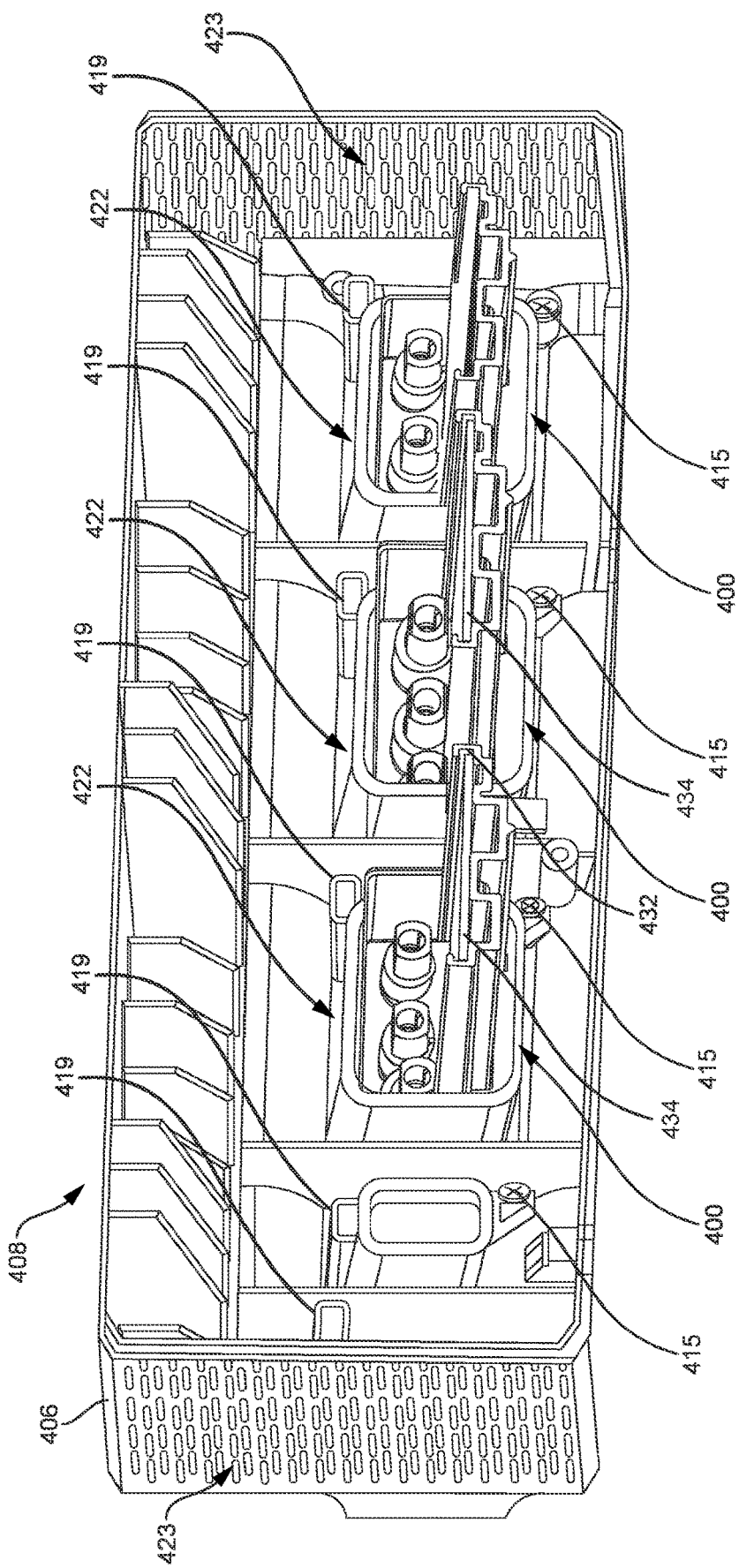
FIG. 24 illustrates an isometric view of FIG. 24, according to at least one aspect of the present disclosure.

In various aspects, the mounting features 410 can include a mounting arm 412 and an aperture 414 defined in the mounting arm 412. As shown in FIGS. 23 and 24, as an example, the aperture 414 can be sized to receive a fastener 415, such as a screw, therethrough to mount the port module 400 to an enclosure 406 of an energy module 408. In various aspects, as shown in FIG. 24, the port module 400 can be mounted to an inner face 407 of the enclosure 406. Various other aspects are envisioned where the port module 400 can be mounted to a different part of the enclosure 406, such as to an outer face of the enclosure 406.

Figure 25:
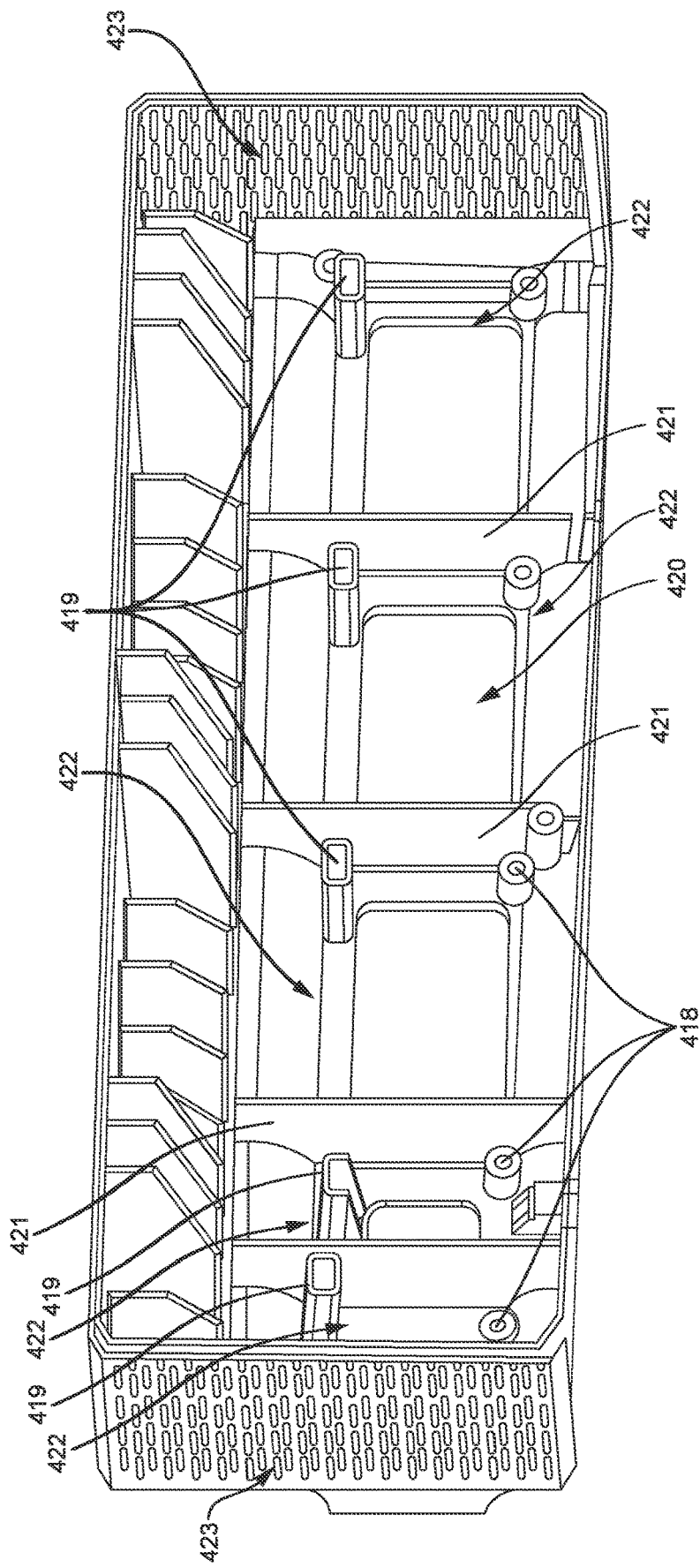
FIG. 25 illustrates the isometric view of FIG. 24 with the port modules removed, according to at least one aspect of the present disclosure.

In various aspects, the mounting features 410 can further include alignment rails that can assist in properly aligning the apertures 414 of the mounting features 410 with corresponding mounting holes 418 defined in the enclosure 406, illustrated in FIG. 25, which are sized to receive a fastener 415 for mounting the port module 400 to the enclosure 406. In one aspect, the alignment rails can be received by a track defined by the enclosure 406 to guide the aperture 414 into operable alignment with the mounting hole 418 of the enclosure 406. The alignment rails and the tracks can ensure that the port module 400 is properly received and positioned in apertures 420 defined in the enclosure 406, as is shown in FIG. 25. In various aspects, the port module 400 can further include auxiliary alignments rails on other areas of the light pipe 404 that do not include mounting features 410 to further assist in aligning the port module 400 with the corresponding aperture 420 defined in the enclosure 406. Similar to the alignment rails, the auxiliary alignment rails can be received by a track to further assist in ensuring that the port module 400 is properly received and positioned in the aperture 420 defined in the enclosure 406. In one aspect, the alignment rails, the auxiliary alignment rails, and tracks can be defined to ensure the front face of the port module 400 fits flush with the external face of the enclosure 406, thereby preventing the port module 400 from "sticking out" past the front face of the enclosure 406. In various aspects, the mounting arms 412 can be received by a mounting boss within the enclosure 406. The mounting arms 412 can be positioned on the light pipe 404 such that they do not nominally touch off the mounting boss of the enclosure 406, which can cause a forward bias, ensuring the alignment rails make contact with the inside surface of the enclosure 406.

As shown in FIG. 17, the port module 400 can include two mounting features 410 extending from the light pipe 404 to allow the port module 400 to be mounted to the enclosure 406 of the energy module 408. The mounting features 410 can extend from opposite corners of the port module 400 to provide for a secure connection of the port module 400 to the enclosure 406. The use of at least two mounting features 410 can ensure that the port module 400 does not rotate out of its intended position when mounted to the enclosure 406. While two mounting features 410 are shown and described, any number of mounting features 410 can be utilized to couple the port module 400 to the enclosure 406. While the mounting features 410 are shown extending from opposite corners of the light pipe 404, the mounting features 410 can extend from any suitable location of the light pipe 404 to ensure that a secure connection is made between the port module 400 to the enclosure 406 to maintain the port module 400 in the respective apertures 420. The mounting features 410 can also be sized and positioned such that apertures 414 of the mounting features 410 operably align with mounting holes 418 defined in the enclosure 406 to ensure that the fastener 415 can extend through both the aperture 414 and the mounting hole 418 to properly mount the port module 400 to the enclosure 406. In one aspect, the apertures 414 can comprise threads such that the aperture 414 can be threadably coupled to the fastener 415 that also threadably couples to the mounting hole 418 of the enclosure 406.

In one aspect, light emitted from the light pipe 404 can be emitted laterally therefrom and enter the mounting features 410, which can cause the occurrence of bright or dull spots in the port module 400. In various aspects, the mounting features 410 can extend from the light pipe 404 such that a distance $d_f$ is defined between the front faces 438 of the mounting features 410 and the front face 439 of the light pipe 404. The distance $d_f$ can be selected in order to reduce the occurrence of bright or dull spots, due to light emitted light pipe 404 entering the areas of the mounting features 410. In various aspects, the cross sectional area at the interface between the mounting arms 412 of the mounting features 410 and light pipe 404 body can be reduced to further minimize light loss. In one aspect, the above-described improvements can reduce the occurrence of inconsistent output from the light pipe 404. In various aspects, the mounting features 410 can be comprised a light diffusing material, such as an opaque plastic.

In various aspects, the enclosure 406 of the energy module 408 can define predefined compartments 422, shown in FIGS. 24 and 25, that can receive the port modules 400 therein. In one aspect, the mounting features 410 can be sized such that the port modules 400 can fit within predefined compartments 422 defined within the enclosure 406 that include the apertures 420. In various aspects, the enclosure 406 can define a plurality of ribs 421 that can separate the predefined compartments 422 of the enclosure 406. The ribs 421 can be sized and positioned to prevent compartment 422 to compartment 422 light bleeding, as will be discussed in more detail below, to ensure that light emitted within one compartment 422 for one port module 400 is not inadvertently seen in another compartment 422 that includes a second port module 400. While ribs 421 are shown as being defined by the enclosure 406 to separate the predefined compartments 422, any number of ribs 421 can be utilized within other areas of the enclosure 406 to further inhibit light travel within the enclosure 406. In various aspects, the ribs 421 and the enclosure 406 can be of unitary construction. For example, the enclosure 406 and the ribs 421 can be formed together with an injection molding process. In various aspects, the ribs 421 can be separate components that can be removably or permanently attached to enclosure 406. For example, the ribs 421 could be part of a separate component of the system that are put in place during assembly of the enclosure 406.

Figure 37:
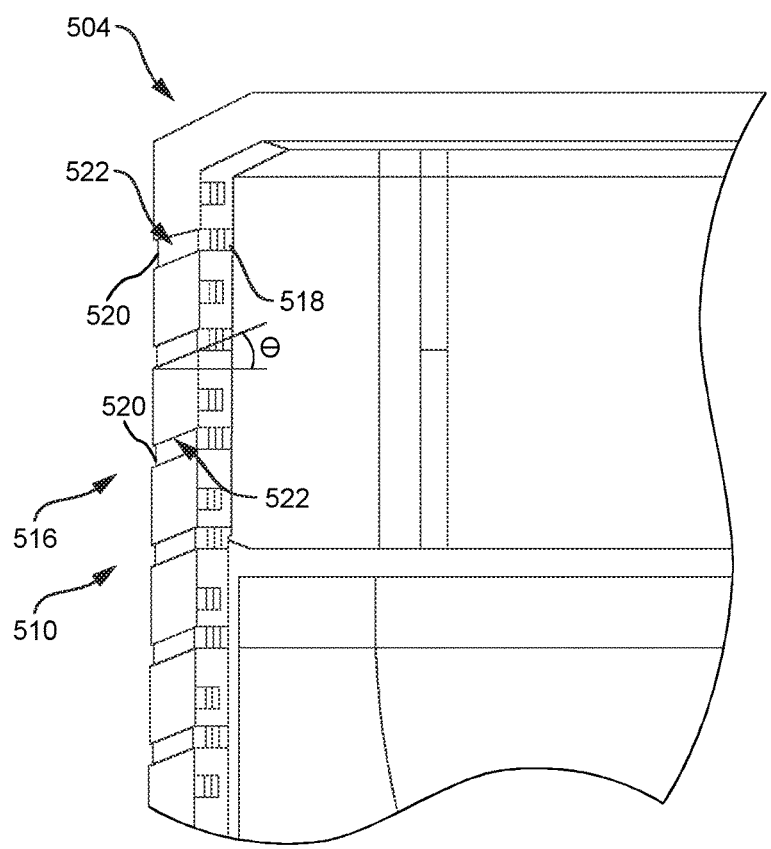
FIG. 37 illustrates a close-up view of the angled vents of the energy module of 35, according to at least one aspect of the present disclosure.

In various aspects, referring to FIGS. 23-25, each compartment 422 of the enclosure 406 can define a chimney 419, which can serve as a light guide to guide light emitted from the LEDs to icons that exist on the outer surface of the enclosure 406. The chimneys 419 can cause the icons to illuminate to convey various states associated with for the port module 400 positioned in the compartment 422. In one aspect, the chimneys 419 can include a very shallow diffuse material and direct the light towards the outer indicator for the purposes of conveying information to a user of the system. In one aspect, the chimneys can block light for a dedicated LED for the indicators In various aspects, the enclosure 406 can define vent holes 423, as shown in FIGS. 24, 25, 26, and 27, that can function to vent out heat generated within the energy module 408. During use of the energy module 408, light could bleed through the vent holes 423 and shine into other areas of the operating room, thus confusing the clinician as to what signals are trying to be conveyed. In one aspect, the ribs 421 can be defined within the enclosure 406 to prevent light generated within the energy module 408 from bleeding out through the vent holes 423. In various other aspects, the vents 423 could be angled, such as is shown in FIG. 37 and will be described in more detail elsewhere herein, to further inhibit light escape from the energy module 408.

In one aspect, referring again to FIG. 17, the mounting features 410 can be molded directly onto the light pipe 404. In various aspects, the light pipe 404 and the mounting features 410 can be of unitary construction. In various aspects, the light pipe 404 and the mounting features 410 can be manufactured by a molding process, such as with an injection molding process, as an example. Molding of the mounting features 410 directly on the light pipe 404 can ensure accurate placement of the port module 400 relative to the apertures 420 of the enclosure 406 as the port module 400 is mounted to the enclosure 406, as well as ensures accurate placement of the light pipe 404 relative to LEDs within the energy module 408, as will be described in more detail below. In various other aspects, the light pipe 404 and the mounting features 410 can be separately constructed and then coupled together, such as with a bonding agent. In various aspects, the mounting features 410 can be removably coupleable to the light pipe 404 to allow for replacement of the mounting features 410 should one break, as an example.

Figure 22:
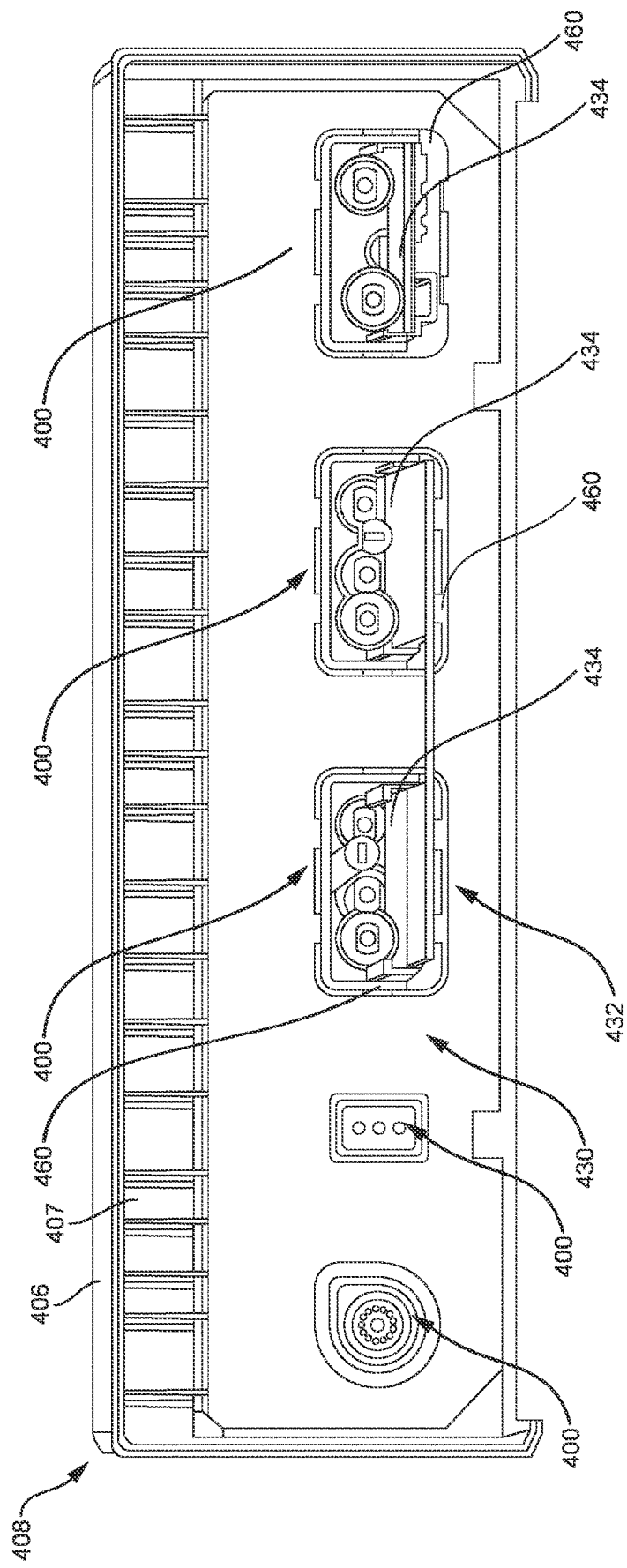
FIG. 22 illustrates a rear view of a header module that includes a plurality or port modules and a control circuit, according to at least one aspect of the present disclosure.

In various aspects, referring now to FIG. 22, the energy module 408 can include a control circuit 430 that can be positioned within the energy module 408 adjacent to the apertures 420 of the energy module 408. The control circuit 430 can define a plurality of apertures 432 that can be sized and positioned along the control circuit 430 to align with the apertures 420 defined in the enclosure 406 such that the port modules 400 can extend through both sets of apertures 420, 432. In various aspects, the control circuit 430 can include a plurality of LEDs positioned thereon that face an inner wall 407 and the apertures 420. The plurality of LEDs can be grouped and positioned adjacent to the apertures 420 defined in the enclosure 406 such that, when information is to be conveyed to a user, a specific grouping of LEDs of the plurality of LEDs can be illuminated and shine through the respective aperture 420. Example LEDs on a control circuit can be seen on FIG. 37.

In various aspects, the port modules 400 can comprise a port module circuit 434 that can electrically couple to the control circuit 430 when the port module 400 is coupled to the energy module 408. In one aspect, the control circuit 430 can transmit signals to the port module circuit 434 when the port module 400 is coupled to the enclosure 406, as will be described in more detail below, for the purposes of transmitting electrical signals to electrosurgical instruments that are coupled to the port module 400. In various aspects, referring to FIG. 17, the port modules 400 can include a circuit holder 435 extending from the receptacle 402, which can be sized to hold the port module circuit 434.

As referenced above, the port modules 400 can include a light pipe 404. The light pipes 404 can be optically coupled to respective LEDs on the control circuit 430 such that that the light pipes 404 can transmit optical, informational signals to a user of the energy module 408 from the LEDs. In one aspect, when the LEDs associated with one port module 400 are illuminated, light emitting from the LED(s) can emit into and through the light pipe 404, providing an increase the apparent brightness of the light emitted from the LED(s) and provide a user of the energy module 408 with a status of the port module 400 according to the light that is emitted by the LEDs. In various aspects, the LEDs and light pipe 404 can emit solid light, flashing light, patterned light, or any other type of light state, to indicate information to the user about a status of the port module 400. Further, the LEDs and light pipe 404 can emit any number of colors according to the status of the port module 400, such as operational status, energy level status, etc. As one example, the LEDs and light pipe 404 can emit solid green light when the port module 400 is ready for use, emit flashing red light when the port module 400 is not ready for use, and emit patterned yellow light when the port module 400 is being prepared for use. Any number of color and light states (solid, flashing, patterned, etc.) can be utilized to convey information to a user.

As referenced above, referring again to FIG. 17, the port module 400 can include a receptacle 402. As shown in FIG. 17, the perimeter of the receptacle 402 can be defined by the inner surface of the light pipe 404. In various aspects, the receptacle 402 can be sized to receive a plug from a corresponding surgical instrument therein, such as is shown in FIG. 4, as an example. The receptacle 402 can include a back wall 424 that defines apertures 426 therein and sidewalls 428 extending away from the back wall 424. The size of the receptacle 402, as well as the size, position, and number of apertures 426 defined in the back wall 424, can be defined to correspond to an intended plug of a surgical instrument to be used with the port module 400. For example, in one aspect, referring to FIG. 17, the back wall 424 can define three apertures corresponding to one type of plug. In another example aspect, referring to FIG. 18, the back wall 424 of a port module 401 can define four apertures corresponding to a second type of plug.

Figure 26:
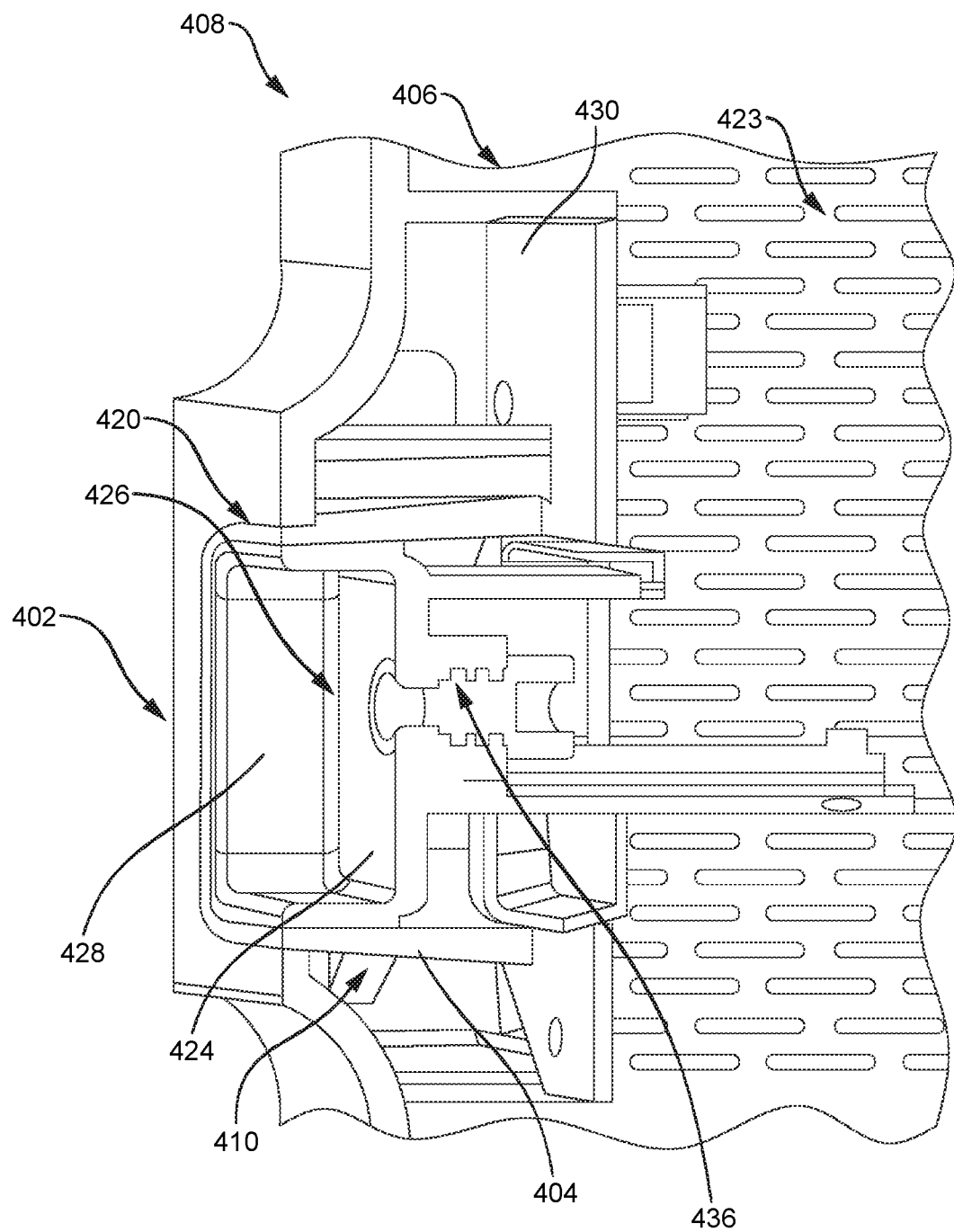
FIG. 26 illustrates an isometric view of a port module coupled to a header module, according to at least one aspect of the present disclosure.
Figure 27:
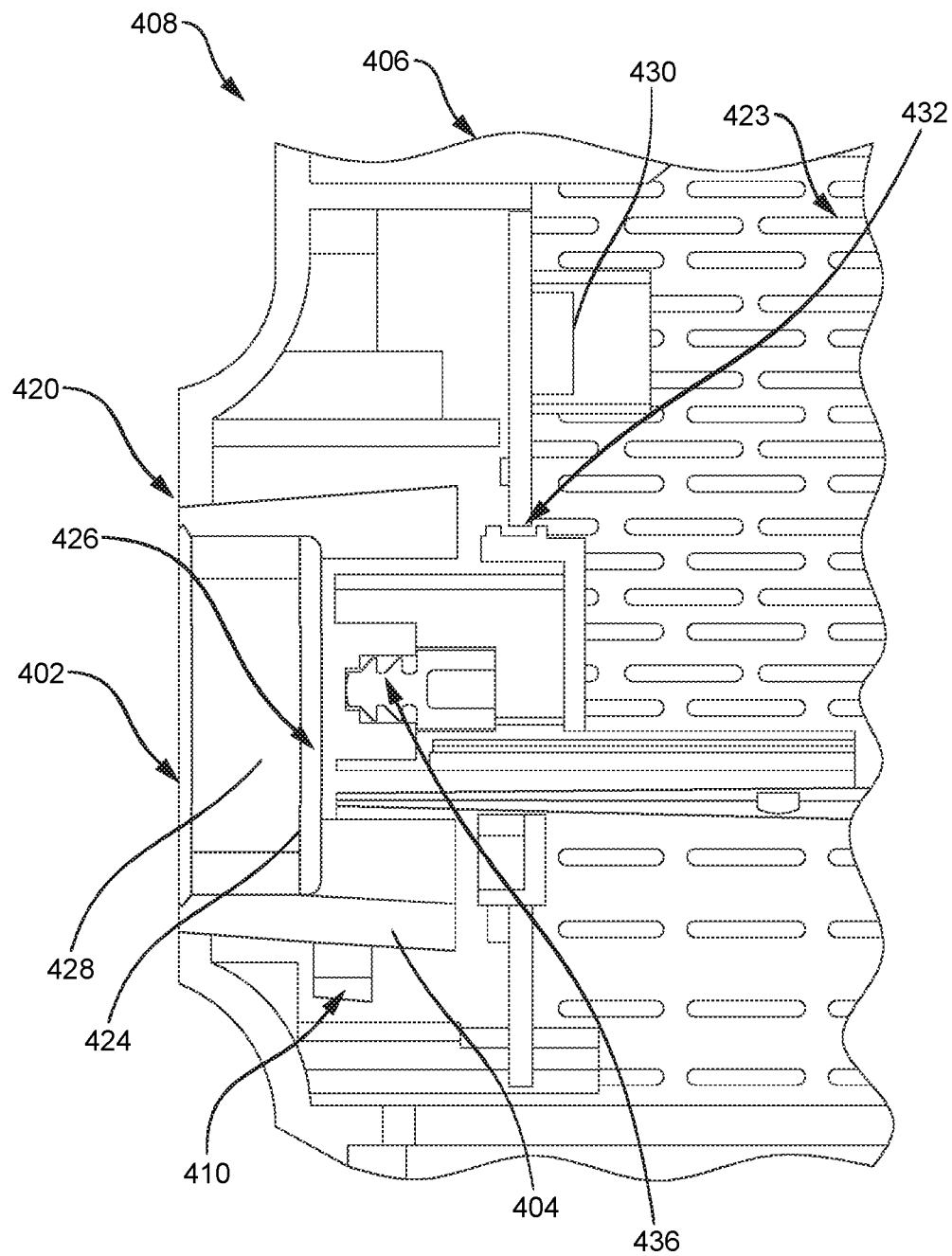
FIG. 27 illustrates a side view of FIG. 26, according to at least one aspect of the present disclosure.

In various aspects, referring now to FIG. 26, the port module circuit 434 can be electrically coupled to pin receptacles 436 that are disposed within the apertures 426 of the back wall 424. The pin receptacles 436 can be in electrical communication with the port module circuit 434 and can be sized to receive pins from plugs of electrosurgical instruments therein. When the pins of the plugs are positioned in the pin receptacles 436 and the port module circuit 434 is in electrical communication with the control circuit 430 of the energy module 408, the control circuit 430 of the energy module 408 can transmit electrical signals to the electrosurgical instrument.

In various aspects, the receptacle 402 can be molded directly within light pipe 404 to define a seal therebetween. In various aspects, the light pipe 404 can be comprised of a first material and the receptacle 402 can be comprised of a second material, where the first material has a higher melting temperature than the first material. The light pipe 404 can be injection molded with the first material to define the shape of the light pipe 404. Once the light pipe 404 has been formed, the receptacle 402 can be injection molded with the second material within the formed light pipe 404 to define the back wall 424 and sidewalls 428. Once the second material has been injected into the light pipe 404, the apertures 426 can be defined in the back wall 424 according to the intended use of the port module 400. Injection molding the receptacle 402 within the light pipe 404 allows for the creation of a seal therebetween, which can prevent any inadvertent light from escaping between the light pipe 404 and the receptacle 402. This molding process can also ensure a strong bond between the light pipe 404 and the receptacle 402. The strong bond between the light pipe 404 and the receptacle 402 is critical as the mounting features 410 on the light pipe 404 are needed for mounting the port module 400 to the enclosure 406, and therefore, the strong bond is critical to ensure accurate alignment of the port module 400 with the apertures 420 of the enclosure 406.

As referenced above, a seal can be formed between the receptacle 402 and the light pipe 404. The seal can ensure that light from the light pipe 404 don't shine between the light pipe 404 and the receptacle 402, as well as ensures that the port module 400 is properly mounted to the enclosure 406. In various aspects, the receptacle 402 can be comprised of an opaque material. In one aspect, the opaque material can comprise a plastic opaque material. As referenced above, as a seal is defined between the light pipe 404 and the opaque receptacle 402, the opaque material can prevent light that is emitted from the LEDs and the light pipe 404 from inadvertently escaping and shining into unintended areas of the energy module 408. As one example, the seal and opaque material can ensure that light emitted from one grouping of LEDs and a light pipe 404 of one port module 400 is not mistakenly seen at another location of the energy module 408, such as at another port module 400.

Figure 20:
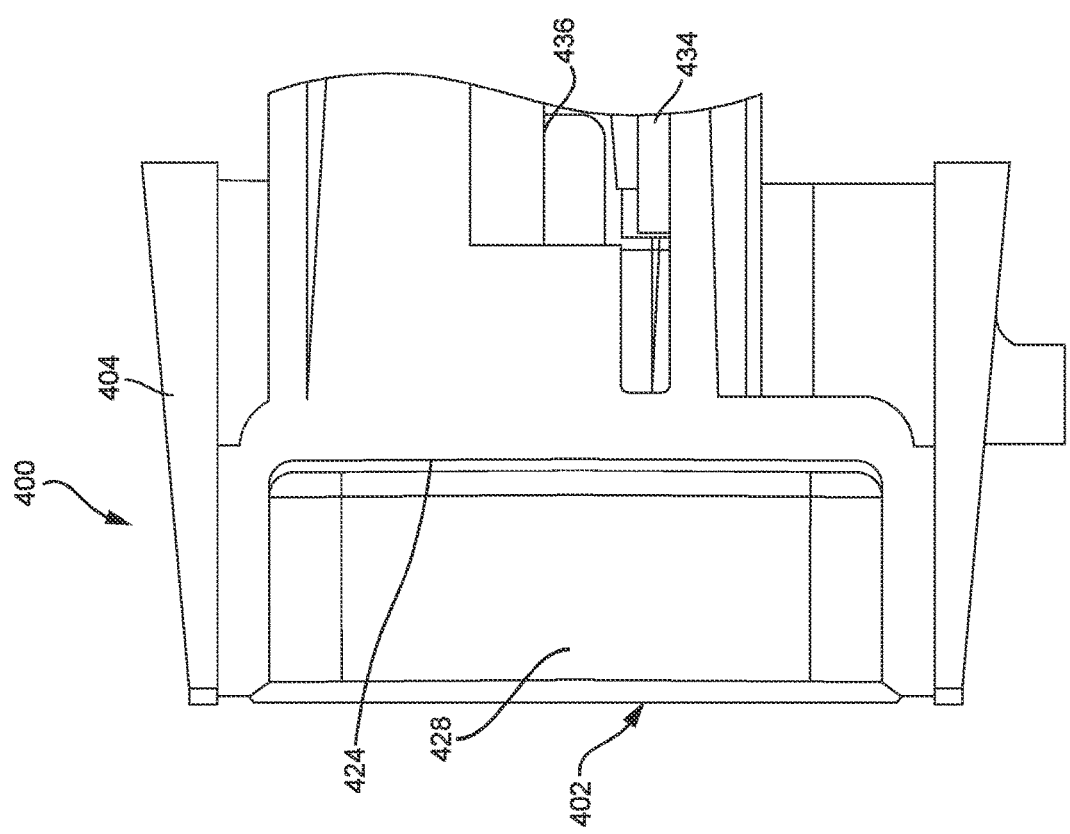
FIG. 20 illustrates another cross-section view of a port module of FIG. 17 and illustrates mechanical engagement features, according to at least one aspect of the present disclosure.
Figure 21:
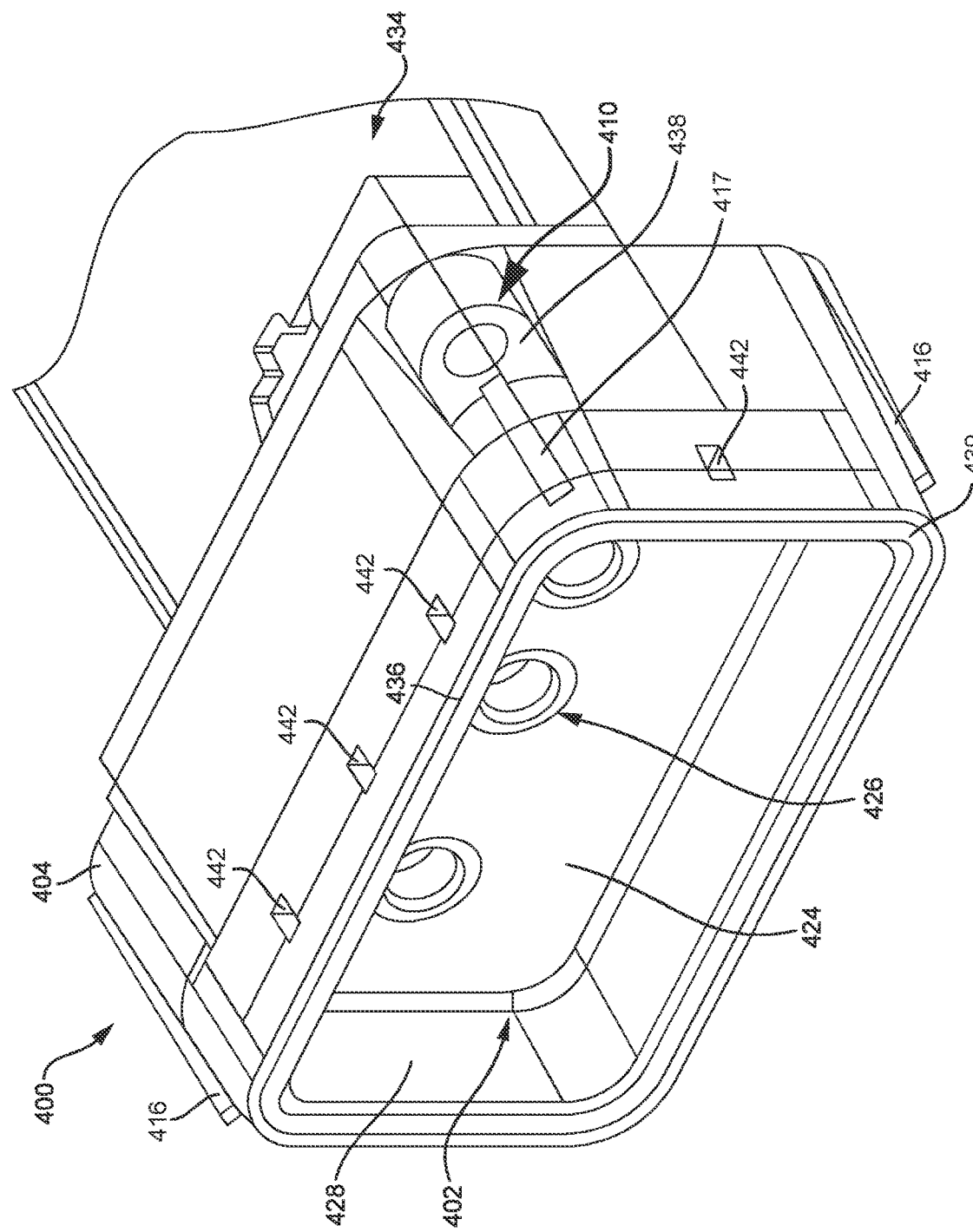
FIG. 21 illustrates an isometric view of the port module of FIG. 21, according to at least one aspect of the present disclosure.

In various aspects, referring now to FIGS. 20 and 21, the port module 400 can further include engagement features that improve mechanical strength and engagement between the light pipe 404 and other components of the port module 400, such as the receptacle 402. In one aspect, engagement features can comprise engagement arms 440 defined in the light pipe 404 that extend toward and be received in notches 442 defined in the receptacle 402. The engagement arms 440 can engage notches 442, which can improve the engagement between the light pipe 404 and the receptacle 402. In various aspects, the engagement arms 440 and notches 442 can be defined at any suitable location on the port module 400 to improve the mechanical strength and engagement between the light pipe 404 and other components of the port module 400, such as the receptacle 402.

In various aspects, referring to FIG. 17, the light pipe 404 can define stops 416 that can define recesses to receive engagement members 417 (see FIG. 21) extending from the receptacle 402 (note: FIG. 21 illustrates a phantom view of the light pipe 404 such that the outer surface of the receptacle 402 and an engagement member 417 extending therefrom can be seen while the receptacle 402 is positioned in the light pipe 404). In one aspect, the stops 416 and engagement members 417 of the receptacle 402 can be utilized to align the light pipe 404 with the receptacle 402. In one aspect, the engagement members 417 can be received in the stops 416 to create a flush relationship between the light pipe 404 and the receptacle 402 through a positive stop.

Light Blocking PCB Inserts

As referenced elsewhere herein, modules of a modular energy system can utilize light for the purposes of conveying information to a user of the modular energy system. For example, ports 2012, 2014, 2016a, 2016b, 2018, 2020 can be configured to relay information to users. For example, any of the ports 2012, 2014, 2016a, 2016b, 2018, 2020 can include light assemblies 2015 that can be configured to relay information to the user regarding the port according to their color or state (e.g., flashing, solid, patterned, etc.). For example, a light assembly 2015 can change from a first color to a second color when a plug is fully seated within the respective port. As another example, a light assembly 2015 can flash a color, such as red, when a plug is improperly seated in the respective port. In one aspect, the color or state of the light assemblies 2015 can be controlled by the header module 2002. For example, the header module 2002 can cause the light assembly 2015 of each port to display a color corresponding to the color display for the port on the GUI 2008. Various other aspects are envisioned where the ports can shine any number of colors for the purposes of conveying information to a user, such as when a port is available for use, when a port is not available for use, when there is a problem with a port, an energy level of a port, etc.

As the light generated by the modules provides a user with critical information regarding the current state of the module, it is important that light generated by the module is only visible where intended. As described elsewhere herein, the modules can include an enclosure, such as enclosure 406, that houses the components of the module therein. In various aspect, the enclosure can include apertures, such as apertures 420, defined therein that are sized to receive port modules, such as port modules 400, therein. The enclosure can further include a control circuit, such as control circuit 430, that can control various functions of the module, such as controlling LEDs thereon that are emitted to convey information to the user regarding the status of the port modules 400, as well as controlling an amount or type of energy that is delivered to an electrosurgical instrument that is coupled to the port module. The control circuit can also include apertures, such as apertures 432, that can be sized and positioned adjacent to apertures of the enclosure such that the port modules can extend through both the apertures of the enclosure and the apertures of the control circuit when the port module is coupled to the energy module. In various aspects, as referenced above, the control circuit can further include LEDs that are mounted to the control circuit. The LEDs can be positioned on the control circuit such that light emitted from the LEDs can emit toward the aperture of the enclosure, thus conveying information to the user about the status of the port modules.

Figure 31:
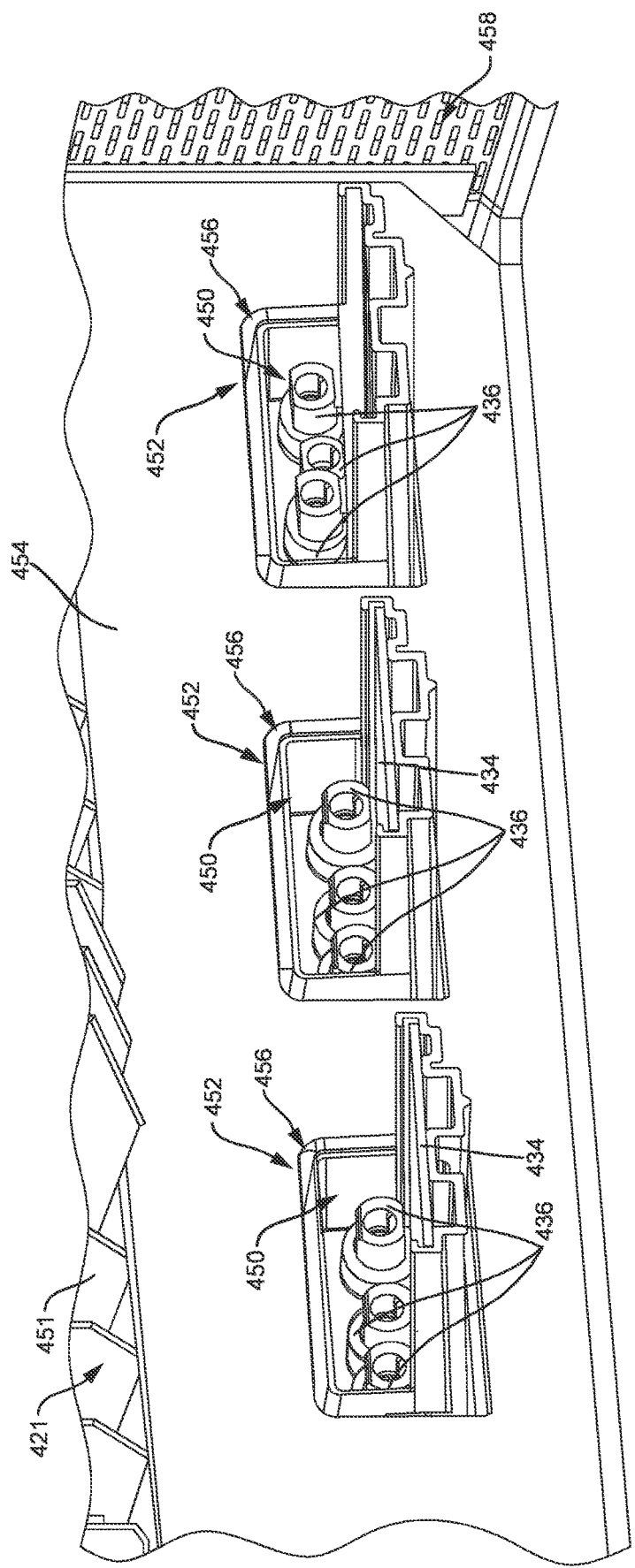
FIG. 31 illustrates the header module of FIG. 30 with the light blocking inserts removed, according to at least one aspect of the present disclosure.

Referring now to FIG. 31, when port modules 450, which can be similar to port modules 400, extend through apertures defined in the enclosure 451 and apertures 452 defined in the control circuit 454, a gap 456 can be defined between the inner perimeter of the aperture 452 and the port module 450. As a result of the gap 456, light emitted from the LEDs on the control circuit 454 can escape through the gap 456 and emit into other areas of the enclosure 451. In some scenarios, the escaped light could enter another aperture 452 defined in the control circuit, causing the light corresponding to one port module 450 to inadvertently been seen at different port module 450 location. As a result, a user could be confused as to which port module 450 is being illuminated and what information is being conveyed by the module. In other instances, the escaped light could also escape the enclosure 451 through the vents 458 defined in the sides of the enclosure 451 and be seen at other locations of the operating room. Accordingly, a need exists to block reward light travel through the gap 456 to prevent inadvertent light visibility at other locations of the enclosure 451 and the operating room.

Figure 28:
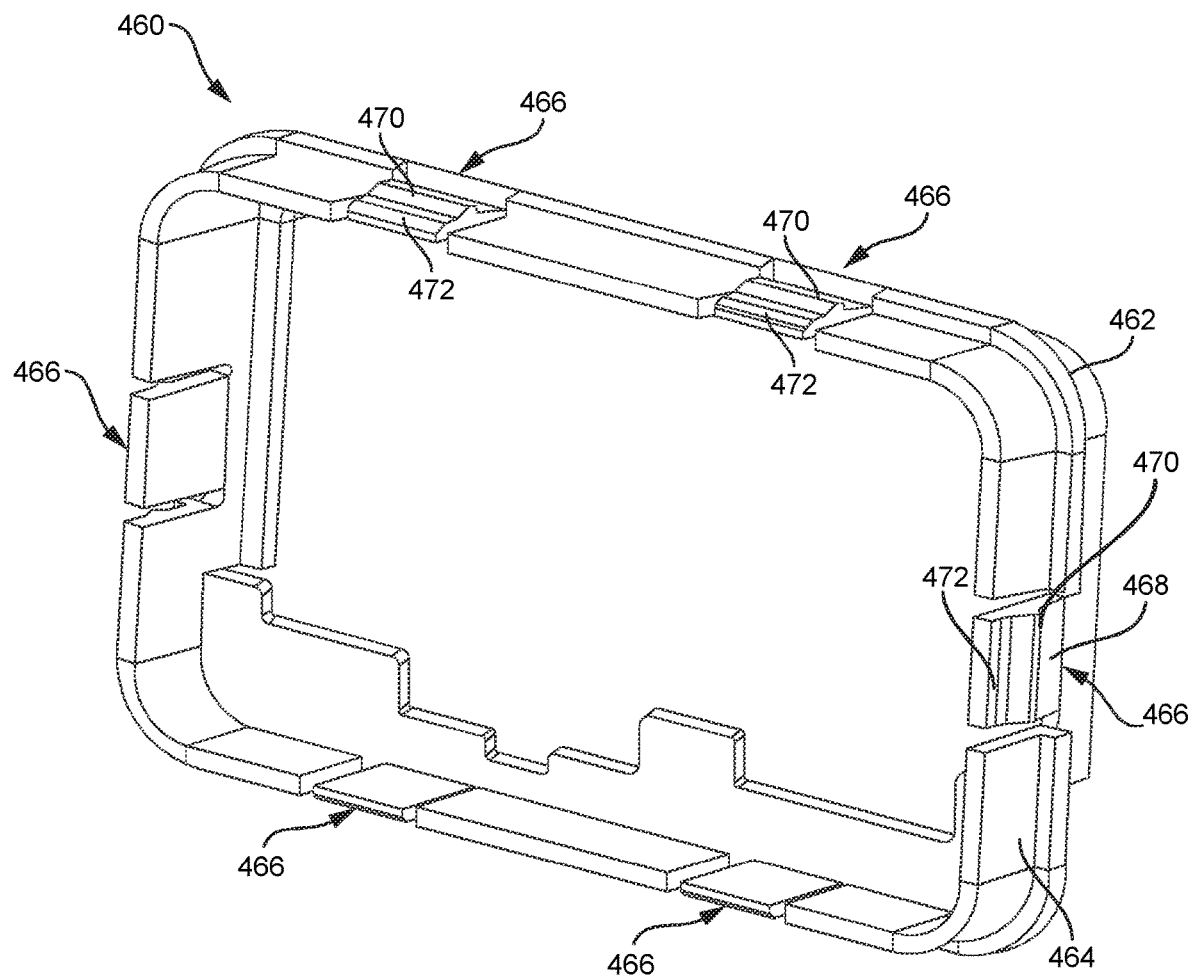
FIG. 28 illustrates a light blocking insert, according to at least one aspect of the present disclosure.
Figure 29:
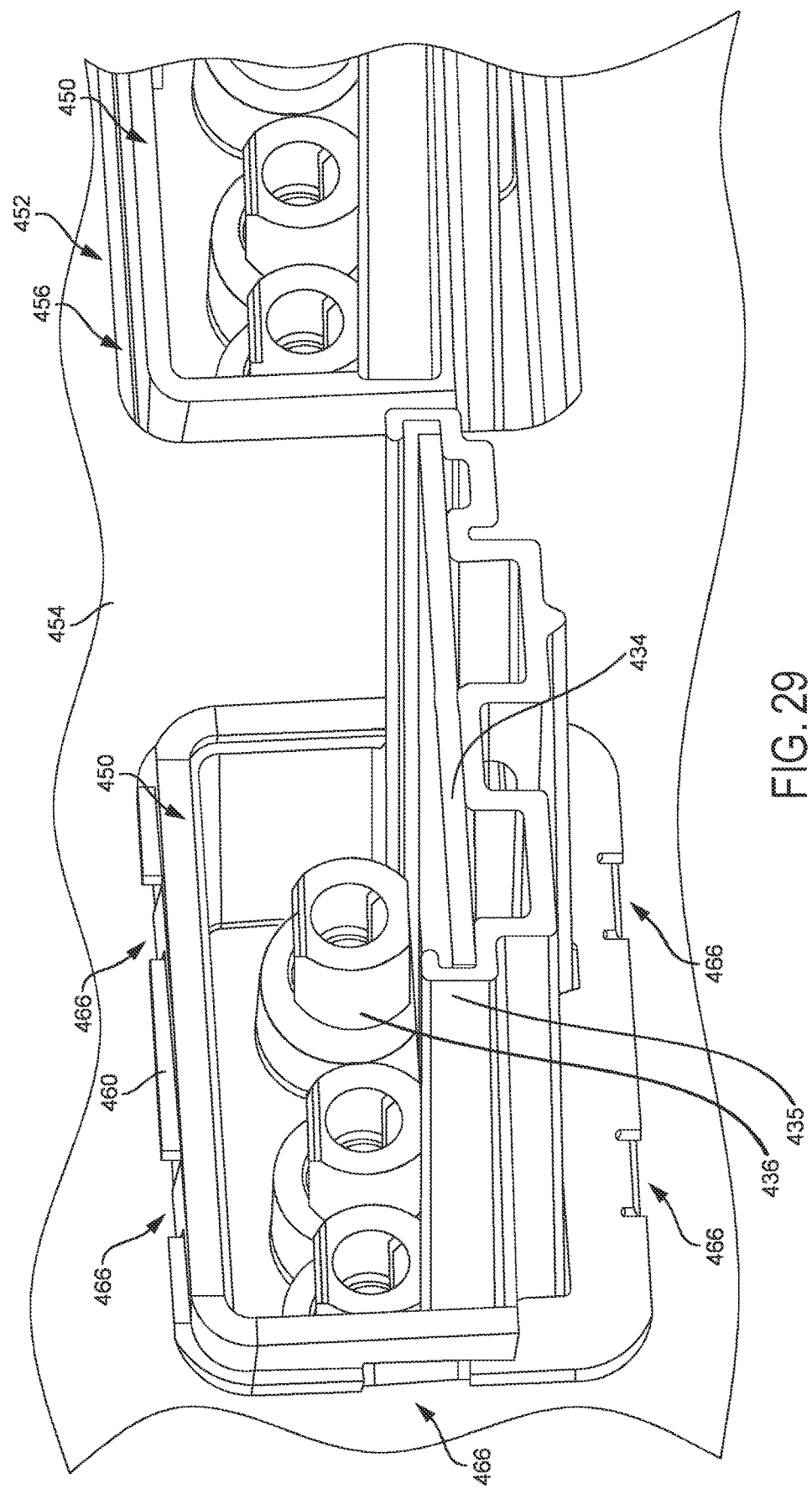
FIG. 29 illustrates a header module that includes two port modules, one with a light blocking insert therearound and one without a light blocking insert, according to at least one aspect of the present disclosure.
Figure 30:
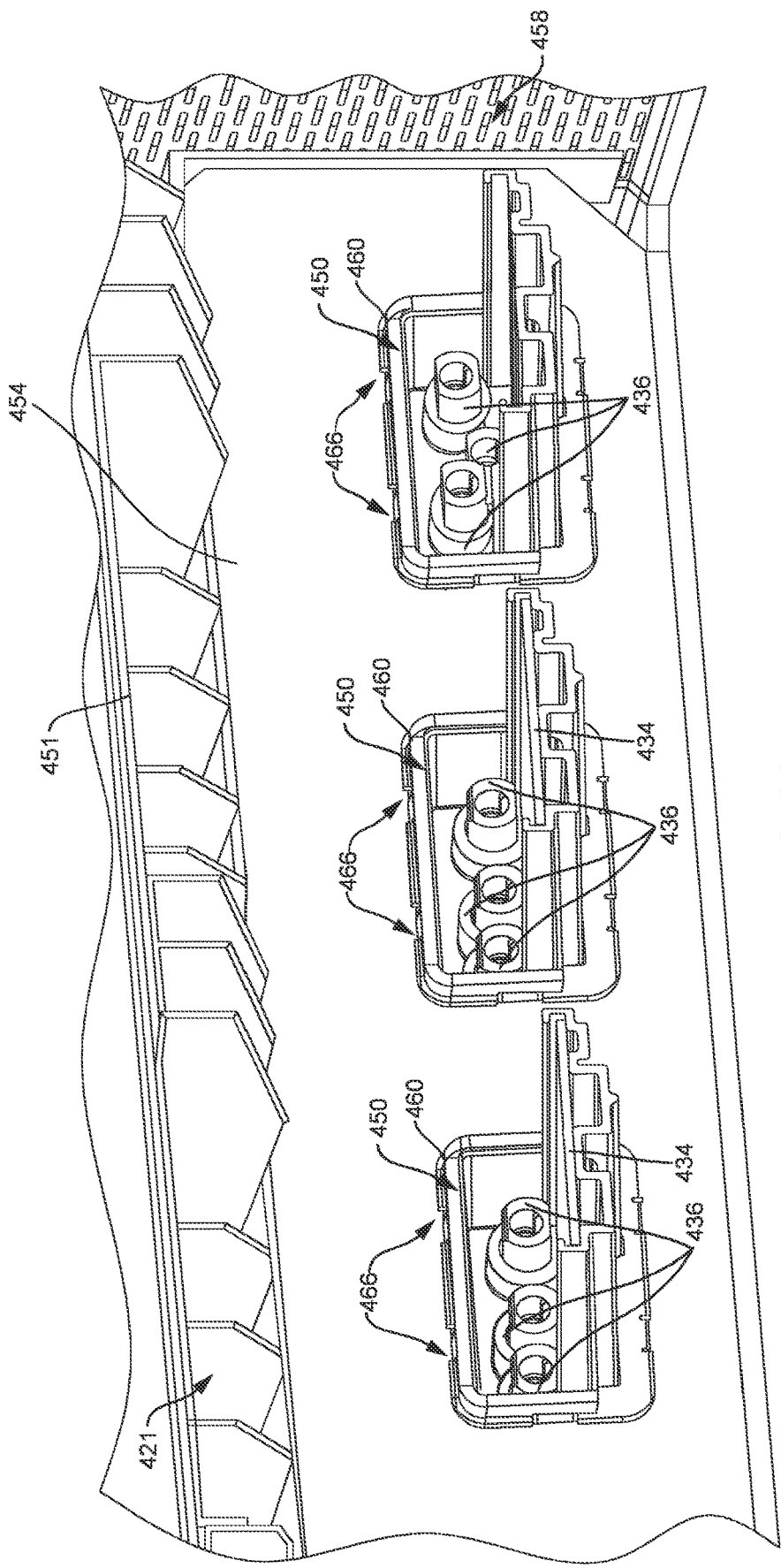
FIG. 30 illustrates a header module that includes a plurality of port modules that have light blocking inserts, according to at least one aspect of the present disclosure.

Referring now to FIG. 28, a light blocking insert 460 is provided, according to at least one aspect of the present disclosure. The light blocking insert 460 can include a face 462, guidewalls 464 extending from the face 462, and mounting features 466 extending from the face 462. Referring to FIGS. 29 and 30, the face 462 of the light blocking insert 460 can be defined such that, when the light blocking insert 460 is inserted into the aperture 452 of the control circuit 454, as will be discussed in more detail below, the face 462 can seal the gap 456 to prevent light from escaping through the gap 456 to other areas of the enclosure 451. As referenced above, the light blocking insert 460 can include a plurality of mounting features 466. The mounting features 466 can be movable relative to the guidewalls 464 between a resting position (seen in FIG. 28) and a depressed position. In various aspects, the mounting features 466 can be biased toward the resting position. While six mounting features are shown in FIG. 28, any more of less mounting features 466 can be utilized.

In various aspects, the mounting features 466 can include a base 468 extending from the face 462, a lip 470 extending from the base 468, and an actuator portion 472 extending from the base 468. In various aspects, the lip 470 can extend transversely relative to the base 468 and the actuator portion 472. In various aspects, the light blocking insert 460 can be removably coupled to the control circuit 454 to cover the gap 456. In operation, the guidewalls 464 and the mounting features 466 can be inserted through the aperture 452 of the control circuit 454 and toward the aperture of the enclosure 451. As the light blocking insert 460 moves through the aperture 452 of the control circuit 454, the lips 470 of the mounting features 466 can engage the inner perimeter of the aperture 452. The aperture 452 can force the mounting features 466 to rotate toward the depressed positions, allowing the lips 470 to pass from a first side of the control circuit 454, through the aperture 452, and to a second side of the control circuit 454. Once the lips 470 move beyond the aperture 452, the mounting features 466 can be snap back to the resting position, where the bases 468 and the lips 470 of the mounting features 466 can engage the control circuit 454, maintaining the position of the light blocking insert 460 relative to the control circuit 454, such as is shown in FIGS. 29 and 30. In one aspect, while the mounting features 466 are moving toward and through the apertures 452, the guidewalls 464 can assist in guiding the mounting features 466 into operable alignment with the inner perimeter of the apertures 452.

With the mounting features 466 operably engaged with the control circuit 454, a user can remove the light blocking insert 460 from the control circuit 454. In one aspect, the light blocking insert 460 can be removed by pushing the mounting features 466 toward the depressed position, thereby releasing the lip 470 and the base 468 from the control circuit 454. As referenced above, the mounting features 466 can include an actuator portion 472 extending from the base 468. In operation, a user can move the mounting features 466 toward the depressed position by pressing on the actuator portions 472 with, for example, their finger, to release the lip 470 and the base 468 from the control circuit 454, thereby allowing the light blocking insert 460 to be removed from the aperture 452. In various aspects, the actuator portion 472 can include grips defined therein to assist a user with moving the mounting features 466 toward the depressed position.

In various aspects, the light blocking insert 460 can be comprised of a plastic material and can be manufactured with a molding process. In one aspect, the molding process can be an injection molding process. In various aspects, the light blocking insert 460 can be manufactured using any other suitable manufacturing process, such as an additive manufacturing process, a 3D printing process, etc. In various aspects, the light blocking insert 460 can be comprised of an opaque plastic material. In various aspects, the light blocking insert 460 can be comprised of an opaque elastomeric material.

Angled Vents For Light Blocking

As referenced elsewhere herein, modules of a modular energy system can utilize light for the purposes of conveying information to a user of the modular energy system. For example, ports 2012, 2014, 2016a, 2016b, 2018, 2020 can be configured to relay information to users. For example, any of the ports 2012, 2014, 2016a, 2016b, 2018, 2020 can include light assemblies 2015 that can be configured to relay information to the user regarding the port according to their color or state (e.g., flashing, solid, patterned, etc.). For example, a light assembly 2015 can change from a first color to a second color when a plug is fully seated within the respective port. As another example, a light assembly 2015 can flash a color, such as red, when a plug is improperly seated in the respective port. In one aspect, the color or state of the light assemblies 2015 can be controlled by the header module 2002. For example, the header module 2002 can cause the light assembly 2015 of each port to display a color corresponding to the color display for the port on the GUI 2008. Various other aspects are envisioned where the ports can shine any number of colors for the purposes of conveying information to a user, such as when a port is available for use, when a port is not available for use, when there is a problem with a port, an energy level of a port, etc.

As the light generated by the modules provides a user with critical information regarding the current state of the module, it is important that light generated within the module only be visible where intended. In various aspects, modules can include an enclosure, such as enclosure 406, that houses the components of the module therein. In some aspects, the enclosure can include vents, such as vents 423, 458, defined therein for the purposes of venting heat out of the module to prevent the module from overheating. These vents, however, can allow for unintended escape of light generated within the module. This escaped light may shine onto other areas within the operating room that also rely on light for the purposes of indication. This overlap of light patterns may cause the clinician to become confused as what information is intended to be conveyed. Therefore, it is desirable to ensure that light generated by a module is not visible outside of the enclosure, such as through the vents, except for where intended.

Figure 32:
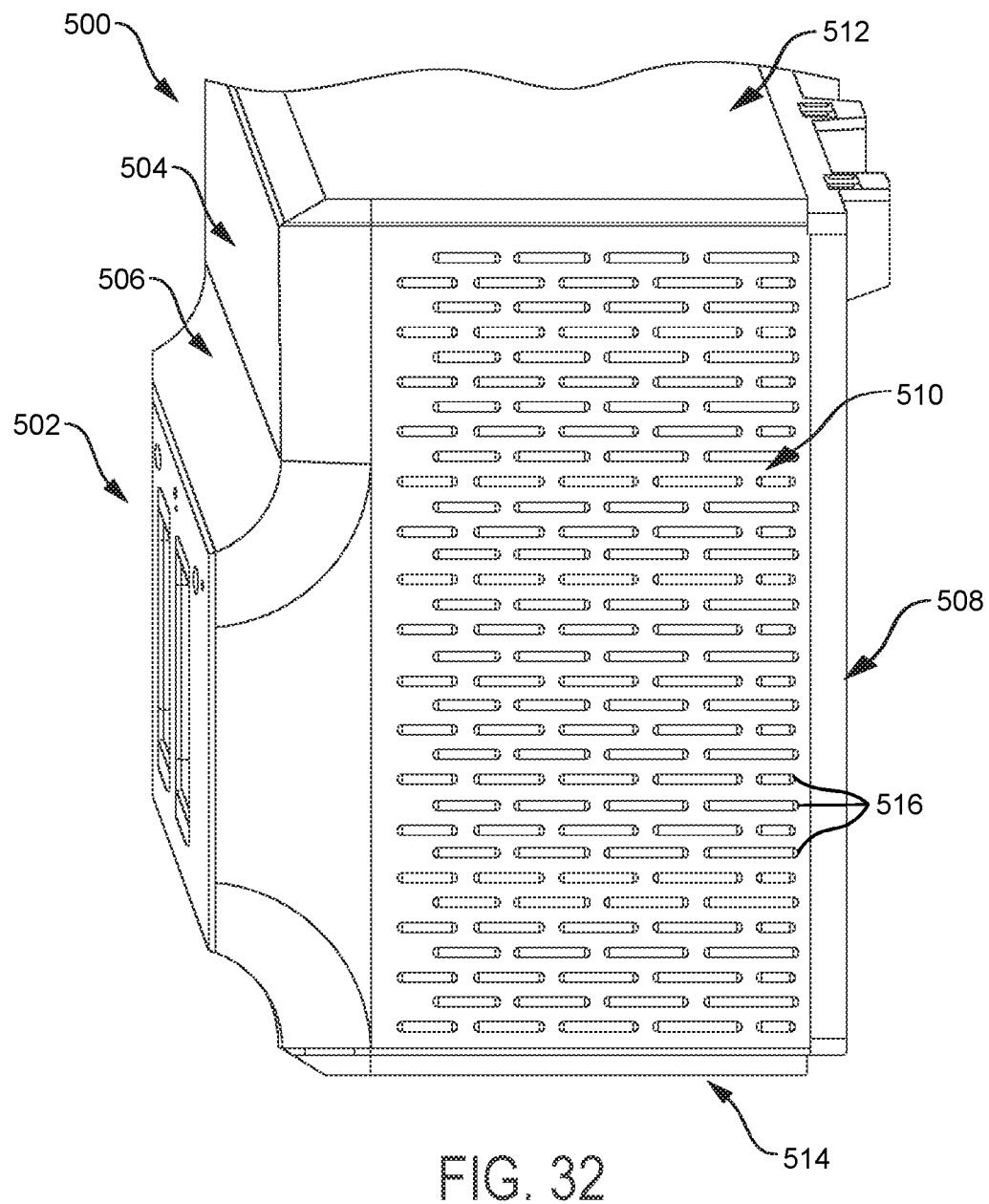
FIG. 32 illustrates an energy module including angled vents, according to at least one aspect of the present disclosure.
Figure 33:
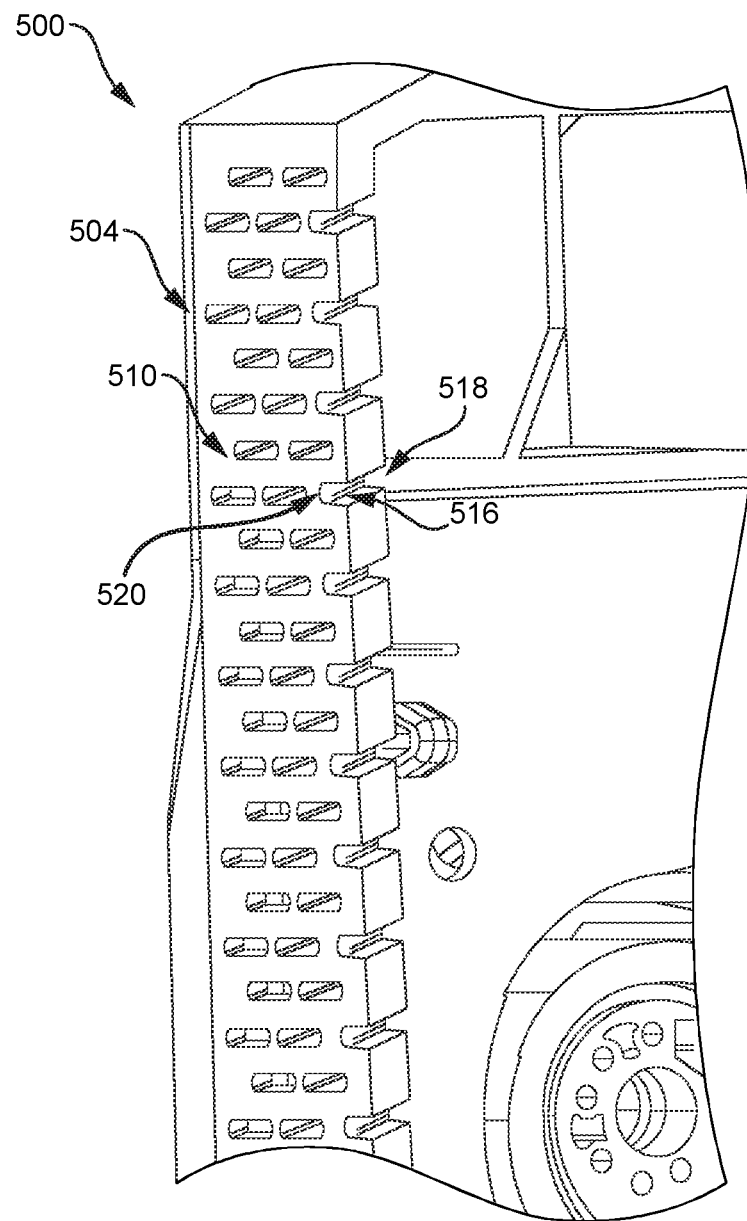
FIG. 33 illustrates a cross-sectional view of the energy module of FIG. 32 with the angled vents, according to at least one aspect of the present disclosure.
Figure 34:
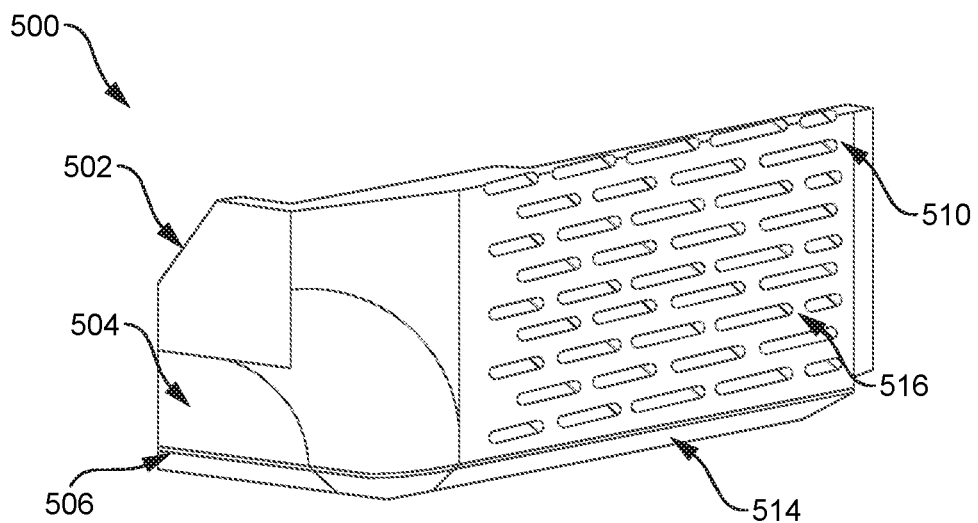
FIG. 34 illustrates a sidewall of an energy module including angled vents, according to at least one aspect of the present disclosure.
Figure 35:
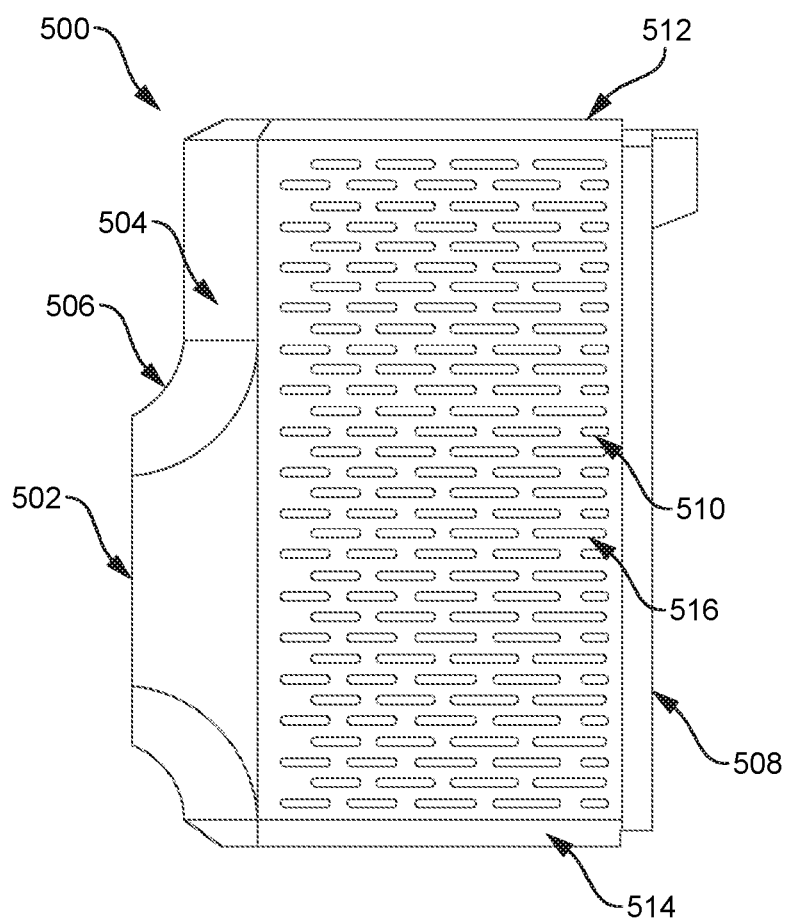
FIG. 35 illustrates a side view of an energy module including angled vents, according to at least one aspect of the present disclosure.
Figure 36:
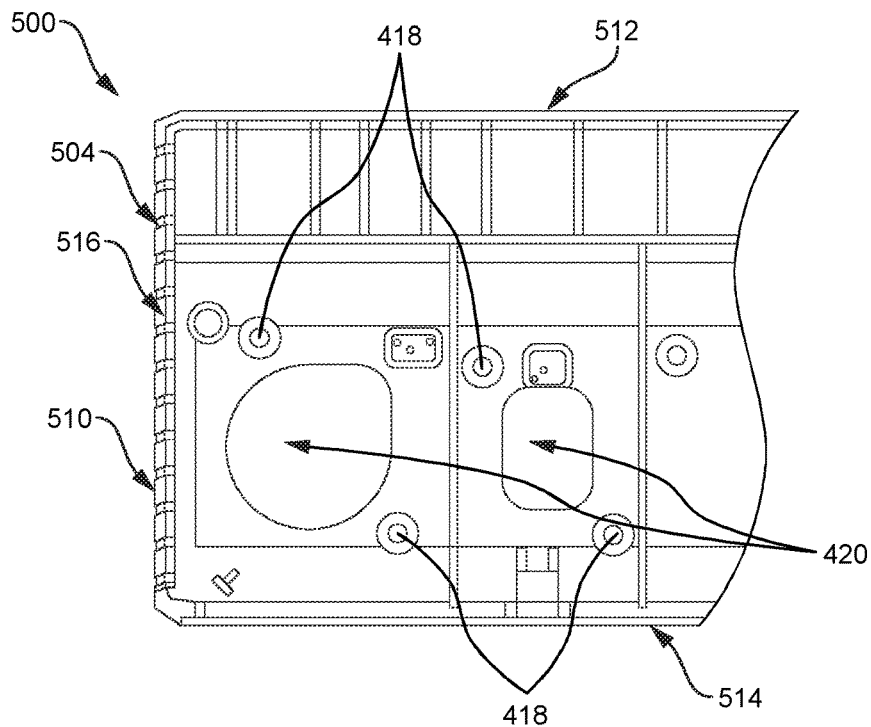
FIG. 36 illustrates a rear view of the energy module of FIG. 35, according to at least one aspect of the present disclosure.

Referring now to FIG. 32, a module 500 is provided according to at least one aspect of the present disclosure. The module can be any suitable module for use with a modular energy system, such as a header module 2002, an energy module 2004, a technology module 2040, a visualization module 2042, or any suitable module for use with a modular energy system. In one aspect, the module can be an energy module that includes a port assembly 502, which can be similar to port assembly 2012.

In one aspect, the module 500 can include an enclosure 504 that houses components of the module therein. The enclosure 504 can include a plurality of faces, such as a front face 506, a back face 508, a pair of sidewalls 510, a top face 512, and a bottom face 514. As shown in FIG. 32, the enclosure 504 of the module 500 can define vents 516, or holes, in the sidewalls 510 that can vent heat generated by the module 500 to prevent the module 500 from overheating. While vents 516 are shown and described are being defined in the sidewalls 510 of the enclosure 504, it should be understood that vents 516 can be defined in any suitable location on the enclosure 504, such as any other of the faces 506, 508, 512, 514 of the enclosure 504 for the purposes of venting heat generated by the module 500. In various aspects, the enclosure 504 can be defined with an injection molding process and the vents 516 can be drafted.

In one aspect, as shown most clearly in FIG. 37, the enclosure 504 can define vents 516 that can be angled relative to a sidewall plane defined by the sidewall 510 of the enclosure 504, which can hinder light escape from the enclosure 504. In various aspects, the vents 516 can include a vent inlet 518, a vent outlet 520, and a track 522 extending from the vent inlet 518 to the vent outlet 520. In one aspect, the tracks 522 can be angled θ relative to the sidewall plane at any suitable angle to inhibit light from escaping the enclosure 504. In one aspect, as is shown in FIG. 37, the vent inlets 518 and vent outlets 520 can be vertically offset such that the track 522 defines a non-perpendicularly angle θ relative to the sidewall plane. In one aspect, the vent inlets 518 and vent outlets 520 can be vertically offset such that the angle θ of the track 522 is 45° relative to the sidewall plane. In other aspects, the vent inlets 518 and vent outlets 520 can be offset such that the angle θ of the tracks 522 are greater than 45° relative to the sidewall plane, such as 50°, 55°, 60°, 70°, or any other suitable angle. In other aspects, the vent inlets 518 and vent outlets 520 can be offset such that the angle θ of the track 522 is less than 45° relative to the sidewall plane, such as 40°, 35°, 30°, 20°, or any other suitable angle. In various aspects, some vents 516 can include an angle θ that differs from other vents. Stated another way, the enclosure 504 can include non-uniformly angled vents 516 angled relative to the sidewall plane.

In one aspect, as is shown in FIG. 37, the enclosure 504 can define vents 516 that can be angled "downward", where the vent outlets 520 can be positioned vertically below the vent inlets 518, closer to the bottom face 514 of the enclosure. In various other aspects, the enclosure 504 can define vents 516 that can be angled "upward", where the vent outlets 520 can be positioned vertically above the vent inlets 518, closer to the top face 512 of the enclosure. In various other aspects, the enclosure 504 can include a combination of upward angled vents 516 and downward angled vents 516. In various aspects, the enclosure 504 can define vents 516 that are angled in other directions, such as forward angled or backward angled. For example, in various aspects, the enclosure 504 can define vents 516 that can be angled "forward", where the vent outlets 520 can be positioned closer to the front face 506 than the vent inlets 518. In various aspects, the enclosure 504 can define vents 516 that can be angled "backward", where the vent outlets 520 can be positioned closer to the back face 508 than the vent inlets 518. In various aspects, the enclosure 504 can define vents 516 that can be angled in more than one direction. For example, in one example aspect, the enclosure 504 can define vents 516 where the vent outlets 520 can be positioned closer to the front face 506 and the top face 512 when compared to the vent inlets 518. The use of angled vents can provide a similar, or improved, airflow compared to non-angled vents, as well as can provide the added benefit of preventing light from escaping the module. In various aspects, the enclosure 504 can define vents 516 that can be angled in a plurality of non-uniform directions.

As referenced above, the vents 516 can include a vent inlet 518, a vent outlet 520, and a track 522 extending from the vent inlet 518 to the vent outlet 520. In various aspects, the tracks 522 can be linear, as shown in FIG. 37. In various aspects, the tracks 522 can be non-linear (i.e., the tracks 522 non-linearly extend from the vent inlet 518 to the vent outlet 520). In various aspects, the track 522 can include a first track portion extending from the vent inlet 518 and a second track portion angled relative to the first track portion, extending from the first track portion and to the vent outlet 520. The use of multiple, angled track portions between the vent inlet 518 and vent outlet 520 can further prevent light from escaping the enclosure 504.

Low Pressure Mold (LPM) on a PCB for LED Light Blocking

As referenced elsewhere herein, modules of a modular energy system can utilize light for the purposes of conveying information to a user of the modular energy system. For example, ports 2012, 2014, 2016*a*, 2016*b*, 2018, 2020 can be configured to relay information to users. For example, any of the ports 2012, 2014, 2016*a*, 2016*b*, 2018, 2020 can include light assemblies 2015 that can be configured to relay information to the user regarding the port according to their color or state (e.g., flashing, solid, patterned, etc.). For example, a light assembly 2015 can change from a first color to a second color when a plug is fully seated within the respective port. As another example, a light assembly 2015 can flash a color, such as red, when a plug is improperly seated in the respective port. In one aspect, the color or state of the light assemblies 2015 can be controlled by the header module 2002. For example, the header module 2002 can cause the light assembly 2015 of each port to display a color corresponding to the color display for the port on the GUI 2008. Various other aspects are envisioned where the ports can shine any number of colors for the purposes of conveying information to a user, such as when a port is available for use, when a port is not available for use, when there is a problem with a port, an energy level of a port, etc.

As the light generated by the modules provides a user with critical information regarding the current state of the module, it is important that light generated within the module only be visible where intended. As referenced elsewhere herein, the modules can include an enclosure and a control circuit positioned therein. In one aspect, the control circuit can include a plurality of LEDs positioned thereon that face an inner wall of the enclosure and apertures defined in the enclosure. The plurality of LEDs can be grouped and positioned adjacent to the apertures defined in the enclosure such that, when information is to be conveyed to a user, a specific grouping of LEDs of the plurality of LEDs can be illuminated and shine through the respective aperture. This light can convey information associated with a port module that is positioned within the respective aperture, signifying a state of the port module (ready for use, not ready for use, an energy level associated with the port module, etc.).

As the plurality of LEDs can be grouped and positioned adjacent to a plurality of apertures defined in the enclosure, there is a chance that light generated by a first grouping of LEDs may be seen through not only the respective aperture associated with the first grouping of LEDs, but also another aperture that may be in close proximity to the first grouping of LEDs. For example, when light is emitted from LEDs, a user has no control over what direction the light emitted from the LEDs goes, which can result in light being seen at other locations within the module other than where intended, such as through other apertures defined in the enclosure. This inadvertent light shone through the unintended apertures may confuse the clinician as to what information the LEDs are intending to convey to the clinician. A need exists to ensure that this inadvertent light shining is eliminated.

Figure 38:
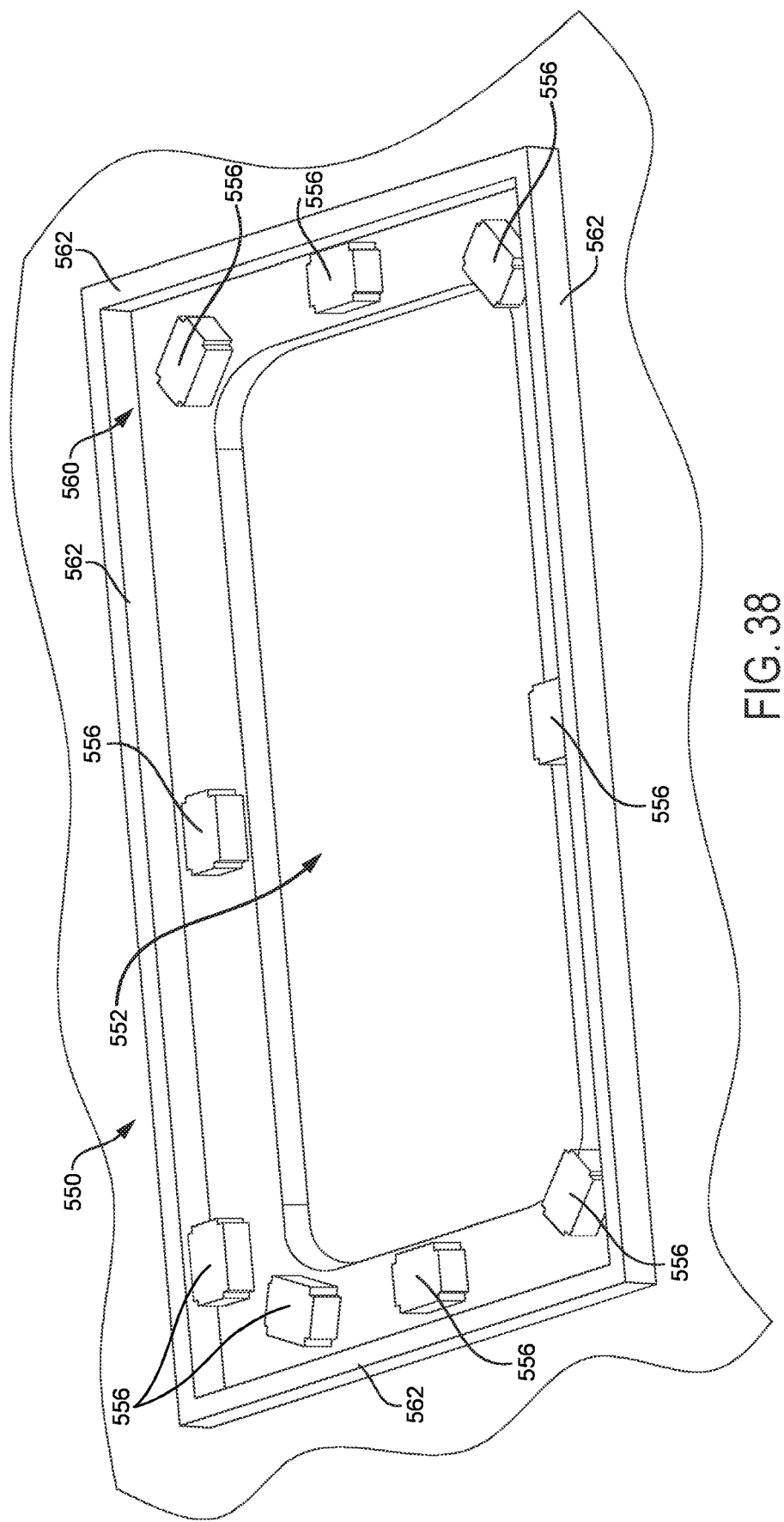
FIG. 38 illustrates a containment structure, according to at least one aspect of the present disclosure.

Referring now to FIG. 38, a control circuit 550 is provided, according to at least one aspect of the present disclosure. In various aspects, the control circuit 550 can include an aperture 552 defined therein that is sized to receive a port module, such as port modules 400, 401, 450 therein. In one aspect, the aperture 552 can be similar to apertures 432, 452. In various aspects, the control circuit 550 can further include a plurality of LEDs 556 surrounding the aperture 552. The LEDs 556 can be mounted to the control circuit 550 and can be in electrical communication therewith such that the control circuit 550 can control light that can be emitted by the LEDs. In one aspect, the control circuit 550 can control the LEDs 556 to cause the LEDs 556 to emit light according to a current status of a port module that is positioned within the aperture 552.

In various aspects, the control circuit 550 can further include a containment structure 560 including a plurality of sidewalls 562 extending from the control circuit 550. The containment structure 560 can be positioned on the control circuit 550 such that the sidewalls 562 encompass and surround the aperture 552 and the plurality of LEDs 556. In various aspects, the sidewalls 562 can extend a height from a surface of the control circuit 550 such that the height of the sidewalls 562 is greater than or equal to the height of the LEDs. As shown in FIG. 38, the containment structure 560 can define a rectangular-like shape to surround the LEDs 556 and the aperture 552. In various other aspects, the containment structure 560 can define any suitable shape such that the containment structure 560 surrounds the LEDs 556 and the aperture 552, such as a circular shape, a square shape, etc.

In one aspect, the containment structure 560 can be low pressure molded (LPM) directed onto the surface of the control circuit 550. Various other aspects are envisioned where the containment structure 560 is made separate from the control circuit 550 and removably coupled thereto with a bonding agent. In one aspect, the containment structure 560 can be comprised of an opaque material. In various aspects, the containment structure 560 can be comprised of an opaque plastic material. In various aspects, the containment structure 560 can be comprised of an opaque elastomer material. In one aspect, the use of the containment structure 560 can prevent light emitted from the LEDs 556 from traveling laterally along the control circuit 550; rather, the containment structure 560 can direct light emitted from the LEDs 556 toward the apertures defined in the enclosure of the module. In various aspects, the containment structure 560 can direct light emitted from the LEDs 556 toward light pipes of the port modules positioned in the aperture 552 of the control circuit 550.

In one aspect, the sidewalls 562 can be of uniform thickness. In various other aspects, the sidewalls 562 can have varying thicknesses. For example, in one aspect, sidewalls 562 that are positioned between other groupings of LEDs on the control circuit 550 can be thicker than sidewalls 562 that are not separating groups of LEDs on the control circuit. In various aspects, the sidewalls can be of non-uniform heights. In various aspects, the sidewalls can be of uniform heights. In one aspect, the sidewalls 562 of the containment structure 560 can be positioned close to the LEDs 556, as shown in FIG. 38, such that light emitted by the LEDs 556 can be stopped and redirected toward the apertures of the enclosure as soon as possible from the light being emitted by the LEDs 556.

It should be understood that various aspects of the disclosure described herein, such as the disclosure associated with FIGS. 17-38, as an example, may be utilized independently, or in combination, with one another.

EXAMPLES

Various aspects of the subject matter described herein are set out in the following numbered examples.

Example 1. A port module removably coupleable to an energy module of a module energy system, wherein the port module comprises a light pipe and a receptacle defined by the light pipe, wherein the receptacle is configured to receive a plug of an electrosurgical instrument therein, and wherein a seal is defined between the light pipe and the receptacle.

Example 2. The port module of Example 1, further comprising a mounting feature extending from the light pipe, wherein the energy module comprises an enclosure, and wherein the mounting feature is configured to mount to the enclosure.

Example 3. The port module of Example 2, wherein the mounting feature comprises a mounting arm and an aperture defined in the mounting arm.

Example 4. The port module of any or more of Examples 2 through 3, where a distance is defined between a front face of the light pipe and a front face of the mounting feature, and where the distance is selected to reduce occurrence of bright or dull spots of light emitted from the light pipe.

Example 5. The port module of any one or more of Examples 1 through 4, wherein the light pipe comprises engagement arm, wherein the receptacle defines a notch, and where the engagement arm is received within the notch.

Example 6. The port module of any one or more of Examples 1 through 5, wherein the receptacle comprises a back wall defining apertures, wherein the plug of the electrosurgical instrument comprises pins, and wherein the apertures are configured to receive the pins of the plug.

Example 7. The port module of any one or more of Examples 5 through 6, wherein the receptacle further comprises sidewalls extending from the back wall, and wherein the back wall and the sidewalls are comprised of an opaque material.

Example 8. An energy module of a module energy system, wherein the energy module comprises an enclosure defining a first aperture, a control circuit positioned within the enclosure, a port module, and a light blocking insert. The control circuit defines a second aperture aligned with the first aperture. The port module extends through the first aperture and the second aperture. A gap is defined between the second aperture and the port module. The light blocking insert is positioned in the gap.

Example 9. The energy module of Example 8, wherein the light blocking insert is configured to removably couple to the control circuit.

Example 10. The energy module of Example 9, wherein the light blocking insert comprises a plurality of mounting features, and wherein the plurality of mounting features are configured to removably couple the light blocking insert to the control circuit.

Example 11. The energy module of Example 10, wherein the mounting features comprise a lip configured to engage the control circuit to removably couple the light blocking insert to the control circuit.

Example 12. The energy module of any one or more of Examples 8 through 11, wherein the control circuit comprises an LED, and wherein the light blocking insert is configured to prevent light emitted from the LED from escaping through the gap.

Example 13. The energy module of Example 12, wherein the control circuit further comprises sidewalls surrounding the LED, wherein the sidewalls are configured to direct light emitted from the LED toward the first aperture.

Example 14. The energy module of Example 13, wherein the sidewalls are configured to prevent light emitted from the LED from escaping through the sidewalls.

Example 15. The energy module of any one or more of Examples 13 through 14, wherein the sidewalls are comprised of an opaque material.

Example 16. The energy module of any one or more of Examples 8 through 15, further comprising a vent, comprising a vent inlet, a vent outlet, and a track angularly extending from the vent inlet to the vent outlet.

Example 17. An energy module of a module energy system, wherein the energy module comprises an enclosure defining a first aperture, a control circuit positioned within the enclosure, a port module, and a light blocking insert. The control circuit defines a second aperture aligned with the first aperture. The port module extends through the first aperture and the second aperture. The port module comprises a light pipe and a receptacle, wherein the receptacle is configured to receive a plug of an electrosurgical instrument therein, wherein a seal is defined between the light pipe and the receptacle, and wherein a gap is defined between the second aperture and the port module. The light blocking insert is positioned in the gap.

Example 18. The energy module of Example 17, wherein the receptacle is comprised of an opaque material.

Example 19. The energy module of any one or more of Examples 17 through 18, wherein the port module is configured to removably couple to the enclosure.

Example 20. The energy module of any one or more of Examples 17 through 19, wherein the light blocking insert is configured to removably couple to the control circuit.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A port module removably coupleable to an energy module of a module energy system, wherein the port module comprises:
   a light pipe configured to receive light from a control circuit board in the energy module;
   a receptacle defined by the light pipe, wherein the receptacle is configured to receive a plug of an electrosurgical instrument therein, and wherein a seal is defined between the light pipe and the receptacle; and
   a port module control circuit communicably coupled to the control circuit board in the energy module, wherein a portion of the port module extends through the control circuit board in the energy module.

2. The port module of claim 1, further comprising a mounting feature extending from the light pipe, wherein the energy module comprises an enclosure, and wherein the mounting feature is configured to mount to the enclosure.

3. The port module of claim 2, wherein the mounting feature comprises:
   a mounting arm; and
   an aperture defined in the mounting arm.

4. The port module of claim 2, where a distance is defined between a front face of the light pipe and a front face of the mounting feature, and where the distance is selected to reduce occurrence of bright or dull spots of light emitted from the light pipe.

5. The port module of claim 1, wherein the light pipe comprises engagement arm, wherein the receptacle defines a notch, and where the engagement arm is received within the notch.

6. The port module of claim 1, wherein the receptacle comprises a back wall defining apertures, wherein the plug of the electrosurgical instrument comprises pins, and wherein the apertures are configured to receive the pins of the plug.

7. The port module of claim 5, wherein the receptacle further comprises sidewalls extending from a back wall, and wherein the back wall and the sidewalls are comprised of an opaque material.

8. An energy module of a module energy system, wherein the energy module comprises:
   an enclosure defining a first aperture;
   a control circuit board positioned within the enclosure, wherein the control circuit board defines a second aperture aligned with the first aperture;
   a port module extending through the first aperture and the second aperture, wherein a gap is defined between the second aperture and the port module, and wherein the port module comprises a receptacle configured to receive a plug of an electrosurgical instrument therein; and
   a light blocking insert positioned in the gap.

9. The energy module of claim 8, wherein the light blocking insert is configured to removably couple to the control circuit board.

10. The energy module of claim 9, wherein the light blocking insert comprises a plurality of mounting features, and wherein the plurality of mounting features are configured to removably couple the light blocking insert to the control circuit board.

11. The energy module of claim 10, wherein the mounting features comprise a lip configured to engage the control circuit board to removably couple the light blocking insert to the control circuit board.

12. The energy module of claim 8, wherein the control circuit board comprises an LED, and wherein the light blocking insert is configured to prevent light emitted from the LED from escaping through the gap.

13. The energy module of claim 12, wherein the control circuit board further comprises sidewalls surrounding the LED, wherein the sidewalls are configured to direct light emitted from the LED toward the first aperture.

14. The energy module of claim 13, wherein the sidewalls are configured to prevent light emitted from the LED from escaping through the sidewalls.

15. The energy module of claim 13, wherein the sidewalls are comprised of an opaque material.

16. The energy module of claim 8, further comprising a vent, comprising:
   a vent inlet;
   a vent outlet; and
   a track angularly extending from the vent inlet to the vent outlet.

17. An energy module of a module energy system, wherein the energy module comprises:
   an enclosure defining a first aperture;
   a control circuit board positioned within the enclosure, wherein the control circuit board defines a second aperture aligned with the first aperture;
   a port module extending through the first aperture and the second aperture, wherein the port module comprises:
      a light pipe; and
      a receptacle, wherein the receptacle is configured to receive a plug of an electrosurgical instrument therein, wherein a seal is defined between the light pipe and the receptacle, and wherein a gap is defined between the second aperture and the port module; and
   a light blocking insert positioned in the gap.

18. The energy module of claim 17, wherein the receptacle is comprised of an opaque material.

19. The energy module of claim 17, wherein the port module is configured to removably couple to the enclosure.

20. The energy module of claim 17, wherein the light blocking insert is configured to removably couple to the control circuit board.

* * * * *